US010131669B2

(12) United States Patent
Chappie et al.

(10) Patent No.: US 10,131,669 B2
(45) Date of Patent: Nov. 20, 2018

(54) PYRAZOLOPYRIMIDINE COMPOUNDS

(71) Applicant: Pfizer Inc., New York, NY (US)

(72) Inventors: Thomas Allen Chappie, Carlisle, MA (US); Patrick Robert Verhoest, Newton, MA (US); Nandini Chaturbhai Patel, Waban, MA (US); Matthew Merrill Hayward, Old Lyme, CT (US); Christopher John Helal, Mystic, CT (US); Simone Sciabola, Cambridge, MA (US); Travis T. Wager, Brookline, MA (US); Erik Alphie LaChapelle, Uncasville, CT (US); Joseph Michael Young, Madison, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/327,814

(22) PCT Filed: Jul. 10, 2015

(86) PCT No.: PCT/IB2015/055232
§ 371 (c)(1),
(2) Date: Jan. 20, 2017

(87) PCT Pub. No.: WO2016/012896
PCT Pub. Date: Jan. 28, 2016

(65) Prior Publication Data
US 2017/0204099 A1 Jul. 20, 2017

Related U.S. Application Data

(60) Provisional application No. 62/157,100, filed on May 5, 2015, provisional application No. 62/028,505, filed on Jul. 24, 2014.

(51) Int. Cl.
*C07D 487/04* (2006.01)
*A61K 31/519* (2006.01)

(52) U.S. Cl.
CPC ................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,814,651 A | 9/1998 | Duplantier et al. |
| 6,579,882 B2 | 6/2003 | Stewart et al. |
| 6,924,287 B1 | 8/2005 | Janssens et al. |
| 7,544,684 B2 | 6/2009 | Eggenweiler et al. |
| 7,605,168 B2 | 10/2009 | Ibrahim et al. |
| 7,709,518 B2 | 5/2010 | Chen et al. |
| 7,723,323 B2 | 5/2010 | Andersen et al. |
| 7,985,753 B2 | 7/2011 | Danysz et al. |
| 9,120,788 B2 | 9/2015 | Chappie et al. |
| 9,193,736 B2 | 11/2015 | Player et al. |
| 9,598,421 B2 | 3/2017 | Chappie et al. |
| 2003/0064031 A1 | 4/2003 | Humphrey et al. |
| 2003/0064374 A1 | 4/2003 | Ikhlef et al. |
| 2003/0069260 A1 | 4/2003 | Guadilliere et al. |
| 2003/0092706 A1 | 5/2003 | Barsig |
| 2003/0153595 A1 | 8/2003 | Walker et al. |
| 2003/0176450 A1 | 9/2003 | Atkinson et al. |
| 2003/0187257 A1 | 10/2003 | Gaudilliere |
| 2003/0187261 A1 | 10/2003 | Havlicek et al. |
| 2003/0191086 A1 | 10/2003 | Hanus et al. |
| 2004/0087588 A1 | 5/2004 | Beaton et al. |
| 2004/0157933 A1 | 8/2004 | Akiyama et al. |
| 2004/0162314 A1 | 8/2004 | Dube et al. |
| 2004/0176252 A1 | 9/2004 | Eggenweiler et al. |
| 2004/0176419 A1 | 9/2004 | Knowles et al. |
| 2004/0180918 A1 | 9/2004 | Knowles et al. |
| 2004/0235845 A1 | 11/2004 | Eggenweiler et al. |
| 2004/0242597 A1 | 12/2004 | Klein et al. |
| 2004/0254212 A1 | 12/2004 | Denholm et al. |
| 2004/0259863 A1 | 12/2004 | Eggenweiler et al. |
| 2005/0009829 A1 | 1/2005 | Nazare et al. |
| 2005/0014762 A1 | 1/2005 | Beume et al. |
| 2005/0020587 A1 | 1/2005 | Bailey et al. |
| 2005/0020593 A1 | 1/2005 | Mailliet et al. |
| 2005/0049263 A1 | 3/2005 | Kasibhatla et al. |
| 2005/0070514 A1 | 3/2005 | Rapeport |
| 2005/0070569 A1 | 3/2005 | Guay et al. |
| 2005/0101000 A1 | 5/2005 | Bennett et al. |
| 2005/0137234 A1 | 6/2005 | Bressi et al. |
| 2005/0272803 A1 | 12/2005 | Ruiping et al. |
| 2005/0289660 A2 | 12/2005 | Wang et al. |
| 2006/0025426 A1 | 2/2006 | Fraley |
| 2006/0041006 A1 | 2/2006 | Ibrahim et al. |
| 2006/0148805 A1 | 7/2006 | Chen et al. |
| 2006/0183909 A1 | 8/2006 | Schmitt et al. |
| 2007/0010521 A1 | 1/2007 | Ukita et al. |
| 2007/0191426 A1 | 8/2007 | Edlin et al. |
| 2007/0275984 A1 | 11/2007 | Imogai |
| 2008/0096884 A1 | 4/2008 | Edlin et al. |
| 2008/0096903 A1 | 4/2008 | Cehn et al. |
| 2008/0102475 A1 | 5/2008 | Kan et al. |
| 2009/0029938 A1 | 1/2009 | Renzi et al. |
| 2009/0176778 A1 | 7/2009 | Schmitz et al. |
| 2009/0275586 A1 | 11/2009 | Govek et al. |

(Continued)

FOREIGN PATENT DOCUMENTS

CA 2931026 6/2015
IN 55MUM2009 9/2010

(Continued)

OTHER PUBLICATIONS

Spina, British Journal of Pharmacology vol. 155, p. 308-315 (2008).*

(Continued)

*Primary Examiner* — Emily A Bernhardt
(74) *Attorney, Agent, or Firm* — Richard V. Zanzalari

(57) ABSTRACT

The present invention is directed to pyrazolopyrimine compounds or pharmaceutically acceptable salts which are inhibitors of PDE4 isozymes, especially with a binding affinity for PDE4B isoform, and compositions thereof.

3 Claims, No Drawings

(56) References Cited

U.S. PATENT DOCUMENTS

| | | | |
|---|---|---|---|
| 2010/0105729 A1 | 4/2010 | Govek et al. | |
| 2010/0130737 A1 | 5/2010 | Itoh et al. | |
| 2010/0204265 A1 | 8/2010 | Baskaran et al. | |
| 2010/0267714 A1 | 10/2010 | Jorgensen et al. | |
| 2011/0003820 A1 | 1/2011 | Henrich et al. | |
| 2011/0173726 A1 | 7/2011 | Grob et al. | |
| 2011/0275623 A1 | 10/2011 | Baker et al. | |
| 2011/0275622 A1 | 11/2011 | Baker et al. | |
| 2012/0041045 A1 | 2/2012 | Harvey et al. | |
| 2012/0122888 A1 | 5/2012 | Xu et al. | |
| 2012/0283274 A1 | 11/2012 | Plitt et al. | |
| 2012/0289474 A1 | 11/2012 | Flockerzi et al. | |
| 2014/0235612 A1 | 8/2014 | Chappie et al. | |
| 2017/0145022 A1 | 5/2017 | Chappie et al. | |

FOREIGN PATENT DOCUMENTS

| | | |
|---|---|---|
| JP | 08295667 | 11/1996 |
| WO | 2000075145 | 12/2000 |
| WO | 2001083481 | 11/2001 |
| WO | 2003000697 | 1/2003 |
| WO | 2003008373 | 1/2003 |
| WO | 2003008396 | 1/2003 |
| WO | 2003015789 | 2/2003 |
| WO | 2003035650 | 5/2003 |
| WO | 2004042390 | 5/2004 |
| WO | 2004089471 | 10/2004 |
| WO | 2006034312 | 3/2006 |
| WO | 2006050976 | 5/2006 |
| WO | 2006089689 | 8/2006 |
| WO | 2007107499 | 9/2007 |
| WO | 2008004117 | 1/2008 |
| WO | 2008006050 | 1/2008 |
| WO | 2008006051 | 1/2008 |
| WO | 2008006052 | 1/2008 |
| WO | 2008015271 | 2/2008 |
| WO | 2008025822 | 3/2008 |
| WO | 2008033739 | 3/2008 |
| WO | 2008056176 | 5/2008 |
| WO | 2009023623 | 2/2009 |
| WO | 2009108551 | 9/2009 |
| WO | 2010004306 | 1/2010 |
| WO | 2010059836 | 5/2010 |
| WO | 2011051342 | 5/2011 |
| WO | 2011093924 | 8/2011 |
| WO | 2011119465 | 9/2011 |
| WO | 2013028263 | 2/2013 |
| WO | 2014128585 | 8/2014 |
| WO | 2016012896 | 1/2016 |
| WO | 2016020786 | 6/2016 |

OTHER PUBLICATIONS

Kumar et al. BMC Medicine vol. 11:96 pp. 1-8 (2013).*
English Translation of Japanese Patent Application Publication No. 8-295667, published Nov. 12, 1996.
Deninno, Michael P., "Future Directions in Phosphodiesterase Drug Discovery", Bioorganic and Medicinal Chemishy Letters, Nov. 15, 2012, pp. 6794-6800, 22(22).
Papp, K., et al., "Efficacy of apremilast in the treatment of moderate to severe psoriasis: a randomized controlled trial", Lancet, Aug. 25-31, 2012, pp. 738-746, 380(9843).
Donnell, A. F., et al., "Identification of pyridazio[4,5-b]indolizines as selective PDE4B Inhibitors", Bioorganic & Medicinal Chemistry Letters, Apr. 1, 2010, pp. 2163-2167, 20(7).
Naganuma, K., et al., "Discovery of selective PDE4B inhibitors", Bioorganic & Medicinal Chemistry Letters, Jul. 15, 2009, pp. 3174-3176, 19(12).
Robichaud, A., et al., "Deletion of phosphodiesterase 4D in mice shortens α2-adrenoreceptor-mediated anesthesia, a behavioral correlate of emesis", Journal of Clinical Investigation, Oct. 1, 2002, pp. 1045-1052, 110(7).

Siuciak, J. A., et al., "Antipsychotic profile of rolipram: efficacy in rats and reduced sensitivity in mice deficient in the phosphodiesterase-4B (PDE4B) enzyme", Psychopharmacology, Jun. 2007, pp. 415-425, 192(3).
Millar, J. K., et al., "Disrupted in schizophrenia 1 and phosphodiesterase 4B: towards an understanding of psychiatric illness", Journal of Physiology, Oct. 2007, pp. 401-405, 584(2).
Wang, C., et al., "The phosphodiesterase-4 inhibitor rolipram reverses Aβ-induced cognitive impairment and neuroinflammatory and apoptotic responses in rats", International Journal of Neuropsychopharmacology, Jul. 2012, pp. 749-766, 15(6).
Fujita, M., et al., "Downregulation of Brain Phosphodiesterase Type IV Measured with 11C-(R)-Rolipram Positron Emission Tomography in Major Depressive Disorder", Biological Psychiatry, Oct. 1, 2012, pp. 548-554, 72(7).
Sun, X., et al., "Rolipram promotes remyelination possibly via MEK-ERK signal pathway in cuprizone-induced demyelination mouse", Experimental Neurology, 2012, pp. 304-311, 237(2).
Hess, A., et al., "Blockade of Tnf-α rapidly inhibits pain responses in the central nervous system", Proceedings of the National Academy of Sciences of the United States of American, Mar. 1, 2011, pp. 3731-3736, 108(9).
Schafer, Peter, et al., "Apremilast mechanism of action and application to psoriasis and psoriatic arthritis", Biochemical Pharmacology, Jun. 15, 2012, pp. 1583-1590, 83(12).
Schmidt, A., et al., "BDNF and PDE4, but not the GRPR, Regulate Viability of Human Medulloblastoma Cells", Journal of Molecular Neuroscience, Mar. 2010, pp. 303-310, 40(3).
Marquette, A., et al., "ERK and PDE4 cooperate to induce RAF isoform switching in melanoma", Nature Structural & Molecular Biology, May 2011, pp. 584-591, 18(5).
Kim, D. H., et al., "Type 4 Cyclic Adenosine Monophosphate Phosphodiesterase as a Therapeutic Target in Chronic Lymphocytic Leukemia", Blood Journal of The American Society of Hematology, Oct. 1, 1998, pp. 2484-2494, 92(7).
Vollert, S., et al., "The glucose-lowering effects of the PDE4 inhibitors roflumilast and roflumilast-N-oxide in db/db mice", Diabetologia, Oct. 2012, pp. 2779-2788, 55(10).
Venable, J., et al., "Preparation and Biological Evaluation of Indole, Benzimidazole, and Thienopyrrole Piperazine Carboxamides: Potent Human Histamine H4 Antagonists", Journal of Medicinal Chemistry, 2005, pp. 8289-8298, vol. 4.
Patriciu, Oana-Irian, et al., "Smiles Rearrangement as a Tool for the Preparation of Dihydrodipyridopyrazines", Organic Letter, 2009, pp. 5502-5505, vol. 11.
Seeger, T. F., et al., "Immunohistochemical localization of PDE10A in the rat brain", Brain Research, Sep. 26, 2003, pp. 113-126, 985(2).
Burgin, A.B., et al., "Design of phosphodiesterase 4D (PDE4D) allosteric modulators for enhancing cognition with improved safety", Nature Biotechnology Advance Online Publication, 2010, pp. 63-72, vol. 28.
Schett, G., et al., "Apremilast: A novel PDE4 inhibitor in the treatment of autoimmune and inflammatory diseases", Therapeutic Advances Musculoskeletal Diseases, Aug. 16, 2010, pp. 271-278, 2(5).
Wouters, E.F., et al., "Effect of the Phosphodiesterase 4 Inhibitor Roflumilast on Glucose Metabolism in Patients with Treatment-Naïve, Newly Diagnosed Type 2 Diabetes Mellitus", Journal of Clinical Endocrinology and Metabolism, Sep. 2012, pp. 1720-1725, vol. 97, Abstract Only.
Patan, E., et al., "Efficacy and safety of apremilast, an oral phosphodiesterase 4 inhibitor, in ankylosing spondylitis", Annals of Rheumatic Diseases, Sep. 1, 2013, pp. 1475-1480, 72(9), Abstract Only.
International Patent Application No. PCT/IB2014/058840, filed Feb. 6, 2014, International Search Report and Written Opinion, dated Mar. 25, 2014, 13 pages.
Dorange, Ismet, et al., "Discovery of novel pyrrolopyridazine scaffolds as transient receptor potential vanilloid (TRPV1) antagonists", Bioorganic & Medicinal Chemistry Letters, 2012, pp. 6888-6895, vol. 22.

(56) References Cited

OTHER PUBLICATIONS

Tseng, Tehuang, etc., "The synthesis of Daidzein Derivatives", The Journal of National Taiwan Normal University, 1985, pp. 537-545, vol. 30, Abstract Only.

International Patent Application No. PCT/IB2015/055232, filed Jul. 10, 2015, International Search Report and Written Opinion dated Oct. 13, 2015, 12 pages.

Kodimuthali, Arumugam, et al., "Evaluation of Novel 7-(hetero)aryl-substituted Pyrazolo[1,5-a]pyrimidines as phosphodiesterase-4 Inhibitors", Letters in Drug Design & Discovery, Jul. 2010, pp. 402-408, 7(6).

Kumar, Mahesh P., et al., "(Pd/C-mediated)coupling-iodocyclization-coupling strategy in discovery of novel PDE4 inhibitors: a new synthesis of pyrazolopyrimidines", MedChemComm, 2012, pp. 667-672, vol. 3.

Ram, Vishnu J., et al., "Regioselective synthesis of substituted and fused pyrazolo[1,5-a]pyrimidines as leishmanicides", Indian Journal of Chemistry, Section B: Organic Chemistry Including Medicinal Chemistry, 1995, pp. 416-422, 348(5).

International Patent Application No. PCT/IB2015/055597, filed Jul. 23, 2015 International Search Report and Written Opinion, dated Oct. 16, 2015, 12 pages.

International Patent Application No. PCT/IB2014/058840, filed Feb. 6, 2014, International Preliminary Report on Patentability, dated Aug. 25, 2105, 7 pages.

International Patent Application PCT/IB2015/055597, filed Jul. 23, 2015 International International Preliminary Report on Patentability, dated Feb. 16, 2017, 7 pages.

International Patent Application No. PCT/IB2015/055232, filed Jul. 10, 2015, International Preliminary Report on Patentability, dated Feb. 2, 2017, 7 pages.

Dorange, et al., "Discovery of novel pyrrolopyridazine scaffolds as transient receptor potential vanilloid (TRPV1) antagonists", Bioorg. Med. Chem. Letter., 2012, pp. 6888-6895, 22(22).

* cited by examiner

PYRAZOLOPYRIMIDINE COMPOUNDS

This application is a national stage application under 35 U.S.C. 371 of PCT/IB2015/055232, filed on Jul. 10, 2015, which claims the benefit of U.S. Provisional Patent Application No. 62/157,100, filed on May 5, 2015, and U.S. Provisional Patent Application No. 62/028,505, filed on Jul. 24, 2014, the disclosures of which are hereby incorporated by reference in their entirety.

FIELD OF THE INVENTION

The present invention relates to pyrazolopyrimidine compounds of Formula I, which are inhibitors of PDE4 isozymes, especially with a binding affinity for the PDE4B isoform, and to the use of such compounds in methods for treating central nervous system (CNS), metabolic, autoimmune and inflammatory diseases or disorders.

BACKGROUND OF THE INVENTION

Phosphodiesterases (PDEs) are a class of intracellular enzymes that degrade the phosphodiester bond in second messenger molecules cyclic adenosine monophosphate (cAMP) and cyclic guanosine monophosphate (cGMP). The cyclic nucleotides cAMP and cGMP serve as secondary messengers in various cellular pathways.

cAMP functions as a second messenger regulating many intracellular processes within the body. An example is in the neurons of the central nervous system, where the activation of cAMP-dependent kinases and the subsequent phosphorylation of proteins is involved in acute regulation of synaptic transmission as well as neuronal differentiation and survival. The complexity of cyclic nucleotide signaling is indicated by the molecular diversity of the enzymes involved in the synthesis and degradation of cAMP. There are at least ten families of adenylyl cyclases, and eleven families of phosphodiesterases. Furthermore, different types of neurons are known to express multiple isozymes of each of these classes, and there is good evidence for compartmentalization and specificity of function for different isozymes within a given neuron.

The principal mechanism for regulating cyclic nucleotide signaling is via phosphodiesterase-catalyzed cyclic nucleotide catabolism. The 11 known families of PDEs are encoded by 21 different genes; each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE isozymes may offer particular therapeutic effects, fewer side effects, or both (Deninno, M., *Future Directions in Phosphodiesterase Drug Discovery*. Bioorganic and Medicinal Chemistry Letters 2012, 22, 6794-6800).

The present invention relates to compounds having a binding affinity for the fourth family of PDEs (i.e., PDE4A, PDE4B, PDE4C, and PDE4D), and, in particular, a binding affinity for the PDE4B isoform.

The PDE4 isozymes are characterized by selective, high-affinity hydrolytic degradation of the second messenger cyclic adenosine 3',5'-monophosphate (cAMP). Beneficial pharmacological effects resulting from that inhibition have been shown in a variety of disease models. A number of other PDE4 inhibitors have been discovered in recent years. For example, Roflumilast (Daliresp®), marketed by Forest Pharmaceuticals, Inc., is approved for severe chronic obstructive pulmonary disease (COPD) to decrease the number of flare-ups or the worsening of COPD symptoms (exacerbations). Apremilast (Otezla®) has been approved by the U.S. Food and Drug Administration for the treatment of adults with active psoriatic arthritis.

While beneficial pharmacological activity of PDE4 inhibitors has been shown, a common side-effect of these treatments has been the induction of gastrointestinal side effects such as nausea, emesis, and diarrhea, which are currently believed to be associated with inhibition of the PDE4D isoform. Attempts were made to develop compounds with an affinity for the PDE4B isoform over the PDE4D isoform (See: Donnell, A. F. et al., *Identification of pyridazino[4,5-b]indolizines as selective PDE4B inhibitors*. Bioorganic & Medicinal Chemistry Letters 2010; 20:2163-7; and Naganuma, K. et al., *Discovery of selective PDE4B inhibitors*. Bioorganic & Medicinal Chemistry Letters 2009; 19:3174-6). However, there remains a need to develop PDE4 inhibitors, especially those having an affinity for the PDE4B isoform. In particular, there remains a need to develop compounds that have enhanced binding affinity for the PDE4B isoform over the PDE4D isoform for the treatment of various diseases and disorders of the central nervous system (CNS). The discovery of selected compounds of the present invention addresses this continued need, and provides additional therapies for the treatment of various diseases and disorders of the central nervous system (CNS), as well as metabolic, autoimmune and inflammatory diseases or disorders.

Treatment with the PDE4B inhibitors of the present invention may also lead to a decrease in gastrointestinal side effects (e.g., nausea, emesis and diarrhea) believed to be associated with inhibition of the PDE4D isoform (Robichaud, A. et al., *Deletion of Phosphodiesterase 4D in Mice Shortens α2-Adrenoreceptor-Mediated Anesthesia, A Behavioral Correlate of Emesis*. Journal of Clinical Investigation 2002, Vol. 110, 1045-1052).

SUMMARY OF THE INVENTION

The present invention is directed to compounds of Formula I:

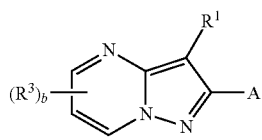

or a pharmaceutically acceptable salt thereof, wherein:

$R^1$ is selected from the group consisting of —$(CH_2)_m$—$(C_3$-$C_8)$cycloalkyl, —$(CH_2)_m$-(4- to 10-membered)heterocycloalkyl, —$(CH_2)_m$—$(C_6$-$C_{10})$aryl and —$(CH_2)_m$-(5- to 14-membered)heteroaryl, and, where chemically permissible, the $(C_3$-$C_8)$cycloalkyl, (4- to 10-membered)heterocycloalkyl, $(C_6$-$C_{10})$aryl and (5- to 14-membered)heteroaryl moieties are optionally substituted with one to five $R^2$;

when present, each $R^2$ is independently selected from the group consisting of halogen, oxo, cyano, hydroxy, —$SF_5$, nitro, optionally substituted $(C_1$-$C_6)$alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C=(O)R$^5$), —C(=O)N(R$^4$)(R$^5$), —C(=O)—O—N(R$^4$)(R$^5$), —C(=O)—R$^4$, —C(=O)—OR$^4$, and optionally substituted (C$_3$-C$_8$)cycloalkyl;

A is represented by formula A$^1$ or A$^2$:

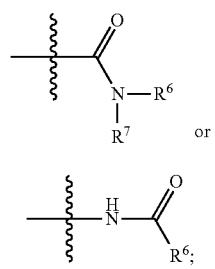

when present, each R$^3$ is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C=(O)R$^5$), —C(=O)N(R$^4$)(R$^5$), —C(=O)—O—N(R$^4$)(R$^5$), —C(=O)—R$^4$, and —C(=O)—OR$^4$;

R$^4$ and R$^5$ are each independently selected from the group consisting of hydrogen, and optionally substituted (C$_1$-C$_6$)alkyl;

R$^6$ and R$^7$ are each independently selected from the group consisting of hydrogen, optionally substituted (C$_1$-C$_8$)alkyl, —(CH$_2$)$_n$—(C$_3$-C$_8$)cycloalkyl, —(CH$_2$)$_n$-(4- to 10-membered) heterocycloalkyl, —(CH$_2$)$_n$—(C$_8$-C$_{10}$)aryl, and —(CH$_2$)$_n$-(5- to 10-membered)heteroaryl, and where chemically permissible, the (C$_3$-C$_8$)cycloalkyl, (4- to 10-membered) heterocycloalkyl, (C$_8$-C$_{10}$)aryl, and (5- to 10-membered)heteroaryl are optionally substituted with one to five R$^8$; or R$^6$ and R$^7$ taken together with the nitrogen to which they are attached form a (4- to 10-membered)heterocycloalkyl, and where chemically permissible, the (4- to 10-membered)-heterocycloalkyl is optionally substituted with one to five R$^9$;

when present, each R$^8$ is independently selected from the group consisting of halogen, oxo, cyano, hydroxy, —SF$_5$, nitro, optionally substituted (C$_1$-C$_8$)alkyl, optionally substituted (C$_2$-C$_8$)alkenyl, optionally substituted (C$_2$-C$_8$)alkynyl, optionally substituted (C$_1$-C$_8$)alkylthio, optionally substituted (C$_1$-C$_8$)alkoxy, —N(R$^4$)(R$^5$), —N(R$^4$)(C=(O)R$^5$), —C(=O)N(R$^4$)(R$^5$), —C(=O)—O—N(R$^4$)(R$^5$), —C(=O)—R$^4$, and —C(=O)—OR$^4$;

when present, each R$^9$ is independently selected from the group consisting of halogen, oxo, cyano, hydroxy, —SF$_5$, nitro, optionally substituted (C$_1$-C$_8$)alkyl, optionally substituted (C$_2$-C$_8$)alkenyl, optionally substituted (C$_2$-C$_8$)alkynyl, optionally substituted (C$_1$-C$_8$)alkylthio, optionally substituted (C$_1$-C$_8$)alkoxy, —N(R$^4$)(R$^5$), —N(R$^4$)(C=(O)R$^5$), —C(=O)N(R$^4$)(R$^5$), —C(=O)—O—N(R$^4$)(R$^5$), —C(=O)—R$^4$, and —C(=O)—OR$^4$;

b is represented by an integer selected from 0, 1, 2, or 3;

m is represented by an integer selected from 0, 1, or 2; and n is represented by an integer selected from 0, 1, 2, 3 or 4.

Compounds of the invention include Examples 1-2, and 4-76 or a pharmaceutically acceptable salt thereof as described herein.

The compounds of Formula I are inhibitors of the PDE4B isoform.

The compounds of Formula I are useful for treating or preventing diseases and/or disorders of the central nervous system (CNS), pain, trauma, cardiologic, thrombotic, metabolic, autoimmune and inflammatory diseases or disorders, and disorders associated with enhanced endothelial activity/impaired endothelial barrier function.

The present invention is also directed to the use of the compounds described herein, or a pharmaceutically acceptable salt thereof, in the preparation of a medicament for the treatment or prevention of a condition amenable to modulation of the PDE4B gene family (i.e., PDE4B enzymes).

The present invention is also directed to pharmaceutically acceptable formulations containing an admixture of a compound(s) of the present invention and at least one excipient formulated into a pharmaceutical dosage form. Examples of such dosage forms include tablets, capsules, suppositories, gels, creams, ointments, lotions, solutions/suspensions for injection (e.g., depot), aerosols for inhalation and solutions/suspensions for oral ingestion.

DETAILED DESCRIPTION OF THE INVENTION

The headings within this document are only being utilized to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

As used herein, the term "n-membered" where n is an integer typically describes the number of ring-forming atoms in a moiety where the number of ring-forming atoms is n. For example, pyridine is an example of a 6-membered heteroaryl ring and thiazole is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "(C$_1$-C$_6$) alkyl" is specifically intended to include C$_1$ alkyl (methyl), C$_2$ alkyl (ethyl), C$_3$ alkyl, C$_4$ alkyl, C$_5$ alkyl, and C$_6$ alkyl. For another example, the term "a (5- to 14-membered) heteroaryl group" is specifically intended to include any 5-, 6-, 7-, 8-, 9-, 10-, 11-, 12-, 13- and 14-membered heteroaryl group.

The term "(C$_1$-C$_6$)alkyl" as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl.

The term "optionally substituted (C$_1$-C$_6$)alkyl", as used herein, refers to a (C$_1$-C$_6$)alkyl as defined above, in which one or more hydrogen atoms are replaced by a substituent selected from the group consisting of halogen, oxo, cyano, hydroxy, —SF$_5$, nitro, —N(R$^4$)(R$^5$), —N(R$^4$)(C(=O)R$^5$), —N(R$^4$)C(=O)—OR$^5$, —C(=O)—N(R$^4$)(R$^5$), —C(=O)—O—N(R$^4$)(R$^5$), —C(=O)—R$^4$, —C(=O)—OR$^4$, and (C$_3$-C$_8$)cycloalkyl, in which R$^4$ and R$^5$ are each independently hydrogen or optionally substituted $(C_1-C_6)$ alkyl. For example, a $(C_1-C_6)$alkyl moiety can be substituted with one or more halogen atoms to form a "halo$(C_1-C_6)$ alkyl". Representative examples of a halo$(C_1-C_6)$alkyl include, but are not limited to, fluoromethyl, difluoromethyl, 2-fluoroethyl, trifluoromethyl, pentafluoroethyl, and 2-chloro-3-fluoropentyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $C_2-C_6$alkenyl group, the compound may exist as the pure E (entgegen) form, the pure Z (zusammen) form, or any mixture thereof.

The term "optionally substituted $(C_2-C_6)$alkenyl" refers to a $(C_2-C_6)$alkenyl as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(\!=\!O)R^5)$, —$N(R^4)C(\!=\!O)$—$OR^5$, —$C(\!=\!O)$—$N(R^4)(R^5)$, —$C(\!=\!O)$—O—$N(R^4)(R^5)$, —$C(\!=\!O)$—$R^4$, —$C(\!=\!O)$—$OR^4$, and $(C_3-C_8)$cycloalkyl, in which $R^4$ and $R^5$ are each independently hydrogen or optionally substituted $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynl, butynyl, pentynyl, and hexynyl.

The term "optionally substituted $(C_2-C_6)$alkynyl" refers to a $(C_2-C_6)$alkynyl as defined above, in which one or more hydrogen atoms are replaced by a substituent selected from the group consisting of halogen, oxo, cyano, hydroxy, —$SF_5$, —$N(R^4)(R^5)$, —$N(R^4)(C(\!=\!O)R^5)$, —$N(R^4)C(\!=\!O)$—$OR^5$, —$C(\!=\!O)$—$N(R^4)(R^5)$, —$C(\!=\!O)$—O—$N(R^4)(R^5)$, —$C(\!=\!O)$—$R^4$, —$C(\!=\!O)$—$OR^4$, and $(C_3-C_8)$ cycloalkyl, in which $R^4$ and $R^5$ are each independently hydrogen or optionally substituted $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy.

The term "optionally substituted $(C_1-C_6)$alkoxy" as used herein, refers to a $(C_1-C_6)$alkoxy group, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(\!=\!O)R^5)$, —$N(R^4)C(\!=\!O)$—$OR^5$, —$C(\!=\!O)$—$N(R^4)(R^5)$, —$C(\!=\!O)$—O—$N(R^4)(R^5)$, —$C(\!=\!O)$—$R^4$, —$C(\!=\!O)$—$OR^4$, and $(C_3-C_8)$cycloalkyl, in which $R^4$ and $R^5$ are each independently hydrogen or optionally substituted $(C_1-C_6)$alkyl. For example, a "$(C_1-C_6)$alkoxy can be substituted with one or more halogen atoms to form a "halo$(C_1-C_6)$alkoxy". Representative examples of a halo $(C_1-C_6)$alkoxy include, but are not limited to, fluoromethoxy, difluoromethoxy, 2-fluoroethoxy, trifluoromethoxy, and pentafluoroethoxy.

The term "$(C_1-C_6)$alkythio" as used herein, refers to a $(C_1-C_6)$alkyl group, as defined above, attached to the parent molecular moiety through a sulfur atom. Representative examples of a $(C_1-C_6)$alkylthio include, but are not limited to, thiomethoxy, thioethoxy, thiopropoxy, and the like.

The term "optionally substituted $(C_1-C_6)$alkylthio" as used herein, refers to a $(C_1-C_6)$alkylthio group, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(\!=\!O)R^5)$, —$N(R^4)C(\!=\!O)$—$OR^5$, —$C(\!=\!O)$—$N(R^4)(R^5)$, —$C(\!=\!O)$—O—$N(R^4)(R^5)$, —$C(\!=\!O)$—$R^4$, —$C(\!=\!O)$—$OR^4$, and $(C_3-C_8)$cycloalkyl, in which $R^4$ and $R^5$ are each independently hydrogen or optionally substituted $(C_1-C_6)$alkyl.

As used herein, the term "$(C_3-C_8)$cycloalkyl" refers to a carbocyclic substituent obtained by removing a hydrogen from a saturated carbocyclic molecule wherein the cyclic framework has 3 to 8 carbons. A "$(C_3-C_6)$cycloalkyl" refers to a carbocyclic substituent obtained by removing a hydrogen from a saturated carbocyclic molecule having from 3 to 6 carbon atoms. A "cycloalkyl' may be a monocyclic ring, examples of which include cyclopropyl, cyclobutyl, cyclopentyl, cyclohexyl, cycloheptyl, and cyclooctyl. Also included in the definition of cycloalkyl are unsaturated cycloalkyls such as, but not limited to, cyclohexenyl, cyclohexadienyl, cyclopentenyl, cycloheptenyl, and cyclooctenyl. Alternatively, a cycloalkyl may contain more than one ring such as a "$(C_4-C_8)$bicycloalkyl". The term "$(C_4-C_8)$bicycloalkyl" refers to a bicyclic ring system containing from 4 to 8 carbon atoms. The bicycloalkyl may be fused, such as bicyclo[1.1.0]butanyl, bicyclo[2.1.0]pentanyl, bicyclo[2.2.0]hexanyl, bicyclo[3.1.0]hexanyl, bicyclo[3.2.0]heptanyl, and bicyclo[3.3.0]octanyl. The term "bicycloalkyl" also includes bridged bicycloalkyl systems such as, but not limited to, bicyclo[2.2.1]heptanyl and bicyclo[1.1.1]pentanyl.

The term "optionally substituted "$(C_3-C_8)$cycloalkyl" refers to a $(C_3-C_8)$cycloalkyl, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(\!=\!O)R^5)$, —$N(R^4)C(\!=\!O)$—$OR^5$, —$C(\!=\!O)$—$N(R^4)(R^5)$, —$C(\!=\!O)$—O—$N(R^4)(R^5)$, —$C(\!=\!O)$—$R^4$, —$C(\!=\!O)$—$OR^4$, and $(C_3-C_8)$cycloalkyl, in which $R^4$ and $R^5$ are each independently hydrogen or optionally substituted $(C_1-C_6)$ alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered) heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of to 8 ring atoms at least one of which is a heteroatom. A "(4- to 10-membered)heterocycloalkyl" means the heterocycloalkyl substituent contains a total of 4 to 10 ring atoms. A "(6-membered)heterocycloalkyl" means the heterocycloalkyl substituent contains a total of 6 ring atoms at least one of which is a heteroatom. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). The heterocycloalkyl substituent may be attached to the pyrazolopyrimidine core of the compounds of the present invention via a nitrogen atom having the appropriate valence, or via any ring carbon atom. The heterocycloalkyl moiety may be optionally substituted with one or more substituents at a nitrogen atom having the appropriate valence, or at any available carbon atom.

Also included in the definition of "heterocycloalkyl" are heterocycloalkyls that are fused to a phenyl or naphthyl ring or to a heteroaryl ring such as, but not limited to, a pyridinyl ring or a pyrimidinyl ring.

Examples of heterocycloalkyl rings include, but are not limited to, azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octaohydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, tetrahydrodiazinyl, oxazinyl, oxathiazinyl, quinuclidinyl, chromanyl, isochromanyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo [4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2 pyrazolidin-2-yl, 1,2-tetrahydrothiazin-2-yl, 1,3-thiazinan-3-yl, 1,2-tetrahydrodiazin-2-yl, 1,3 tetrahydrodiazin-1-yl, 1,4-oxazin-4-yl, oxazolidinonyl, 2-oxo-piperidinyl (e.g., 2-oxo-piperidin-1-yl), and the like.

The term "optionally substituted heterocycloalkyl" [e.g., optionally substituted (4- to 10-membered)heterocycloalkyl] refers to a heterocycloalkyl, as defined above, in which one or more hydrogen atoms, where chemically permissible are replaced by a substituent selected from the group consisting of halogen, oxo, cyano, hydroxy, —SF$_5$, nitro, —N(R$^4$)(R$^5$), —N(R$^4$)(C(=O)R$^5$), —N(R$^4$)C(=O)—OR$^5$, —C(=O)—N(R$^4$)(R$^5$), —C(=O)—O—N(R$^4$)(R$^5$), —C(=O)—R$^4$, —C(=O)—OR$^4$, and (C$_3$-C$_8$) cycloalkyl, in which R$^4$ and R$^5$ are each independently hydrogen or optionally substituted (C$_1$-C$_6$)alkyl.

A "(C$_6$-C$_{10}$)aryl" refers to an all-carbon monocyclic or fused-ring polycyclic aromatic group having a conjugated pi-electron system containing from 6 to 10 carbon atoms, such as phenyl, or naphthyl.

The term "optionally substituted (C$_6$-C$_{10}$)aryl" refers to a (C$_6$-C$_{10}$)aryl, as defined above, in which one or more hydrogen atoms are replaced by a substituent selected from the group consisting of halogen, cyano, hydroxy, —SF$_5$, nitro, —N(R$^4$)(R$^5$), —N(R$^4$)(C(=O)R$^5$), —N(R$^4$)C(=O)—OR$^5$, —C(=O)—N(R$^4$)(R$^5$), —C(=O)—O—N(R$^4$)(R$^5$), —C(=O)—R$^4$, —C(=O)—OR$^4$, and (C$_3$-C$_8$) cycloalkyl, in which R$^4$ and R$^5$ are each independently hydrogen or optionally substituted (C$_1$-C$_6$)alkyl.

As used herein, the term "heteroaryl" refers to monocyclic or fused-ring polycyclic aromatic heterocyclic groups with one or more heteroatom ring members (ring-forming atoms) each independently selected from oxygen (O), sulfur (S) and nitrogen (N) in at least one ring. A "(5- to 14-membered) heteroaryl" ring refers to a heteroaryl ring having from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)heteroaryl" ring refers to a heteroaryl ring having from 5 to 10 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)heteroaryl" refers to a heteroaryl ring having from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)nitrogen-containing heteroaryl" refers to a heteroaryl ring having from 5 to 6 ring atoms in which all of the heteroatoms in the ring are nitrogen. A "(6-membered)nitrogen-containing heteroaryl" refers to a heteroaryl ring having 6 ring atoms in which all of the heteroatoms in the ring are nitrogen. A "(5-membered)heteroaryl" refers to a heteroaryl ring having 5 ring atoms in which at least one of the ring atoms is a heteroatom. A heteroaryl may be a single ring or 2 or 3 fused rings. Examples of heteroaryls include, but are not limited to, 6-membered ring substituents such as pyridinyl, pyrazinyl, pyrimidinyl and pyridazinyl; 5-membered heteroaryls such as triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, and pyrazolyl; 6/5-membered fused ring substituents such as indolyl, indazolyl, benzofuranyl, benzimidazolyl, benzothienyl, benzoxadiazolyl, benzothiazolyl, isobenzothiofuranyl, benzothiofuranyl, benzothiophenyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl (e.g., 5,6,7,8-tetrahydro[1,2,4]triazolo[1,5-a]pyridin-2-yl), and anthranilyl; and 6/6-membered fused ring substituents such as quinolinyl, isoquinolinyl, cinnolinyl, quinazolinyl, oxochromenyl, and 1,4-benzoxazinyl.

It is to be understood that the heteroaryl may be optionally fused to a cycloalkyl group, or to a heterocycloalkyl group, as defined herein.

The heteroaryl substituent may be attached to the pyrazolopyrimidine core of the compounds of the present invention via a nitrogen atom having the appropriate valence, or via any ring carbon atom. The heteroaryl moiety may be optionally substituted with one or more substituents at a nitrogen atom having the appropriate valence, or at any available carbon atom.

The terms "optionally substituted (5- to 14-membered) heteroaryl" and "optionally substituted (5- to 6-membered) heteroaryl" refer to a (5- to 14-membered)heteroaryl and a (5- to 6-membered)heteroaryl, as defined above, in which one or more hydrogen atoms are replaced, where chemically permissible, by a substituent selected from the group consisting of halogen, oxo, cyano, hydroxy, —SF$_5$, nitro, —N(R$^4$)(R$^5$), —N(R$^4$)(C(=O)R$^5$), —N(R$^4$)C(=O)—OR$^5$, —C(=O)—N(R$^4$)(R$^5$), —C(=O)—O—N(R$^4$)(R$^5$), —C(=O)—R$^4$, —C(=O)—OR$^4$, and (C$_3$-C$_8$)cycloalkyl, in which R$^4$ and R$^5$ are each independently hydrogen or optionally substituted (C$_1$-C$_6$)alkyl. The substituent can be attached to the heteroaryl moiety at any available carbon atom or to a heteroatom when the heteroatom is nitrogen having the appropriate valence.

"halo" or "halogen" as used herein, refers to a chlorine, fluorine, bromine, or iodine atom.

"hydroxy" or "hydroxyl" as used herein, means an —OH group.

"cyano" as used herein, means a —CN group, which also may be depicted:

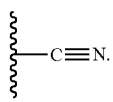

"nitro" as used herein, means an —NO$_2$ group.

"oxo" as used herein, means a ═O moiety. When an oxo is substituted on a carbon atom, they together form a carbonyl moiety [—C(═O)—]. When an oxo is substituted on a sulfur atom, they together form a sulfonyl moiety [—S(═O)—]; when two oxo groups are substituted on a sulfur atom, they together form a sulfonyl moiety [—S(═O) 2-].

"optionally substituted" as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —CH$_3$) is optionally substituted, then up to 3 hydrogen atoms on the carbon atom can be replaced with substituent groups.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms). For example, as shown in Formulas IA$^1$, and IA$^2$ below, R$^3$ may be bonded to any ring-forming atom of the pyrimidine ring that is substitutable.

"Therapeutically effective amount" refers to that amount of the compound being administered which will relieve to some extent one or more of the symptoms of the disorder being treated.

"Patient" refers to warm blooded animals such as, for example, pigs, cows, chickens, horses, guinea pigs, mice, rats, gerbils, cats, rabbits, dogs, monkeys, chimpanzees, and humans.

"Treating" or "treat", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Pharmaceutically acceptable" indicates that the substance or composition must be compatible, chemically and/or toxicologically, with the other ingredients comprising a formulation, and/or the mammal being treated therewith.

"Isoform" means any of several different forms of the same protein.

"Isozyme" or "isoenzyme" means a closely related variant of an enzyme that differs in amino acid sequence but catalyzes the same chemical reaction.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

This specification uses the terms "substituent," "radical," and "group" interchangeably.

If substituents are described as being "independently selected" from a group, each instance of a substituent is selected independent of the other. Each substituent therefore may be identical to or different from the other substituent(s).

As used herein the terms "Formula I", "Formula 1A$^1$", and "Formula 1A$^2$" may be hereinafter referred to as a "compound(s) of the invention." Such terms are also defined to include all forms of the compound of the invention including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

Some of the compounds of the invention have asymmetric carbon atoms. The carbon-carbon bonds of the compounds of the invention may be depicted herein using a solid line (——) a solid wedge (◥◣◣) or a dotted wedge (⋯⋯⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry are marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropoisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for mammalian consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylamino-ulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanol-amine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

Certain compounds of the invention may exist as geometric isomers. The compounds of the invention may possess one or more asymmetric centers, thus existing as two, or more, stereoisomeric forms. The present invention includes all the individual stereoisomers and geometric isomers of the compounds of the invention and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e., polymorphs, or they may exist as amorphous solids. All such forms are encompassed by the claims.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of the present invention with certain moieties known to those skilled in the art as "pro-moieties" as described, for example, in "Design of Prodrugs" by H. Bundgaard (Elsevier, 1985).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes all pharmaceutically acceptable isotopically-labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron emitting isotopes, such as $^{11}$C, $^{15}$F, $^{18}$F, $^{15}$O and $^{13}$N, can be useful in positron emission tomography (PET) studies for examining substrate receptor occupancy. Isotopically-labeled compounds of the present invention can generally be prepared by conventional techniques known to those skilled in the art or by processes analogous to those described in the accompanying Schemes and/or in the Examples and Preparations using an appropriate isotopically-labeled reagent in place of the non-labeled reagent previously employed. Pharmaceutically acceptable solvates in accordance with the invention include those wherein the solvent of crystallization may be isotopically substituted, e.g., D$_2$O, acetone-d$_6$, or DMSO-d$_6$. Compounds of the invention which includes compounds exemplified in Examples 1-97 described below, include isotopically-labeled versions of these compounds, such as, but not limited to, the deuterated and tritiated isotopes and all other isotopes discussed above.

Compounds

The compounds of Formula I, as described above, contain a pyrazolo[1,5-a]pyrimidine core wherein the core is substituted at the 3-position by an $R^1$ moiety, substituted at the 2-position by moiety A, and optionally substituted at the 5-, 6- or 7-position by an $R^3$ moiety. As described above, moiety A can be represented by a substituted amide ($A^1$) or a substituted reverse amide ($A^2$).

To further elucidate the compounds of Formula I wherein A is a substituted amide represented by Formula $A^1$, as depicted above, and m and n are both 0, the following subgenus of Formula IA$^1$, or a pharmaceutically acceptable salt thereof is described below:

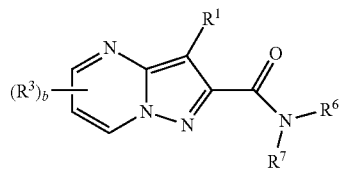

IA$^1$ wherein:

$R^1$ is selected from the group consisting of (C$_3$-C$_8$)cycloalkyl, (4- to 10-membered)-heterocycloalkyl, (C$_6$-C$_{10}$)aryl and (5- to 14-membered)heteroaryl, and, where chemically permissible, the (C$_3$-C$_8$)cycloalkyl, (4- to 10-membered)heterocycloalkyl, (C$_6$-C$_{10}$)aryl and (5- to 14-membered)heteroaryl moieties are optionally substituted with one to three $R^2$;

when present, each $R^2$ is independently selected from the group consisting of halogen, oxo, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C(=O)R$^5$), —C(=O)N(R$^4$)(R$^5$), —C(=O)—O—N(R$^4$)(R$^5$), —C(=O)—R$^4$, —C(=O)—OR$^4$, and optionally substituted (C$_3$-C$_8$)cycloalkyl;

when present, each $R^3$ is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C(=O)R$^5$), —C(=O)N(R$^4$)(R$^5$), —C(=O)—O—N(R$^4$)(R$^5$), —C(=O)—R$^4$, and —C(=O)—OR$^4$;

$R^4$ and $R^5$ are each independently selected from the group consisting of hydrogen, and optionally substituted (C$_1$-C$_6$) alkyl;

$R^6$ and $R^7$ are each independently selected from the group consisting of hydrogen, optionally substituted (C$_1$-C$_6$)alkyl, (C$_3$-C$_8$)cycloalkyl, (4- to 10-membered)heterocycloalkyl, (C$_6$-C$_{10}$)aryl, and (5- to 10-membered)heteroaryl, and where chemically permissible, the (C$_3$-C$_8$)cycloalkyl, -(4- to 10-membered)heterocycloalkyl, (C$_6$-C$_{10}$)aryl, and (5- to 10-membered)heteroaryl are optionally substituted with one to three $R^8$; or $R^6$ and $R^7$ taken together with the nitrogen to which they are attached form a (4- to 10-membered)heterocycloalkyl, and where chemically permissible, the (4- to 10-membered)-heterocycloalkyl is optionally substituted with one to three $R^9$;

when present each $R^8$ is independently selected from the group consisting of halogen, oxo, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C(=O)R$^5$), —C(=O)N(R$^4$)(R$^5$), —C(=O)—O—N(R$^4$)(R$^5$), —C(=O)—R$^4$, and —C(=O)—OR$^4$;

when present each $R^9$ is independently selected from the group consisting of halogen, oxo, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C(=O)R$^5$), —C(=O)N(R$^4$)(R$^5$), —C(=O)—O—N(R$^4$)(R$^5$), —C(=O)—R$^4$, and —C(=O)—OR$^4$; and b is represented by an integer selected from 0 or 1.

In certain embodiments of the present invention, in Formula IA$^1$, as depicted above, $R^1$ is selected from the group consisting of (C$_6$-C$_{10}$)aryl, wherein the aryl is phenyl; and (5- to 10-membered)heteroaryl; wherein the aryl and heteroaryl moieties are optionally substituted with one to three $R^2$, wherein each $R^2$ is independently selected from the group consisting of consisting of halogen, cyano, optionally substituted (C$_1$-C$_6$)alkyl, substituent independently and optionally substituted (C$_1$-C$_6$)alkoxy.

In certain embodiments, in Formula IA$^1$, as depicted above, $R^3$, $R^6$, $R^7$, $R^8$, $R^9$ and b are as immediately described above, and $R^1$ is a (C$_6$-C$_{10}$)aryl and the aryl is phenyl optionally substituted with one to three $R^2$, wherein each $R^2$ is independently selected from the group consisting of consisting of:
  i) halogen, wherein the halogen is fluoro or chloro;
  ii) cyano;
  iii) optionally substituted $(C_1-C_6)$alkyl, wherein the alkyl is methyl, ethyl or propyl, and the methyl, ethyl and propyl are optionally substituted with one or more flouro atoms;
  iv) optionally substituted $(C_1-C_6)$alkoxy, wherein the alkoxy is methoxy, ethoxy or propoxy and the methoxy, ethoxy and propoxy are optionally substituted with one or more fluoro atoms.

In certain embodiments, in Formula $IA^1$ as depicted above, $R^3$, $R^6$, $R^7$, $R^8$, $R^9$ and b are as immediately described above, and $R^1$ is a (5- to 10-membered)heteroaryl, wherein the heteroaryl is selected from the group consisting of pyridinyl, benzooxazolyl, and pyrazolopyrimidinyl and the pyridinyl, benzooxazolyl, and pyrazolopyrimidinyl moieties are optionally substituted with one to three $R^2$; wherein each $R^2$ is independently selected from the group consisting of consisting of:
  i) halogen, wherein the halogen is fluoro or chloro;
  ii) cyano;
  iii) optionally substituted $(C_1-C_6)$alkyl, wherein the alkyl is methyl, ethyl or propyl, and the methyl, ethyl and propyl are optionally substituted with one or more flouro atoms; and
  iv) optionally substituted $(C_1-C_6)$alkoxy, wherein the alkoxy is methoxy, ethoxy or propoxy and the methoxy, ethoxy and propoxy are optionally substituted with one or more fluoro atoms.

In certain other embodiments of the present invention, in Formula $IA^1$ as depicted above, $R^1$, $R^2$, $R^3$, and b are as described in any of the preceding embodiments, and $R^6$ and $R^7$ are each selected from the group consisting of optionally substituted $(C_1-C_8)$alkyl, $(C_3-C_8)$cycloalkyl, and (5- to 6-membered)heteroaryl, and where chemically permissible, the $(C_3-C_8)$cycloalkyl, and (5- to 6-membered)heteroaryl are optionally substituted with one to three $R^8$; or
$R^6$ and $R^7$ taken together with the nitrogen to which they are attached form a (4- to 6-membered)heterocycloalkyl, and where chemically permissible, the (4- to 6-membered)-heterocycloalkyl is optionally substituted with one to three $R^9$;
  when present each $R^8$ is independently selected from the group consisting of halogen, cyano, optionally substituted $(C_1-C_8)$alkyl, and optionally substituted $(C_1-C_8)$alkoxy; and
  when present each $R^9$ is independently selected from the group consisting of halogen, cyano, optionally substituted $(C_1-C_8)$alkyl, and optionally substituted $(C_1-C_8)$alkoxy.

In certain embodiments, in Formula $IA^1$ as depicted above, $R^1$, $R^2$, $R^3$ and b are as described in any of the preceding embodiments, and one of $R^6$ and $R^7$ is hydrogen and the other is selected from the group consisting of hydrogen, optionally substituted $(C_1-C_8)$alkyl, $(C_3-C_8)$cycloalkyl, and (5- to 6-membered)heteroaryl, and where chemically permissible, the $(C_3-C_8)$cycloalkyl, and (5- to 6-membered)heteroaryl are optionally substituted with one to three $R^8$; wherein each $R^8$ is independently selected from the group consisting of halogen, cyano, optionally substituted $(C_1-C_8)$alkyl, and optionally substituted $(C_1-C_8)$alkoxy.

In certain other embodiments, in Formula $IA^1$ as depicted above, $R^1$, $R^2$, $R^3$ and b are as described in any of the preceding embodiments, and one of $R^6$ and $R^7$ is hydrogen and the other is an optionally substituted $(C_1-C_8)$alkyl, wherein the $(C_1-C_8)$alkyl is selected from the group consisting of methyl, ethyl, and propyl.

In certain embodiments, in Formula $IA^1$ as depicted above, $R^1$, $R^2$, $R^3$ and b are as described in any of the preceding embodiments, and one of $R^6$ and $R^7$ is hydrogen and the other is a $(C_3-C_8)$cycloalkyl, wherein the $(C_3-C_8)$ cycloalkyl is selected from the group consisting of cyclopropyl, cyclobutyl, and cyclopentyl, and the cycloporopyl, cyclobutyl, and cyclopentyl are optionally substituted with one to three $R^8$; wherein each $R^8$ is independently selected from the group consisting of halogen, cyano, optionally substituted $(C_1-C_8)$alkyl, and optionally substituted $(C_1-C_8)$ alkoxy.

In certain embodiments, in Formula $IA^1$ as depicted above, $R^1$, $R^2$, and $R^3$ and b are as described in any of the preceding embodiments, and one of $R^6$ and $R^7$ is hydrogen and the other is a (5- to 6-membered)heteroaryl, wherein the (5- to 6-membered)heteroaryl is selected from the group consisting of pyridinyl and pyrimidinyl, and, where chemically permissible, the pyridinyl and pyrimidinyl are optionally substituted with one to three $R^8$; wherein each $R^8$ is independently selected from the group consisting of halogen, cyano, optionally substituted $(C_1-C_6)$alkyl, and optionally substituted $(C_1-C_6)$alkoxy.

In certain embodiments, in Formula $IA^1$ as depicted above, $R^1$, $R^2$, $R^3$ and b are as described in any of the preceding embodiments, and $R^6$ and $R^7$ taken together with the nitrogen to which they are attached form a (4- to 6-membered)heterocycloalkyl wherein the heterocycloalkyl is azetidinyl, and where chemically permissible, the azetidinyl is optionally substituted with one to three $R^9$, wherein each $R^9$ is independently selected from the group consisting of halogen, cyano, optionally substituted $(C_1-C_6)$alkyl, and optionally substituted $(C_1-C_6)$alkoxy.

In certain embodiments, in Formula $IA^1$ as depicted above, $R^1$, $R^2$, $R^4$, $R^5$, $R^6$, $R^7$, $R^8$, and $R^9$ are as described in any of the preceeding embodiments, b is 1, and $R^3$ is a halogen, wherein the halogen is a fluoro atom.

In certain embodiments, in Formula $IA^1$ as depicted above, $R^1$, $R^2$, $R^4$, $R^5$, $R^6$, $R^7$, $R^8$, and $R^9$ are as described in any of the preceeding embodiments, and b is 0.

To further elucidate the compounds of the present invention wherein A is a substituted amide represented by Formula $A^2$, as depicted above, and m and n are both 0, the following subgenus of Formula $IA^2$, or a pharmaceutically acceptable salt thereof is described below:

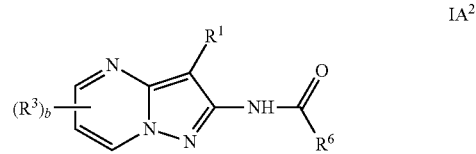

wherein:
$R^1$ is selected from the group consisting of $(C_3-C_8)$ cycloalkyl, (4- to 10-membered)-heterocycloalkyl, $(C_6-C_{10})$ aryl and (5- to 14-membered)heteroaryl, and, where chemically permissible, the $(C_3-C_8)$cycloalkyl, (4- to 10-membered) heterocycloalkyl, $(C_6-C_{10})$aryl and (5- to 14-membered)heteroaryl moieties are optionally substituted with one to three $R^2$;
  when present, each $R^2$ is independently selected from the group consisting of halogen, oxo, cyano, hydroxy, —$SF_5$, nitro, optionally substituted $(C_1-C_6)$alkyl, optionally substituted ($C_2$-$C_6$)alkenyl, optionally substituted ($C_2$-$C_6$)alkynyl, optionally substituted ($C_1$-$C_6$)alkylthio, optionally substituted ($C_1$-$C_6$)alkoxy, —N($R^4$)($R^5$), —N($R^4$)(C(=O)$R^5$), —C(=O)N($R^4$)($R^5$), —C(=O)—O—N($R^4$)($R^5$), —C(=O)—$R^4$, —C(=O)—O$R^4$, and optionally substituted ($C_3$-$C_8$)cycloalkyl;

when present, each $R^3$ is independently selected from the group consisting of halogen, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkylthio, optionally substituted ($C_1$-$C_6$)alkoxy, —N($R^4$)($R^5$), —N($R^4$)(C(=O)$R^5$), —C(=O)N($R^4$)($R^5$), —C(=O)—O—N($R^4$)($R^5$), —C(=O)—$R^4$ and —C(=O)—O$R^4$;

$R^4$ and $R^5$ are each represented by a substituent independently selected from the group consisting of hydrogen, and optionally substituted ($C_1$-$C_6$)alkyl;

$R^6$ is represented by a substituent independently selected from the group consisting of hydrogen, optionally substituted ($C_1$-$C_6$)alkyl, ($C_3$-$C_8$)cycloalkyl, (4- to 10-membered) heterocycloalkyl, ($C_6$-$C_{10}$)aryl, and (5- to 10-membered) heteroaryl, and where chemically permissible, the ($C_3$-$C_8$) cycloalkyl, -(4- to 10-membered)heterocycloalkyl, ($C_6$-$C_{10}$) aryl, and (5- to 10-membered)heteroaryl are optionally substituted with one to three $R^8$;

each $R^8$ is independently selected from the group consisting of halogen, oxo, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkylthio, optionally substituted ($C_1$-$C_6$) alkoxy, —N($R^4$)($R^5$), —N($R^4$)(C(=O)$R^5$), —C(=O)N($R^4$) ($R^5$), —C(=O)—O—N($R^4$)($R^5$), —C(=O)—$R^4$ and —C(=O)—O$R^4$; and b is represented by an integer selected from 0 or 1.

In certain embodiments of the present invention, in Formula IA$^2$, as depicted above, $R^1$ is selected from the group consisting of ($C_6$-$C_{10}$)aryl, wherein the aryl is phenyl; and (5- to 10-membered)heteroaryl; wherein the aryl and heteroaryl moieties are optionally substituted with one to three $R^2$, wherein each $R^2$ is independently selected from the group consisting of consisting of halogen, cyano, optionally substituted ($C_1$-$C_6$)alkyl, substituent independently and optionally substituted ($C_1$-$C_6$)alkoxy.

In certain embodiments, in Formula IA$^2$, as depicted above, $R^3$, $R^6$, $R^8$, and b are as immediately described above, and $R^1$ is a ($C_6$-$C_{10}$)aryl and the aryl is phenyl optionally substituted with one to three $R^2$, wherein each $R^2$ is independently selected from the group consisting of consisting of:

i) halogen, wherein the halogen is fluoro or chloro;
ii) cyano;
iii) optionally substituted ($C_1$-$C_6$)alkyl, wherein the alkyl is methyl, ethyl or propyl, and the methyl, ethyl and propyl are optionally substituted with one or more flouro atoms;
iv) optionally substituted ($C_1$-$C_6$)alkoxy, wherein the alkoxy is methoxy, ethoxy or propoxy and the methoxy, ethoxy and propoxy are optionally substituted with one or more fluoro atoms.

In certain embodiments, in Formula IA$^2$ as depicted above, $R^3$, $R^6$, $R^8$, and b are as immediately described above, and $R^1$ is a (5- to 10-membered)heteroaryl, wherein the heteroaryl is selected from the group consisting of pyridinyl, benzooxazolyl, and pyrazolopyrimidinyl and the pyridinyl, benzooxazolyl, and pyrazolopyrimidinyl moieties are optionally substituted with one to three $R^2$; wherein each $R^2$ is independently selected from the group consisting of consisting of:

i) halogen, wherein the halogen is fluoro or chloro;
ii) cyano;
iii) optionally substituted ($C_1$-$C_6$)alkyl, wherein the alkyl is methyl, ethyl or propyl, and the methyl, ethyl and propyl are optionally substituted with one or more flouro atoms; and
iv) optionally substituted ($C_1$-$C_6$)alkoxy, wherein the alkoxy is methoxy, ethoxy or propoxy, and the methoxy, ethoxy and propoxy are optionally substituted with one or more fluoro atoms.

In certain other embodiments of the present invention, in Formula IA$^2$ as depicted above, $R^1$, $R^2$, $R^3$, and b are as described in any of the preceeding embodiments, and $R^6$ is selected from the group consisting of optionally substituted ($C_1$-$C_6$)alkyl, ($C_3$-$C_8$)cycloalkyl, and (5- to 6-membered) heteroaryl, and where chemically permissible, the ($C_3$-$C_8$) cycloalkyl, and (5- to 6-membered)heteroaryl are optionally substituted with one to three $R^8$; when present each $R^8$ is independently selected from the group consisting of halogen, cyano, optionally substituted ($C_1$-$C_6$)alkyl, and optionally substituted ($C_1$-$C_6$)alkoxy.

In certain embodiments, in Formula IA$^2$ as depicted above, $R^1$, $R^2$, $R^3$ and b are as described in any of the preceeding embodiments, and $R^6$ is an optionally substituted ($C_1$-$C_6$)alkyl optionally substituted with one to three $R^8$; wherein each $R^8$ is independently selected from the group consisting of halogen, cyano, and optionally substituted ($C_1$-$C_6$)alkoxy.

In certain other embodiments, in Formula IA$^2$ as depicted above, $R^1$, $R^2$, $R^3$ and b are as described in any of the preceeding embodiments, and $R^6$ is an optionally substituted ($C_1$-$C_6$)alkyl, wherein the ($C_1$-$C_6$)alkyl is selected from the group consisting of methyl, ethyl, and propyl.

In certain embodiments, in Formula IA$^2$ as depicted above, $R^1$, $R^2$, $R^3$ and b are as described in any of the preceeding embodiments, and $R^6$ is a ($C_3$-$C_8$)cycloalkyl, wherein the ($C_3$-$C_8$)cycloalkyl is selected from the group consisting of cyloporopyl, cyclobutyl, and cyclopentyl, and the cyloporopyl, cyclobutyl, and cyclopentyl are optionally substituted with one to three $R^8$; wherein each $R^8$ is independently selected from the group consisting of halogen, cyano, optionally substituted ($C_1$-$C_6$)alkyl, and optionally substituted ($C_1$-$C_6$)alkoxy.

In certain embodiments, in Formula IA$^2$ as depicted above, $R^1$, $R^2$, and $R^3$ and b are as described in any of the preceding embodiments, and $R^6$ is a (5- to 6-membered) heteroaryl, wherein the (5- to 6-membered)heteroaryl is selected from the group consisting of pyridinyl and pyrimidinyl, and, where chemically permissible, the pyridinyl and pyrimidinyl are optionally substituted with one to three $R^8$; wherein each $R^8$ is independently selected from the group consisting of halogen, cyano, optionally substituted ($C_1$-$C_6$) alkyl, and optionally substituted ($C_1$-$C_6$)alkoxy.

In certain embodiments, in Formula IA$^2$ as depicted above, $R^1$, $R^2$, $R^4$, $R^5$, $R^6$, and $R^8$ are as described in any of the preceeding embodiments, b is 1, and $R^3$ is a halogen, wherein the halogen is a fluoro atom.

In certain embodiments, in Formula IA$^2$ as depicted above, $R^1$, $R^2$, $R^4$, $R^5$, $R^6$, and $R^8$ are as described in any of the preceeding embodiments, and b is 0.

In another embodiment, selected compounds of the present invention may be useful for treating a PDE4B-mediated disorder, comprising administering to a mammal (preferably a human) in need thereof a therapeutically effective amount of a compound of the invention effective in inhibiting PDE4B activity; more preferably, administering an amount of a compound of the invention having improved binding affinity for PDE4B while at the same time possessing less inhibitory activity toward PDE4D.

In certain other embodiments, selected compounds of the present invention may exhibit a binding affinity for the PDE4B isoform.

In certain embodiments, the compounds of the present invention have an enhanced binding affinity for the PDE4B isoform over the PDE4D isoform such that the compounds display about a 2-fold to about a 200-fold binding affinity for the PDE4B isoform over the PDE4D isoform. In certain other embodiments, the compounds of the present invention display about a 10-fold to about a 50-fold binding affinity for the PDE4B isoform over the PDE4D isoform. In certain other embodiments, the compounds of the present invention display about a 51-fold to about a 100-fold binding affinity for the PDE4B isoform over the PDE4D isoform. In certain other embodiments, the compounds of the present invention display about a 101-fold to about a 200-fold binding affinity for the PDE4B isoform over the PDE4D isoform. In certain embodiments, the compounds of the present invention display at least about a 2-fold binding affinity for the PDE4B isoform over the PDE4D isoform. In certain embodiments, the compounds of the present invention display at least about a 5-fold binding affinity for the PDE4B isoform over the PDE4D isoform. In certain embodiments, the compounds of the present invention display at least about a 10-fold binding affinity for the PDE4B isoform over the PDE4D isoform. In certain embodiments, the compounds of the present invention display at least about a 20-fold binding affinity for the PDE4B isoform over the PDE4D isoform. In certain other embodiments, the compounds of the present invention display at least about a 40-fold binding affinity for the PDE4B isoform over the PDE4D isoform. In certain other embodiments, the compounds of the present invention display at least about a 50-fold binding affinity for the PDE4B isoform over the PDE4D isoform. In certain other embodiments, the compounds of the present invention display at least about a 75-fold binding affinity for the PDE4B isoform over the PDE4D isoform. In certain other embodiments, the compounds of the present invention display at least about a 100-fold binding affinity for the PDE4B isoform over the PDE4D isoform. In certain other embodiments, the compounds of the present invention display at least about a 200-fold binding affinity for the PDE4B isoform over the PDE4D isoform. The binding affinities of the compounds of the present invention for the PDE4B and PDE4D isoforms are shown in Table 3 of the Experimental Section below.

In another embodiment, the present invention provides a pharmaceutical composition comprising a compound of the present invention, or a pharmaceutically acceptable salt thereof, in admixture with at least one pharmaceutically acceptable excipient.

In yet another embodiment, administration of the compounds of the present invention to a patient in need thereof may also lead to a decrease in gastrointestinal discomfort such as emesis, diarrhea, and nausea, which is currently believed to be associated with administration of compounds having binding affinity for other PDE4 isoforms, especially the PDE4D isoform, resulting in an increase in patient compliance as well as overall treatment outcome.

In another embodiment, the present invention provides a method of treating central nervous system (CNS), neuroinflammatory, metabolic, autoimmune and inflammatory diseases or disorders comprising administering to the mammal, particularly a human, in need of such treatment a therapeutically effect amount of a compound of the present invention, or a pharmaceutically acceptable salt thereof.

In another embodiment, the present invention provides the use of a compound of the present invention, or a pharmaceutically acceptable salt thereof, in the manufacture of a medicament for treating central nervous system (CNS), neuroinflammatory, autoimmune and inflammatory diseases or disorders.

Pharmacology

Phosphodiesterases (PDEs) of the PDE4 family are characterized by selective, high-affinity hydrolytic degradation of the second messenger cyclic nucleotide, adenosine 3',5'-cyclic monophosphate (cAMP). The PDE4A, PDE4B and PDE4D subtypes are known to be widely expressed throughout the brain, with regional and intracellular distribution for the PDE4A, PDE4B and PDE4D subtypes being distinct, whereas the PDE4C subtype is expressed at lower levels throughout the central nervous system (See; Siuciak, J. A. et al., *Antipsychotic profile of rolipram: efficacy in rats and reduced sensitivity in mice deficient in the phosphodiesterase-4B (PDE4B) enzyme*, Psychopharmacology (2007) 192:415-424). The location of the PDE4 subtypes makes them an interesting target for exploring new treatments for central nervous system diseases and disorders. For example, PDE4B has been identified as a genetic susceptibility factor for schizophrenia (See: Millar, J. K. et al., *Disrupted in schizophrenia 1 and phosphodiesterase 4B: towards an understanding of psychiatric illness*, J. Physiol. 584 (2007) pp. 401-405).

The PDE4 inhibitor rolipram has been shown to be useful in treating or reversing Aβ-induced memory deficits via the attenuation of neuronal inflammation and apoptosis-mediated cAMP/CREB signaling, and is a potential target for treatment of cognitive deficits associated with AD. (See: Wang, C. et al., *The phosphodiesterase-4 inhibitor rolipram reverses Aβ-induced cognitive impairment and neuroinflammatory and apoptotic responses in rats*, International Journal of Neuropsychopharmacology (2012), 15, 749-766).

PDE4 inhibitors have also been shown to possess antidepressant effects by decreasing brain levels of PDE4 in individuals with major depressive disorder (MDD) (See: Fujita, M. et al., *C-(R)-Rolipram Positron Emission Tomography in Major Depressive Disorder*, Biological Psychiatry, 71, 2012, 548-554).

Furthermore, PDE4 inhibitors have been shown to possess therapeutic activity with implications for the treatment of multiple sclerosis (See: Sun, X. et al., *Rolipram promotes remyelination possibly via MEK-ERK signal pathway in cuprizone-induced demyelination mouse*, Experimental Neurology 2012; 237:304-311).

In view of the above, in certain embodiments, the compounds of the present invention have a wide range of therapeutic applications for the treatment of conditions or diseases of the central nervous system which include neurologic, neurodegenerative and/or psychiatric disorders. Neurologic, neurodegenerative and/or psychiatric disorders, include but are not limited to, (1) mood [affective] disorders; (2) neurotic, stress-related and somatoform disorders including anxiety disorders; (3) disorders comprising the symptom of cognitive deficiency in a mammal, including a human; (4) disorders comprising attention deficits, executive function deficits (working memory deficits), dysfunction of impulse control, extrapyramidal symptoms, disorders that are based on a malfunction of basal ganglia; (5) behavioral and emotional disorders with onset usually occurring in childhood and adolescence; (6) disorders of psychological development; (7) systemic atrophies primarily affecting the central nervous system; (8) extrapyramidal and movement disorders; (9) behavioral syndromes associated with physiological disturbances and physical factors; (10) disorders of adult personality and behavior; (11) schizophrenia and other psychotic disorders; (12) mental and behavioral disorders due to psychoactive substance use; (13) sexual dysfunction comprising excessive sexual drive; (14) mental retardation; (15) factitious disorders, e.g., acute hallucinatory mania; (16) episodic and paroxysmal disorders, epilepsy; (17) narcolepsy; (18) dementia.

Examples of mood [affective] disorders that can be treated according to the present invention include, but are not limited to, bipolar disorder I, hypomania (manic and mixed form), bipolar disorder II; depressive disorders such as single depressive episode or recurrent major depressive disorder, chronic depression, psychotic depression, minor depressive disorder, depressive disorder with postpartum onset, depressive disorders with psychotic symptoms; persistent mood [affective] disorders such as cyclothymia, dysthymia, euthymia; premenstrual syndrome (PMS) and premenstrual dysphoric disorder.

Examples of neurotic, stress-related and somatoform disorders that can be treated according to the present invention include, but are not limited to, anxiety disorders, social anxiety disorder, general anxiety disorder, panic disorder with or without agoraphobia, specific phobia, social phobia, chronic anxiety disorders; obsessive compulsive disorder; reaction to sever stress and adjustment disorders, such as post traumatic stress disorder (PTSD), acute stress disorder; other neurotic disorders such as depersonalization-derealization syndrome.

The phrase "cognitive deficiency" as used here in "disorder comprising as a symptom cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of disorders comprising as a symptom cognitive deficiency that can be treated according to the present invention include, but are not limited to, cognitive deficits primarily but not exclusively related to amnesia, psychosis (schizophrenia), Parkinson's disease, Alzheimer's disease, multi infarct dementia, senile dementia, Lewis body dementia, stroke, frontotemporal dementia, progressive supranuclear palsy, Huntington's disease, HIV disease (HIV-associated dementia), cerebral trauma and drug abuse; mild cognitive disorder ADHD, Asperger's syndrome, and age-associated memory impairment.

Examples of disorders usually first diagnosed in infancy, childhood and adolescence that can be treated according to the present invention include, but are not limited to, hyperkinetic disorders including disturbance of activity and attention, attention deficit/hyperactivity disorder (ADHD), hyperkinetic conduct disorder; attention deficit disorder (ADD); conduct disorders, including but not limited to depressive conduct disorder; tic disorders including transient tic disorder, chronic motor or vocal tic disorder, combined vocal and multiple motor tic disorder (Gilles de la Tourette's syndrome), substance induced tic disorders; autistic disorders; Batten disease, excessive masturbation nail-biting, nose-picking and thumb-sucking.

Examples of disorders of psychological development that can be treated according to the present invention include, but are not limited to pervasive developmental disorders, including but not limited to Asperger's syndrome and Rett syndrome, autistic disorders, childhood autism and overactive disorder associated with mental retardation and stereotyped movements, specific developmental disorder of motor function, specific developmental disorders of scholastic skills.

Examples of systemic atrophies primarily affecting the central nervous system that can be treated according to the present invention include, but are not limited to, multiple sclerosis systemic atrophies primarily affecting the basal ganglia including Huntington's disease, and amyotrophic lateral sclerosis.

Examples of extrapyramidal and movement disorders with malfunction and/or degeneration of basal ganglia that can be treated according to the present invention include, but are not limited to, Parkinson's disease; second Parkinsonism such as postencephalitic Parkinsonism; Parkinsonism comprised in other disorders; Niemann-Pick disease, Lewy body disease; degenerative diseases of the basal ganglia; other extrapyramidal and movement disorders including tremor, essential tremor and drug-induced tremor, myoclonus, chorea and drug-induced chorea, drug-induced tics and tics of organic origin, drug-induced acute dystonia, drug-induced tardive dyskinesia, muscular spasms and disorders associated with muscular spasticity or weakness including tremors; mental deficiency (including spasticity, Down syndrome and fragile X syndrome) L-dopa-induced dyskinesia; restless leg syndrome Stiff-man syndrome.

Further examples of movement disorders with malfunction and/or degeneration of basal ganglia that can be treated according to the present invention include, but are not limited to, dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), oromandibular dystonia and spasmodic dysphonia (cramp of the vocal cord); neuroleptic-induced movement disorders including but not limited to neuroleptic malignant syndrome (NMS), neuroleptic induced parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor.

Examples of behavioral syndromes associated with physiological disturbances and physical factors according to the present invention include, but are not limited to nonorganic sleep disorders, including but not limited to nonorganic hypersomnia, nonorganic disorder of the sleep-wake schedule (circadian rhythm sleep disorder), insomnia, parasomnia and sleep deprivation; mental and behavioral disorders associated with the puerperium including postnatal and postpartum depression; eating disorders, including but not limited to anorexia nervosa, bulimia nervosa, binge eating disorder, hyperphagia, obesity, compulsive eating disorders and pagophagia.

Examples of disorders of adult personality and behavior that can be treated according to the present invention include, but are not limited to, personality disorders, including but not limited to emotionally unstable, borderline, obsessive-compulsive, anankastic, dependent and passive-aggressive personality disorder; habit and impulse disorders (impulse-control disorder) including intermittent explosive disorder, pathological gambling, pathological fire-setting (pyromania), pathological stealing (kleptomania), trichotillomania; Munchausen syndrome.

Examples of schizophrenia and other psychotic disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis.

Examples of mental and behavioral disorders due to psychoactive substance use that can be treated according to the present invention include, but are not limited to, mental and behavioral disorders due to use of alcohol, opioids, cannabinoids, sedatives or hypnotics, cocaine; mental and behavioral disorders due to the use of other stimulants including caffeine, mental and behavioral disorders due to drug dependence and abuse (e.g., narcotic dependence, alcoholism, amphetamine and methamphetamine dependence, opioid dependence, cocaine addiction, nicotine dependence, and drug withdrawal syndrome, and relapse prevention), use of hallucinogens, tobacco (nicotine), volatile solvents and mental and behavioral disorders due to multiple drug use and use of other psychoactive substances including the following subtype symptoms: harmful use, dependence syndrome, withdrawal state, and withdrawal state with delirium.

Examples of dementia that can be treated according to the present invention include, but are not limited to, vascular dementia, dementia due to Creutzfeld-Jacob disease, HIV, head trauma, Parkinson's, Huntington's, Pick's disease, dementia of the Alzheimer's type.

In certain embodiments, the present invention is directed to methods for the treatment of schizophrenia by administration of a therapeutically effective amount of a compound of the present invention to a patient in need thereof.

In certain other embodiments, the invention is further directed to a method for the treatment of cognitive impairment associated with schizophrenia by administration of a therapeutically effective amount of a compound of the present invention to a patient in need thereof.

In addition to the central nervous system disorders mentioned above, there is extensive literature in the art describing the effects of PDE inhibitors on various autoimmune and inflammatory cell responses, which in addition to cAMP increase, include inhibition of superoxide production, degranulation, chemotaxis and tumor necrosis factor (TNF) release in eosinophils, neutrophils and monocytes. Therefore, the compounds of the present invention may be useful for treating autoimmune and Inflammatory diseases. (See: Schett, G. et al., *Apremilast: A novel PDE4 Inhibitor in the Treatment of Autoimmune and Inflammatory Diseases*, Ther. Adv. Musculoskeletal Dis. 2010; 2(5):271-278). For example, the compounds of the present invention may be useful for treatment of oral ulcers associated with Behçet's disease (Id.). The compounds of the present invention may also be useful for the treatment of pain associated with arthritis (See: Hess, A. et al., *Blockade of TNF-α rapidly inhibits pain responses in the central nervous system*, PNAS, vol. 108, no. 9, 3731-3736 (2011) or for the treatment of psoriasis or psoriatic arthritis (See: Schafer, P., *Apremilast mechanism of action and application to psoriasis and psoriatic arthritis*, Biochem. Pharmacol. (2012), 15; 83(12): 1583-90). Accordingly, compounds of the present invention may also be useful for treatment of ankylosing spondylitis [see: Patan, E. et al., *Efficacy and safety of apremilast, an oral phosphodiesterase 4 inhibitor, in ankylosing spondylitis*, Ann. Rheum. Dis. (Sep. 14, 2102)]. Other conditions treatable by administration of the compounds of the present invention include, but are not limited to, acute and chronic airway diseases such as, but not limited to, asthma, chronic or acute bronchoconstriction, chronic bronchitis, bronchiectasis, small airways obstruction, emphysema, obstructive or inflammatory airways diseases, acute respiratory distress syndrome (ARDS), COPD, pneumoconiosis, seasonal allergic rhinitis or perennial allergic rhinitis or sinusitis, and acute lung injury (ALI)

In yet another embodiment, the compounds of the present invention may be useful for treating rheumatoid arthritis, gout, and fever, edema and pain associated with inflammation, eosinophil-related disorders, dermatitis or eczema, urticaria, conjunctivitis, uveitis, psoriasis, inflammatory bowel disease, sepsis, septic shock, liver injury, pulmonary hypertension, pulmonary edema, bone loss disease, and infection.

In yet another embodiment, the compounds of the present invention may be useful for treating cancer. For example, the compounds of the present invention may be useful for treatment of brain cancer (e.g., medulloblastoma) (See: Schmidt, A. L., *BDNF and PDE4, but not GRPR, Regulate Viability of Human Medulloblastoma Cells*, J. Mol. Neuroscience (2010) 40:303-310). The compounds of the present invention may also be useful for treating melanoma (See: Marquette, A. et al., *ERK and PDE4 cooperate to induce RAF isoform switching in melanoma*, Nature Structural & Molecular Biology, vol. 18, no. 5, 584-91, 2011). In certain embodiments, the compounds of the present invention may be useful for treating leukemia, e.g., chronic lymphocytic leukemia, (See: Kim, D. H. et al., *Type 4 Cyclic Adenosine Monophosphate Phosphodiesterase as a Therapeutic Target in Chronic Lymphocytic Leulemia*, Blood Journal of The American Society of Hematology, Oct. 1, 1998, vol. 92, no. 7 2484-2494).

In certain other embodiments, the compounds of the present invention may be useful for treating diabetes or diseases associated with diabetes (See: Vollert, S. et al., *The glucose-lowering effects of the PDE4 inhibitors roflumilast and roflumilast-N-Oxide in db/db mice*, Diabetologia (2012) 55:2779-2788. Wouters, E. F. M. et al., *Effect of the Phosphodiesterase 4 Inhibitor Roflumilast on Glucose Metabolism in Patients with Treatment-Naïve, Newly Diagnosed Type 2 Diabetes Mellitus*, Journal of Clinical Endocrinology and Metabolism 2012, 97, 1720-1725). Other examples include, but are not limited to, diabetic macular degeneration, diabetic neuropathy, obesity, type 2 diabetes (non-insulin dependent diabetes), metabolic syndrome, glucose intolerance, urinary incontinence (e.g., bladder overactivity), diabetic macular edema, nephropathy and related health risks, symptoms or disorders. As such, the compounds can also be used to reduce body fat or body weight of an overweight or obese individual.

In certain other embodiments, the compounds of the present invention may be useful in the prevention and treatment of disorders associated with enhanced endothelial activity, impaired endothelial barrier function and/or enhanced neoangiogenesis, such as septic shock; angioedema, peripheral edema, communicating or non-communicating hydrocepahuls, vascular edema, cerebral edema; reduced natriuria pathology; inflammatory diseases, including asthma, rhinitis, arthritis and rheumatoid diseases and autoimmune diseases; acute renal or liver failure, liver dysfunction; psoriasis, Irritable Bowel Disease (IBD), Crohn's disease, and benign/malignant neoplasia.

In certain other embodiments, the compounds of the present invention may be useful for treating diseases of the spinal cord and/or peripheral nervous system, including spinal cord injury, spinal cord edema, spinal cord tumors, vascular malformations or anomalies of the spinal cord, syringomyelia, hydromyelia.

In certain other embodiments, the compounds described herein are further useful in the prevention and treatment of disorders associated with thrombosis, embolism, or ischemic disorders including, but not limited to thrombosis induced tissue infarction in coronary artery disease, in cerebrovascular disease (including cerebral arteriosclerosis, cerebral amyloid angiopathy, hereditary cerebral hemorrhage, and brain hypoxia-ischemia) and/or in peripheral vascular disease; stable and unstable angina, transient ischemic attacks, stroke, atherosclerosis, myocardial infarct, cerebral infarct, reperfusion injury (brain/cardiac), traumatic brain injury, subdural, epidural or subarachnoid hemorrhage, migraine, cluster and tension headaches, placenta insufficiency thrombosis after surgical procedures, such as bypass, angioplasty, stent placement, heart valve replacement, cognitive decline or delirium post-operative or in association with intensive care therapy, brain or ophthalmologic tumors.

In certain other embodiments, the compounds described herein are further useful for treating pain conditions and disorders. Examples of such pain conditions and disorders include, but are not limited to, inflammatory pain, hyperalgesia, inflammatory hyperalgesia, migraine, cancer pain, osteoarthritis pain, post-surgical pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central post stroke pain, multiple sclerosis pain, Parkinson disease pain, and spinal cord injury pain.

In certain other embodiments, the compounds described herein are further useful for treating wounds or promoting wound healing, burns, scarring, and related conditions.

In certain other embodiments, the compounds described herein are further useful for treating neuronal damage disorders (including ocular damage, retinopathy including diabetic macular edema or macular degeneration of the eye, tinnitus, hearing impairment and loss, and brain edema).

In certain other embodiments, the compounds described herein are further useful for treating transplant rejection, allograft rejection, renal and liver failure, and restless leg syndrome.

Formulations

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically (e.g., intranasal or ophthalmic).

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents, and include depot formulations.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a PDE4 inhibitor compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as $A\beta_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis(4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SU LAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPOMEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxpine, resperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-3-fluoro-3-(3-fluoro-4-pyrrolidin-1-yl-methyl-phenyl)-cyclobutane carboxylic acid ethylamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-benzyloxy-5-((5-undecyl-2H-pyrrol-2-ylidene)methyl)-2,2'-bi-1H-pyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (I-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, viluzole 2,3,4,9-tetrahydro-1H-carbazol-3-one oxime, desmoteplase, anatibant, astaxanthin, neuropeptide NAP (e.g., AL-108 and AL-208; both Allon Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors;

(h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitor such as 2-[4-(1-Methyl-4-pyridin-4-yl-1H-pyrazol-3-yl)phenoxymethyl]quinoline (PF-2545920), and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, AcrER ($N^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A (5-$HT_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT2c) receptor agonists, such as vabicaserin, and zicronapine;

(xxxv) serotonin (5-hydroxytryptamine) 4 (5-$HT_4$) receptor agonists, such as PRX-03140 (Epix);

(xxxvi) serotonin (5-hydroxytryptamine) 6 (5-$HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydrofuran-3-yl}propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The compounds of the invention, or their pharmaceutically acceptable salts, may be prepared by a variety of methods that are analogously known in the art. The reaction Schemes described below, together with synthetic methods known in the art of organic chemistry, or modifications and derivatizations that are familiar to those of ordinary skill in the art, illustrate three (3) methods for preparing the compounds. Others, including modifications thereof, will be readily apparent to one skilled in the art.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2007, which are hereby incorporated by reference.

Compounds of the present invention or their pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Schemes 1 through 3 will be generated as a mixture of diastereomers and/or enantiomers; these may be separated at various stages of the synthetic Scheme using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Schemes are representative of methods useful in synthesizing the compounds of the present invention. They are not to constrain the scope of the invention in any way.

The compounds of the present invention may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of the invention, or tautomers thereof or pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Schemes 1 and 2 will be generated as a mixture of diastereomers and/or enantiomers; these may be separated at various stages of the synthetic schemes using conventional techniques or a combination of such techniques, such as, but not limited to, crystallization, normal phase chromatography, reversed phase chromatography and chiral chromatography, to afford the single stereoisomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 below illustrates general synthetic preparations of compounds represented by Formula I. The initial step of the synthesis as depicted, utilizes a compound of Formula AA as an initial starting material, wherein A' is an ester moiety or an amine moiety. An example of Formula AA when A' is an ester moiety has been described previously in the literature (PCT Int. Appl. 2008015271, PCT Int. Appl. 2008062739, *Bioorganic & Medicinal Chemistry Letters* 2009, 19, 4207-4209, PCT Int. Appl. 2010074284). An example of Formula AA where A' is an amine moiety has been described previously (PCT Int. Appl. 2011045344). In the first step, Formula AA is treated with an appropriately substituted 1,3-diketone (Formula B), protected 1,3-diketone (Formula C), or 1,3-diketone equivalent (Formula D) (PCT Int. Appl. 2010018481) and an acid catalyst in an appropriate solvent, from about room temperature to about 150° C., to form a compound of Formula E (pyrazolopyrimidine; b is an integer selected from 0, 1, 2, or 3). During this initial step, each $R^3$ substituent of Formulas B, C and D should be represented by the same moiety as desired in the final product or a protected variation thereof. For example, the final product of Example 1 each $R^3$ is hydrogen. R of Formula C is a lower alkyl.

In the next step, Formula E is halogenated at the unsubstituted position of the pyrazole ring by treatment with an electrophilic halogen reagent such as N-iodosuccinimide (NIS), N-bromosuccinimide (NBS), iodine monochloride (ICl), iodine (I$_2$), bromine (Br$_2$), etc. in an inert solvent, potentially acid-catalyzed, from about room temperature to about 100° C., to form the compound of Formula F (wherein X is a halogen selected from chlorine, iodine or bromine). The compound of Formula F is then converted into a compound of Formula I utilizing one of two synthetic pathways. In a first pathway, Formula F (halogenated pyrazolopyrimidine) undergoes a Suzuki-Miyaura reaction (*Chemical Society Reviews* 2014, 43, 412-443; *Accounts of Chemical Research* 2013, 46, 2626-2634) by treatment with an appropriate alkyl, aryl, or heteroaryl boronate in the presence of a base and a transition metal catalyst, potentially palladium acetate or tris(dibenzylideneacetone) dipalladium, a metal chelating ligand, in an appropriate solvent which installs the appropriate R$^1$ moiety to form a compound of Formula G. During this step, the R$^1$ moiety is represented by the same moiety as is desired in the final product. For example, the final product of Example 1 can be prepared wherein R$^1$ is represented by a chlorophenyl moiety.

In a next step, the compound of Formula G is then converted to the desired amide of Formula I through common functional group manipulations. For example, when A' is an ester, treatment with the appropriate amine (the amine moiety that makes up the amine portion of the amide that is desired in the final product. For example, the compound of Example 1 the desired amine is an azetidine ring) using heat and a Lewis acid, such as magnesium methoxide or calcium chloride, in an appropriate solvent (see *Tetrahedron Letters* 2010, 51, 3879-3882) converts A' to the amine of moiety A. Alternatively, the conversion of Formula G where A' is an ester to the desired amide of Formula I can be effected through a two step process in which the ester is first hydrolyzed to the acid, via acidic or basic treatment in water and a co-solvent; the acid is subsequently converted to the amide by treatment with the appropriate amine in the presence of an amide coupling/dehydrating reagent such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), 1,3-dicyclohexylcarbodiimide (DCC), etc., at temperatures ranging from about −20° C. to about 100° C. to afford compounds of Formula I. When A' is an amine (or protected amine), conversion of compound of Formula G to the desired Formula I goes through a deprotection (if needed) and then a substitution of the amine with the appropriately substituted acid through amine coupling/dehydrating reagents (see above), acid chloride, or with the appropriately substituted heterocycle through SNAr reaction conditions (see review: Organic Reaction Mechanisms (2012) Volume Date 2009, 215-228).

An alternative approach to generate compounds of Formula I can be done through a reversal of the manipulations of substituents A' and X that was done in the conversion of intermediate of Formula F to Formula I. Intermediate F, when A' is an ester, is converted to a compound of Formula H by the method described above for the conversion of Formula G to Formula I. The resulting Formula H may then be transformed through a Suzuki-Miyaura type reaction, previously described, with the appropriately substituted boronate to give the compound of Formula I.

When A' is an amine, intermediate Formula F can be converted to Formula H by deprotection (if needed) followed by amide coupling/dehydration conditions with an appropriately substituted acid or through an SNAr substitution with the appropriate heterocycle to provide Formula H. Intermediate compound of Formula H is then subjected to Suzuki-Miyaura reaction conditions to provide compounds of Formula I.

Scheme 1

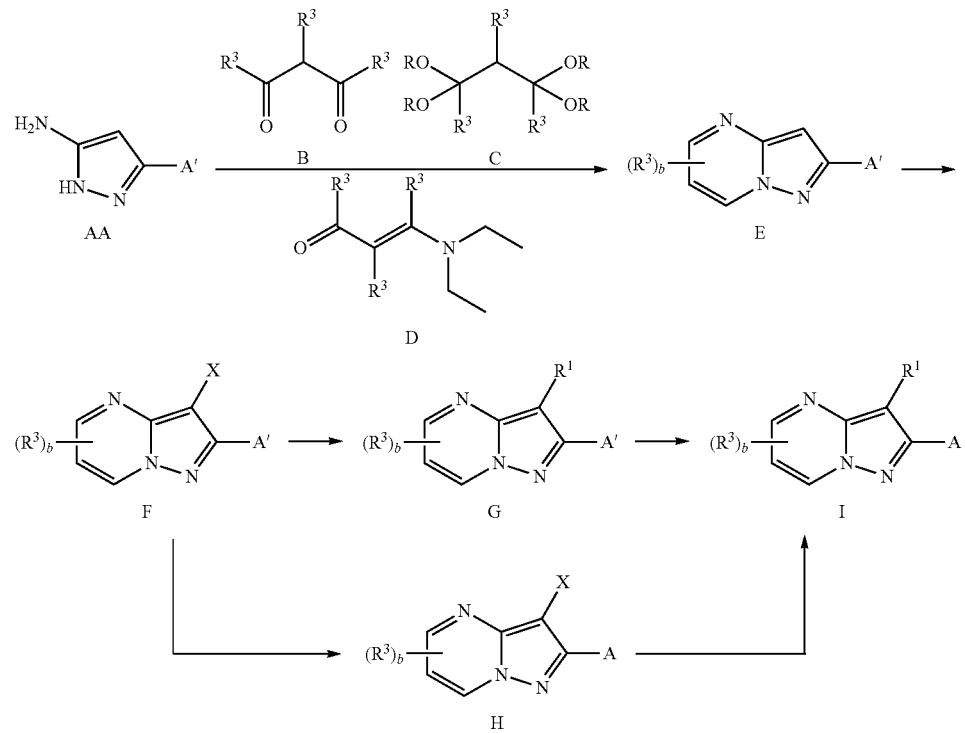

Scheme 2 illustrates synthetic preparations of compounds represented by Formula IA[1]. The preparation of a compound of Formula AA' where R is a lower alkyl has been described previously in the literature (PCT Int. Appl. 2008015271, PCT Int. Appl. 2008062739, *Bioorganic & Medicinal Chemistry Letters* 2009, 19, 4207-4209, PCT Int. Appl. 2010074284). In a first step, a compound of Formula AA' is treated with an appropriately substituted 1,3-diketone (Formula B), protected 1,3-diketone (Formula C), or 1,3-diketone equivalent (Formula D) (PCT Int. Appl. 2010018481) and an acid catalyst in an appropriate solvent, from about room temperature to about 150° C., to form a compound of Formula EE (pyrazolopyrimidine; b is an interger selected from 0, 1, 2, or 3, and R is a lower alkyl). During this initial step, each $R^3$ substituent of Formulas B, C and D should be represented by the same moiety as desired in the final product or a protected variation thereof. For example, the final product of Example 1 each $R^3$ is hydrogen. R of Formula C is a lower alkyl.

In the next step, Formula EE is halogenated at the unsubstituted position of the pyrazole ring by treatment with an electrophilic halogen reagent such as N-iodosuccinimide (NIS), N-bromosuccinimide (NBS), iodine monochloride (ICI), iodine ($I_2$), bromine ($Br_2$), etc. in an inert solvent, potentially acid-catalyzed, from about room temperature to about 100° C., to form the compound of Formula FF (wherein X is a halogen selected from chlorine, iodine or bromine). The compound of Formula FF is then converted into a compound of Formula IA[1] utilizing one of two synthetic pathways. In a first pathway, Formula FF (halogenated pyrazolopyrimidine) undergoes a Suzuki-Miyaura reaction (*Chemical Society Reviews* 2014, 43, 412-443; *Accounts of Chemical Research* 2013, 46, 2626-2634) by treatment with an appropriate alkyl, aryl, or heteroaryl boronate in the presence of a base and a transition metal catalyst, potentially palladium acetate or tris(dibenzylideneacetone) dipalladium, a metal chelating ligand, in an appropriate solvent which installs the appropriate $R^1$ moiety to form a compound of Formula GG. During this step, the $R^1$ moiety is represented by the same moiety as is desired in the final product, For example, the final product of Example 1 can be prepared wherein $R^1$ is represented by a chlorophenyl moiety.

In a next step, the compound of Formula GG is then converted to the desired amide of Formula IA[1] through treatment of the ester with the appropriate amine (the amine moiety that makes up the amine portion of the amide that is desired in the final product. For example, the compound of Example 1 the desired amine is an azetidine ring) using heat and a Lewis acid, such as magnesium methoxide or calcium chloride, in an appropriate solvent (see *Tetrahedron Letters* 2010, 51, 3879-3882). Alternatively, the conversion of Formula GG to the desired amide of Formula I can be effected through a two step process in which the ester is first hydrolyzed to the acid, via acidic or basic treatment in water and a co-solvent; the acid is subsequently converted to the amide by treatment with the appropriate amine in the presence of an amide coupling/dehydrating reagent such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), 1,3-dicyclohexylcarbodiimide (DCC), etc., at temperatures ranging from about −20° C. to about 100° C. to afford compounds of Formula IA[1]. An alternative approach to generate compounds of Formula IA[1] from intermediate of Formula FF is by first converting the ester of Formula FF to the compound of Formula HH by the method described above for the conversion of Formula GG to Formula IA[1] The resulting Formula HH may then be transformed through a Suzuki-Miyaura type reaction, previously described, with the appropriately substituted boronate to give the compound of Formula IA[1].

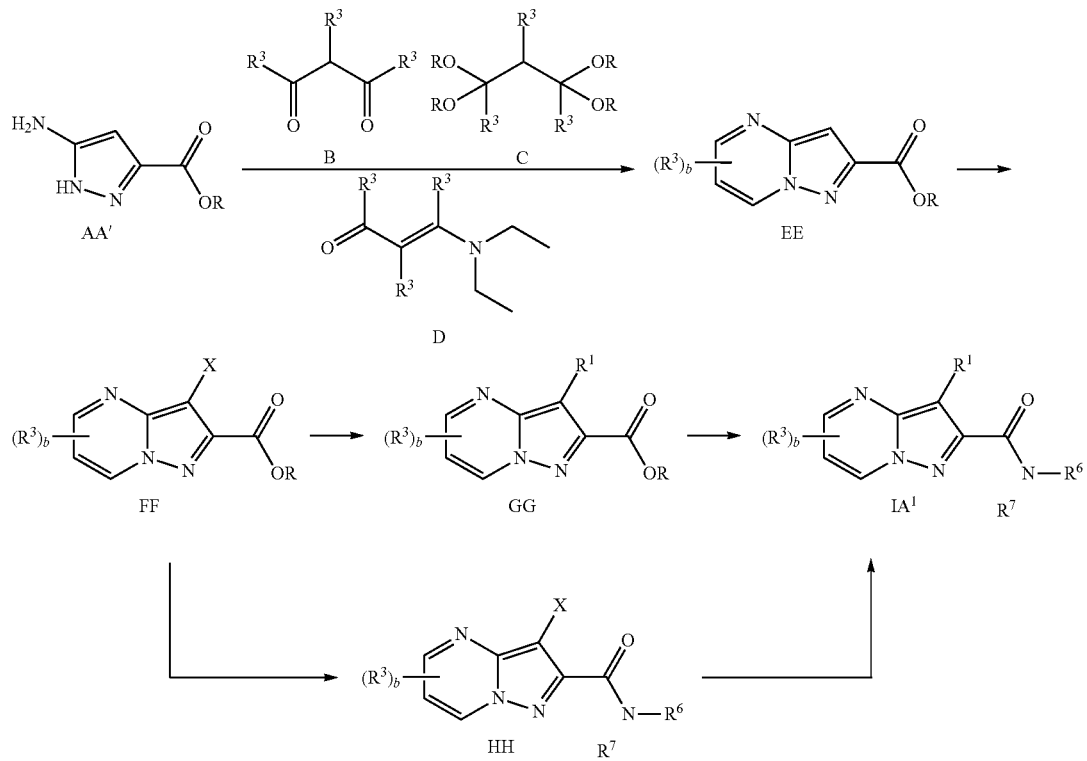

Scheme 2

Scheme 3 illustrates general synthetic preparations of compounds of Formula IA². Preparation of a compound of Formula AA" have been described in the literature (PCT Int. Appl. 2011045344). In a first step, a compound of Formula AA" is treated with an appropriately substituted 1,3-diketone (Formula B), protected 1,3-diketone (Formula C), or 1,3-diketone equivalent (Formula D) (PCT Int. Appl. 2010018481) and an acid catalyst in an appropriate solvent, from about room temperature to about 150° C., to form the compound of Formula EE" pyrazolopyrimidine, b is an integer selected from 0, 1, 2, or 3). During this initial step, each $R^3$ substituent of Formulas B, C and D should be represented by the same moiety as desired in the final product or a protected variation thereof. For example, the final product of Example 1 each $R^3$ is hydrogen. R of Formula C is a lower alkyl.

In the next step, the compound of Formula EE" is halogenated at the unsubstituted position of the pyrazole ring by treatment with an electrophilic halogen reagent such as N-iodosuccinimide (NIS), N-bromosuccinimide (NBS), iodine monochloride (ICl), iodine (I₂), bromine (Br₂), etc. in an inert solvent, potentially acid-catalyzed, from room temperature to 100° C. results in compound FF" (wherein X is a halogen selected from chlorine, iodine, or bromine). The compound of Formula FF" is then converted by a Suzuki-Miyaura reaction (*Chemical Society Reviews* 2014, 43, 412-443; *Accounts of Chemical Research* 2013, 46, 2626-2634) by treatment with base and an appropriate alkyl, aryl, or heteroaryl boronate in the presence of a transition metal catalyst (potentially palladium acetate or tris(dibenzylideneacetone) dipalladium), and a metal chelating ligand, in an appropriate solvent which installs the appropriate $R^1$ substituent on the intermediate compound of Formula GG". During this step, the $R^1$ substituent should be represented by the same moiety as desired in the final product or a protected variation thereof. For example, the final product of Example 1 $R^1$ should be represented by a chlorophenyl moiety.

In the next step, the Boc protecting group of intermediate of compound of Formula GG" is removed by treatment with an acid such as trifluoroacetic acid or hydrochloric acid in an appropriate solvent, if needed, at about 0° C. to about 100° C. to give a compound of Formula HH". The intermediate compound of Formula HH" can be acylated to the desired compound of Formula IA² by treatment with the appropriately substituted acyl chloride under basic conditions in appropriate solvents. The compound of Formula IA² could also be accessed by the addition of the appropriate acid in the presence of an amide coupling/dehydrating reagent such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), 1,3-dicyclohexylcarbodiimide (DCC), etc., at temperatures ranging from about −20° C. to about 100° C.

Scheme 3

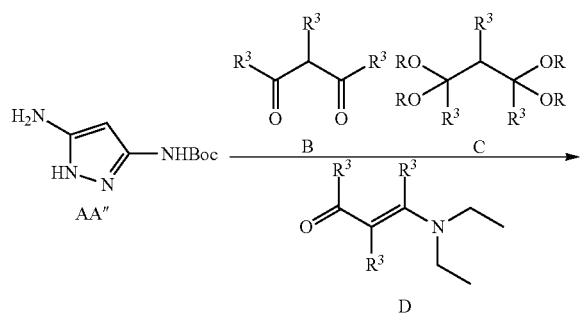

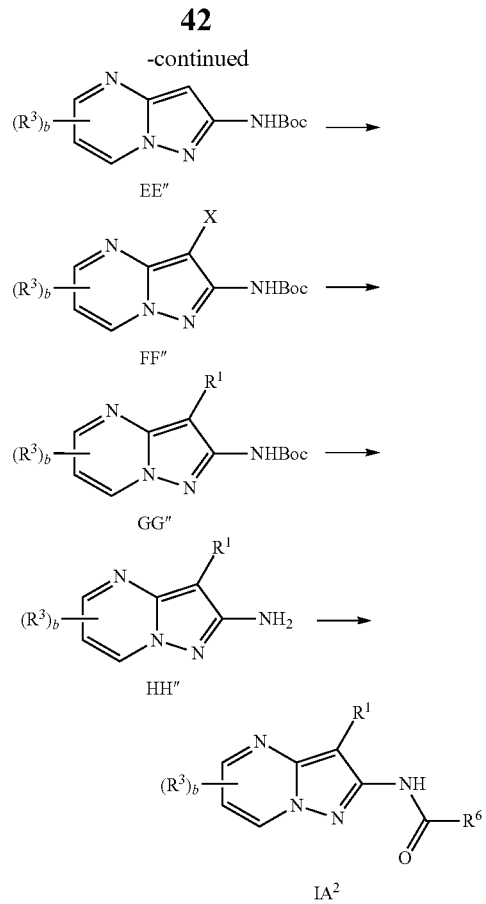

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

Azetidin-1-yl[3-(4-chlorophenyl)pyrazolo[1,5-a]pyrimidin-2-yl]methanone (1)

Step 1. Synthesis of ethyl pyrazolo[1,5-a]pyrimidine-2-carboxylate (C1)

A mixture of ethyl 5-amino-1H-pyrazole-3-carboxylate (64 g, 0.41 mol) and 1,1,3,3-tetraethoxypropane (91 g, 0.41 mol) in acetic acid (400 mL) was heated at reflux overnight. After removal of solvent in vacuo, the pH was adjusted to 8 with saturated aqueous sodium bicarbonate solution. The resulting mixture was extracted with dichloromethane, and the combined organic layers were dried, filtered, and concentrated under reduced pressure. Silica gel chromatography (Gradient: 1% to 99% dichloromethane in petroleum ether) afforded the product as a light yellow solid. Yield: 17.4 g, 91.0 mmol, 22%. $^1$H NMR (400 MHz, CDCl$_3$) δ 8.76 (ddd, J=7.2, 1.6, 0.9 Hz, 1H), 8.58 (dd, J=4.0, 1.7 Hz, 1H), 7.25 (br s, 1H), 6.96 (dd, J=7.1, 4.0 Hz, 1H), 4.51 (q, J=7.2 Hz, 2H), 1.46 (t, J=7.2 Hz, 3H).

Step 2. Synthesis of ethyl 3-iodopyrazolo[1,5-a]pyrimidine-2-carboxylate (C2)

N-Iodosuccinimide (20 g, 89 mmol) was added to a solution of C1 (12 g, 63 mmol) in dichloromethane (300 mL) and acetic acid (30 mL), and the reaction mixture was stirred at room temperature overnight. Dichloromethane (100 mL) and saturated aqueous sodium bicarbonate solution (100 mL) were added; the organic layer was washed with saturated aqueous sodium chloride solution (250 mL), dried over sodium sulfate, filtered, and concentrated in vacuo. Crystallization from ethanol afforded the product as a yellow solid. Yield: 15 g, 47 mmol, 75%. LCMS m/z 318.1 [M+H]$^+$. $^1$H NMR (400 MHz, CDCl$_3$) δ 8.75 (dd, J=7.0, 1.6 Hz, 1H), 8.68 (dd, J=4.0, 1.7 Hz, 1H), 7.04 (dd, J=7.0, 4.0 Hz, 1H), 4.55 (q, J=7.2 Hz, 2H), 1.50 (t, J=7.2 Hz, 3H).

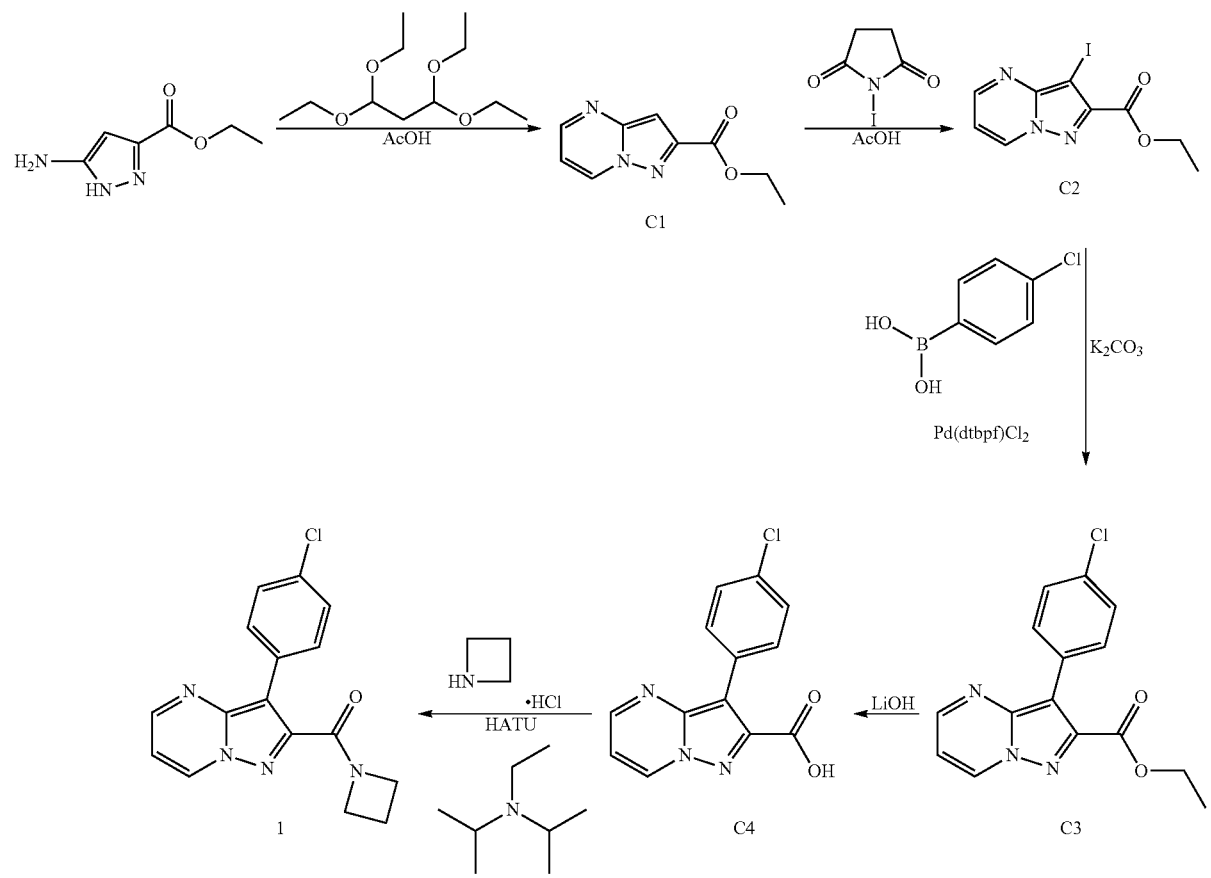

Step 3. Synthesis of ethyl 3-(4-chlorophenyl)pyrazolo[1,5-a]pyrimidine-2-carboxylate (C3)

A mixture of C2 (1.0 g, 3.2 mmol), (4-chlorophenyl) boronic acid (500 mg, 3.2 mmol), potassium carbonate (1.2 g, 8.7 mmol), and 1,4-dioxane (20 mL) was degassed several times with nitrogen, then treated with [1,1'-bis(di-tert-butylphosphino)ferrocene]dichloropalladium(II) (41 mg, 63 µmol). After the reaction mixture had been stirred at 85° C. overnight, it was diluted with water and extracted with ethyl acetate (4×25 mL). The combined organic layers were washed with saturated aqueous sodium chloride solution, dried over sodium sulfate, filtered, concentrated in vacuo, and purified via chromatography on silica gel to provide the product as a yellow solid. Yield: 700 mg, 2.3 mmol, 72%.

Step 4. Synthesis of 3-(4-chlorophenyl)pyrazolo[1,5-a]pyrimidine-2-carboxylic acid (C4)

A mixture of C3 (700 mg, 2.3 mmol), lithium hydroxide monohydrate (195 mg, 4.65 mmol), methanol (30 mL), and water (15 mL) was stirred at room temperature for 4 hours. After solvent had been removed in vacuo, the residue was diluted with water and acidified to a pH of 5 with hydrochloric acid. The mixture was extracted with ethyl acetate (4×25 mL), and the combined organic layers were dried over sodium sulfate, filtered, and concentrated under reduced pressure to provide the product as a yellow solid. Yield: 500 mg, 1.8 mmol, 78%.

Step 5. Synthesis of azetidin-1-yl[3-(4-chlorophenyl)pyrazolo[1,5-a]pyrimidin-2-yl]methanone (1)

N,N-Diisopropylethylamine (0.5 mL, 2.9 mmol) was added to a solution of C4 (190 mg, 0.694 mmol) and O-(7-azabenzotriazol-1-yl)-N,N,N',N'-tetramethyluronium hexafluorophosphate (HATU; 476 mg, 1.25 mmol) in N,N-dimethylformamide (10 mL). The reaction mixture was stirred at room temperature for 10 minutes, whereupon azetidine hydrochloride (193 mg, 2.06 mmol) was added, and stirring was continued for 4 hours. The reaction mixture was then diluted with water and extracted with ethyl acetate (3×40 mL). The combined organic layers were concentrated in vacuo; purification via reversed phase HPLC afforded the product as a yellow solid. Yield: 155 mg, 0.496 mmol, 71%. LCMS m/z 313.0 [M+H]$^+$. $^1$H NMR (400 MHz, CDCl$_3$) δ 8.68 (dd, J=7.0, 1.8 Hz, 1H), 8.58 (dd, J=4.0, 1.7 Hz, 1H), 7.78 (br d, J=8.5 Hz, 2H), 7.44 (br d, J=8.5 Hz, 2H), 6.96 (dd, J=7.1, 4.0 Hz, 1H), 4.19-4.28 (m, 2H), 4.09-4.18 (m, 2H), 2.23-2.33 (m, 2H).

Example 2

3-(4-Chlorophenyl)-N-propylpyrazolo[1,5-a]pyrimidine-2-carboxamide (2)

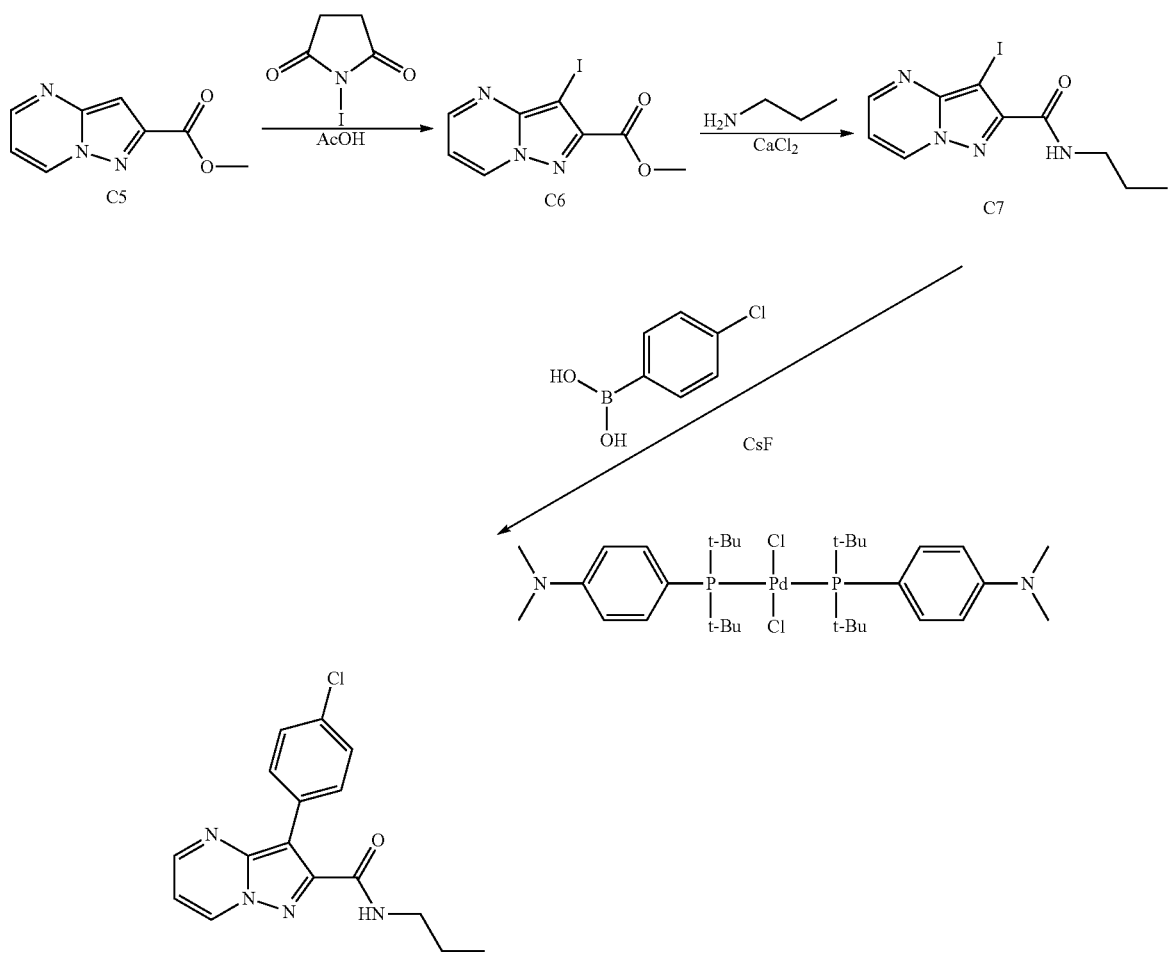

2

Step 1. Synthesis of methyl 3-iodopyrazolo[1,5-a]pyrimidine-2-carboxylate (C6)

To a solution of methyl pyrazolo[1,5-a]pyrimidine-2-carboxylate (C5) (140 mg, 0.79 mmol) in dichloromethane (30 mL) and acetic acid (3 mL) was added N-iodosuccinimide (267 mg, 1.19 mmol), and the reaction mixture was stirred at room temperature overnight. Dichloromethane (20 mL) was added, and the mixture was carefully adjusted to pH 7 with saturated aqueous sodium bicarbonate solution. The organic layer was washed with saturated aqueous sodium chloride solution (10 mL), dried over sodium sulfate, filtered, and concentrated in vacuo. Dichloromethane (2 mL) and n-hexane (20 mL) were added to the residue; after the mixture had been stirred at room temperature for 2 hours, the precipitate was collected via filtration. The filter cake was washed with n-hexane (10 mL) to afford the product as a gray solid. Yield: 200 mg, 0.66 mmol, 84%. LCMS m/z 303.7 [M+H]$^+$. $^1$H NMR (400 MHz, CDCl$_3$) δ 8.74 (dd, J=7.1, 1.7 Hz, 1H), 8.68 (dd, J=4.0, 1.6 Hz, 1H), 7.06 (dd, J=7.0, 4.0 Hz, 1H), 4.07 (s, 3H).

Step 2. Synthesis of 3-iodo-N-propylpyrazolo[1,5-a]pyrimidine-2-carboxamide (C7)

Propan-1-amine (105 mg, 1.78 mmol) and calcium chloride (74 mg, 0.67 mmol) were added to a solution of C6 (200 mg, 0.66 mmol) in methanol (20 mL), and the reaction mixture was stirred at 50° C. overnight. After solvent had been removed in vacuo, water was added to the residue, and the mixture was extracted with ethyl acetate (3×20 mL). The combined organic layers were washed with saturated aqueous sodium chloride solution, dried over sodium sulfate, filtered, and concentrated in vacuo to provide the product as a white solid. Yield: 180 mg, 0.54 mmol, 82%. LCMS m/z 330.8 [M+H]$^+$. $^1$H NMR (400 MHz, CDCl$_3$) δ 8.60-8.66 (m, 2H), 7.10-7.18 (br s, 1H), 7.01 (dd, J=7.1, 4.1 Hz, 1H), 3.48 (br q, J=6.7 Hz, 2H), 1.64-1.75 (m, 2H), 1.02 (t, J=7.4 Hz, 3H).

Step 3. Synthesis of 3-(4-chlorophenyl)-N-propylpyrazolo[1,5-a]pyrimidine-2-carboxamide (2)

To a solution of C7 (100 mg, 0.30 mmol) in 1,4-dioxane (15 mL) were added (4-chlorophenyl)boronic acid (94 mg, 0.60 mmol), bis[di-tert-butyl(4-dimethylaminophenyl)phosphine]dichloropalladium(II) (21 mg, 30 μmol), and cesium fluoride (138 mg, 0.908 mmol). The reaction mixture was stirred overnight at 100° C., whereupon it was filtered. The filtrate was concentrated in vacuo, and the residue was purified via reversed phase HPLC (Column: Phenomenex Gemini C18, 8 μm; Mobile phase A: aqueous ammonia (pH 10); Mobile phase B: acetonitrile; Gradient: 43% to 63% B), affording the product as a white solid. Yield: 21.2 mg, 67.4 μmol, 22%. LCMS m/z 315.0 [M+H]$^+$. $^1$H NMR (400 MHz, DMSO-d$_6$) δ 9.19 (br dd, J=7, 2 Hz, 1H), 8.67-8.71 (m, 1H), 8.60-8.67 (m, 1H), 7.80 (br d, J=8.7 Hz, 2H), 7.48 (br d, J=8.8 Hz, 2H), 7.24 (dd, J=7.2, 4.1 Hz, 1H), 3.23 (br q, J=7 Hz, 2H), 1.48-1.59 (m, 2H), 0.88 (t, J=7.5 Hz, 3H).

Example 3'

3-(4-chloro-3-fluorophenyl)pyrazolo[1,5-a]pyrimidin-2-amine (13)

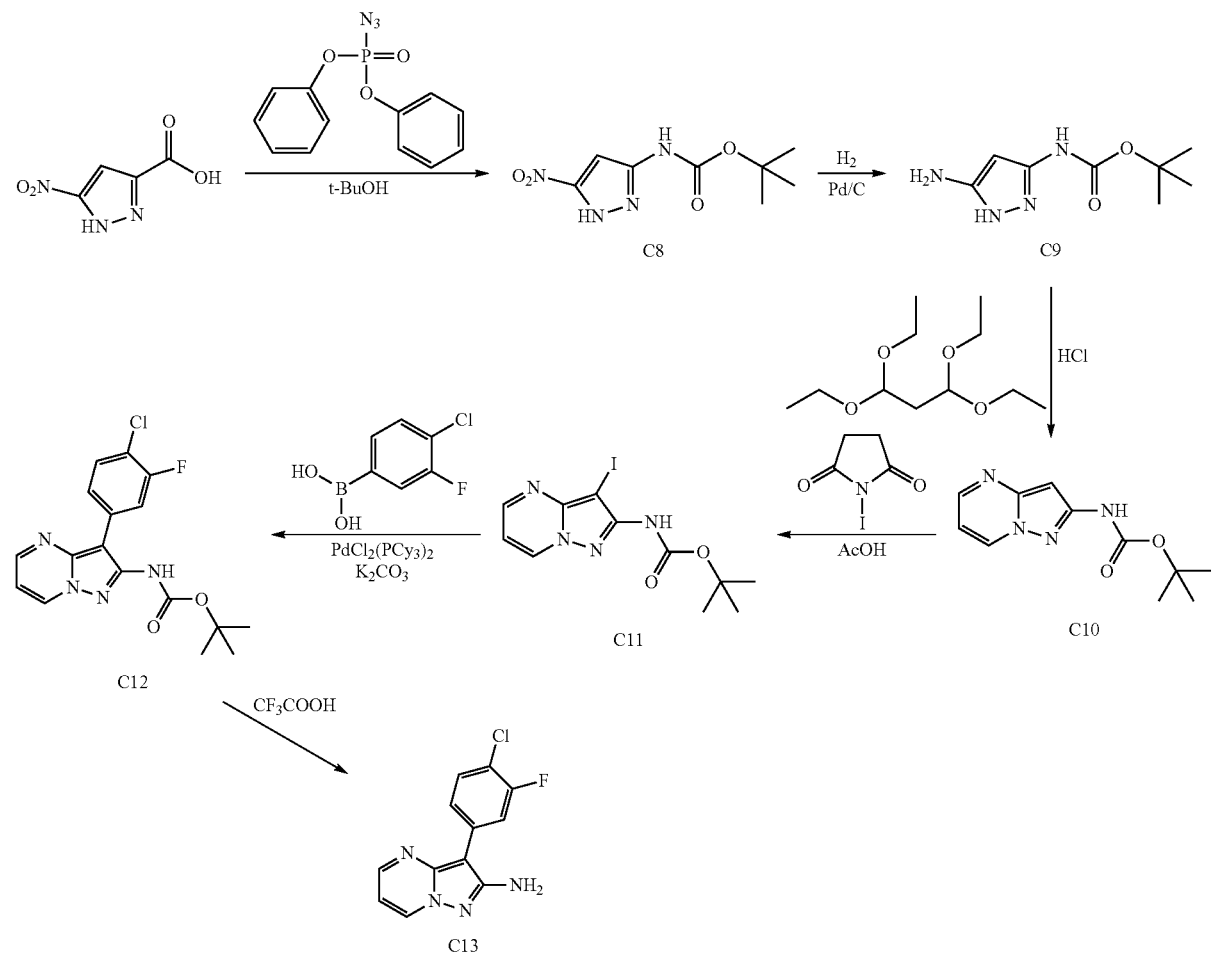

Step 1. Synthesis of tert-butyl (5-nitro-1H-pyrazol-3-yl)carbamate (C8)

To a solution of 5-nitro-1H-pyrazole-3-carboxylic acid (12.0 g, 76.4 mmol) in tert-butanol (200 mL) were added triethylamine (31 g, 0.31 mol) and diphenyl phosphorazidate (49 mL, 0.23 mol) in a drop-wise manner. The reaction mixture was stirred at reflux overnight, whereupon it was concentrated in vacuo; the residue was purified by chromatography on silica gel (Gradient: 9% to 50% ethyl acetate in petroleum ether) to afford the product as a yellow solid. Yield: 7.1 g, 31 mmol, 41%. $^1$H NMR (400 MHz, DMSO-$d_6$) δ 10.37 (br s, 1H), 6.45 (s, 1H), 1.48 (s, 9H).

Step 2. Synthesis of tert-butyl (5-amino-1H-pyrazol-3-yl)carbamate (C9)

A mixture of C8 (7.0 g, 31 mmol) and Pd/C (0.8 g) in methanol (200 mL) was hydrogenated (30 psi hydrogen) at 30° C. overnight. The reaction mixture was filtered and the filtrate was concentrated in vacuo, affording the product as a brown solid. Yield: 5.8 g, 29 mmol, 94%. $^1$H NMR (400 MHz, DMSO-$d_6$) δ 10.67 (s, 1H), 9.05 (br s, 1H), 5.31 (s, 1H), 4.82 (br s, 2H), 1.42 (s, 9H).

Step 3. Synthesis of tert-butyl pyrazolo[1,5-a]pyrimidin-2-ylcarbamate (C10)

1,1,3,3-Tetraethoxypropane (6.5 g, 30 mmol) and concentrated hydrochloric acid (5 mL) were added to a solution of C9 (5.6 g, 28 mmol) in ethanol (180 mL), and the reaction mixture was stirred at room temperature overnight. It was then concentrated in vacuo; purification via silica gel chromatography (Gradient: 17% to 50% ethyl acetate in petroleum ether) provided the product as a yellow solid. Yield: 4.4 g, 19 mmol, 68%. $^1$H NMR (400 MHz, DMSO-$d_6$) δ 10.23 (br s, 1H), 8.90 (ddd, J=6.9, 1.6, 0.9 Hz, 1H), 8.42 (dd, J=4.2, 1.7 Hz, 1H), 6.90 (dd, J=6.9, 4.1 Hz, 1H), 6.64 (br s, 1H), 1.49 (s, 9H).

Step 4. Synthesis of tert-butyl (3-iodopyrazolo[1,5-a]pyrimidin-2-yl)carbamate (C11)

A solution of C10 (3.5 g, 15 mmol) and N-iodosuccinimide (4.8 g, 21 mmol) in acetic acid (60 mL) was stirred at room temperature for 3 hours. The reaction mixture was concentrated in vacuo, and the residue was purified via chromatography on silica gel (Gradient: 17% to 50% ethyl acetate in petroleum ether) to afford the product as a yellow solid. Yield: 4.7 g, 13 mmol, 87%. LCMS m/z 382.9 [M+Na$^+$]. $^1$H NMR (400 MHz, DMSO-$d_6$) δ 9.38 (br s, 1H), 9.02 (dd, J=7.0, 1.7 Hz, 1H), 8.56 (dd, J=4.1, 1.8 Hz, 1H), 7.07 (dd, J=6.9, 4.1 Hz, 1H), 1.46 (s, 9H).

Step 5. Synthesis of tert-butyl [3-(4-chloro-3-fluorophenyl)pyrazolo[1,5-a]pyrimidin-2-yl]carbamate (C12)

To a solution of C11 (0.6 g, 1.7 mmol), (4-chloro-3-fluorophenyl)boronic acid (0.286 g, 1.64 mmol), and potassium carbonate (0.87 g, 0.63 mmol) in 1,4-dioxane (20 mL) and water (5 mL) was added dichlorobis(tricyclohexylphosphine)palladium(II) (98 mg, 0.13 mmol). The reaction mixture was degassed several times with nitrogen and then stirred at 80° C. overnight. After removal of solvent in vacuo, the residue was purified by chromatography on silica gel (Gradient: 17% to 67% ethyl acetate in petroleum ether) to provide a yellow solid (430 mg). By $^1$H NMR analysis, this material consisted of a 3.2:1 mixture of C12 and C10. Corrected yield: 358 mg, 0.987 mmol, 60%. $^1$H NMR (400 MHz, DMSO-$d_6$), product peaks only: δ 9.62 (br s, 1H), 9.10 (dd, J=6.9, 1.8 Hz, 1H), 8.65 (dd, J=4.1, 1.8 Hz, 1H), 7.79 (dd, J=11.4, 1.9 Hz, 1H), 7.73 (br dd, half of ABX pattern, J=8.4, 1.9 Hz, 1H), 7.66 (dd, half of ABX pattern, J=8.3, 8.3 Hz, 1H), 7.16 (dd, J=7.0, 4.1 Hz, 1H), 1.32 (s, 9H).

Step 6. Synthesis of 3-(4-chloro-3-fluorophenyl)pyrazolo[1,5-a]pyrimidin-2-amine (C13)

Trifluoroacetic acid (5 mL) was added to a solution of C12 (0.91 g, 2.5 mmol) in dichloromethane (60 mL), and the reaction mixture was stirred at room temperature for 6 hours. Concentration in vacuo afforded the product as a yellow solid containing some contaminants. Yield: 600 mg, <2.3 mmol, <92%. $^1$H NMR (400 MHz, DMSO-$d_6$), product peaks only: δ 8.81 (dd, J=6.7, 1.7 Hz, 1H), 8.40 (dd, J=4.3, 1.8 Hz, 1H), 7.87 (dd, J=11.7, 1.9 Hz, 1H), 7.75-7.79 (m, 1H), 7.59 (dd, J=8.5, 8.3 Hz, 1H), 6.85 (dd, J=6.8, 4.3 Hz, 1H), 5.97 (br s, 2H).

Example 4

N-[3-(4-Chloro-3-fluorophenyl)pyrazolo[1,5-a]pyrimidin-2-yl]butanamide (4)

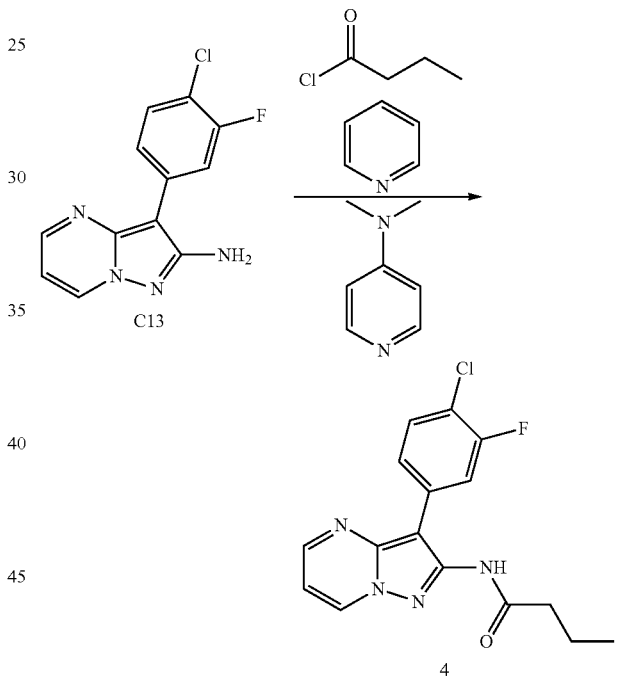

Butanoyl chloride (24.5 mg, 0.230 mmol) was added to a mixture of C13 (30 mg, 0.11 mmol) and 4-(dimethylamino)pyridine (7.0 mg, 57 μmol) in pyridine (3 mL). The reaction mixture was irradiated in a microwave synthesizer for 1 hour at 150° C., allowed to cool, and partitioned between water (20 mL) and ethyl acetate (50 mL). The organic layer was washed with saturated aqueous sodium chloride solution (30 mL), dried over sodium sulfate, filtered, and concentrated under reduced pressure. Purification via reversed phase HPLC (Column: Agella Venusil ASB C18, 5 μm; Mobile phase A: 0.225% formic acid in water; Mobile phase B: acetonitrile; Gradient: 33% to 63% B) afforded the product as a yellow solid. Yield: 12 mg, 36 μmol, 33%. LCMS m/z 332.9 [M+H]$^+$. $^1$H NMR (400 MHz, DMSO-$d_6$) δ 10.31 (br s, 1H), 9.12 (br d, J=6.7 Hz, 1H), 8.64-8.69 (m, 1H), 7.77 (br d, J=11.3 Hz, 1H), 7.69 (br d, half of AB quartet, J=8.4 Hz, 1H), 7.63 (br dd, half of ABX pattern, J=8.4, 8.0 Hz, 1H), 7.18 (dd, J=6.8, 4.4 Hz, 1H), 2.34 (t, J=7.2 Hz, 2H), 1.53-1.66 (m, 2H), 0.91 (t, J=7.2 Hz, 3H).

Example 5

3-(4-Chloro-3-fluorophenyl)-N-cyclopropylpyrazolo[1,5-a]pyrimidine-2-carboxamide (5)

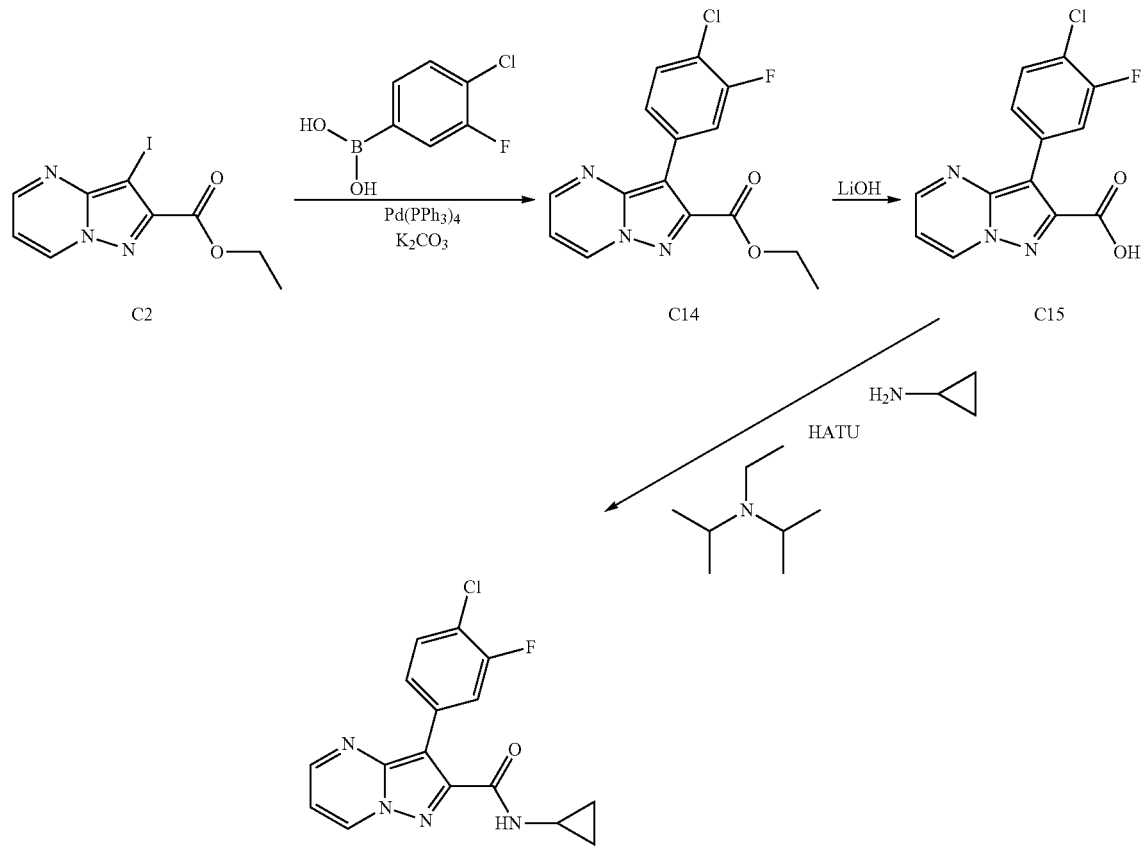

Step 1. Synthesis of ethyl 3-(4-chloro-3-fluorophenyl)pyrazolo[1,5-a]pyrimidine-2-carboxylate (C14)

To a solution of C2 (20.0 g, 63.1 mmol), (4-chloro-3-fluorophenyl)boronic acid (22.0 g, 126 mmol), and potassium carbonate (26 g, 190 mmol) in 1,4-dioxane (600 mL) and water (60 mL) was added tetrakis(triphenylphosphine)palladium(0) (4.4 g, 3.8 mmol). The reaction mixture was degassed several times with nitrogen and then heated at 100° C. overnight. After the reaction mixture had been diluted with water (900 mL), the resulting solid was collected via filtration; purification via silica gel chromatography (Gradient: 9% to 67% ethyl acetate in petroleum ether) provided the product as a brown solid. Yield: 9.0 g, 28 mmol, 44%. $^1$H NMR (400 MHz, DMSO-$d_6$) δ 9.28 (dd, J=7.2, 1.6 Hz, 1H), 8.72 (dd, J=4.0, 1.6 Hz, 1H), 7.70 (dd, J=10.9, 1.9 Hz, 1H), 7.65 (dd, J=8.2, 8.2 Hz, 1H), 7.52 (br dd, J=8.3, 2.0 Hz, 1H), 7.32 (dd, J=7.2, 4.0 Hz, 1H), 4.33 (q, J=7.1 Hz, 2H), 1.26 (t, J=7.2 Hz, 3H).

Step 2. Synthesis of 3-(4-chloro-3-fluorophenyl)pyrazolo[1,5-a]pyrimidine-2-carboxylic acid (C15)

To a solution of C14 (16 g, 50 mmol) in methanol (200 mL) was added lithium hydroxide monohydrate (6.3 g, 150 mmol), and the reaction mixture was stirred at room temperature overnight. After acidification to a pH of 5-6 with concentrated hydrochloric acid, the mixture was concentrated in vacuo to afford the product as a brown solid. Yield: 13.8 g, 47.3 mmol, 95%. $^1$H NMR (400 MHz, DMSO-$d_6$) δ 13.47 (v br s, 1H), 9.25 (dd, J=7.1, 1.7 Hz, 1H), 8.71 (dd, J=4.0, 1.6 Hz, 1H), 7.71 (dd, J=11.0, 1.9 Hz, 1H), 7.65 (dd, J=8.3, 8.2 Hz, 1H), 7.54 (br dd, J=8.4, 1.9 Hz, 1H), 7.29 (dd, J=7.0, 4.0 Hz, 1H).

Step 3. Synthesis of 3-(4-chloro-3-fluorophenyl)-N-cyclopropylpyrazolo[1,5-a]pyrimidine-2-carboxamide (5)

To a solution of C15 (1.0 g, 3.4 mmol) and O-(7-azabenzotriazol-1-yl)-N,N,N',N'-tetramethyluronium hexafluorophosphate (3.52 g, 9.26 mmol) in N,N-dimethylformamide (30 mL) were added cyclopropylamine (1.96 g, 34.3 mmol) and N,N-diisopropylethylamine (16.1 mL, 92.4 mmol). The reaction mixture was stirred at room temperature for 24 hours, whereupon it was partitioned between ethyl acetate and aqueous ammonium chloride solution. The aqueous layer was extracted with ethyl acetate, and the combined organic layers were washed with saturated aqueous sodium chloride solution and concentrated in vacuo. The resulting material was triturated with ethyl acetate to provide a solid, which was combined with the crude product of a similar reaction carried out on C15 (0.123 g, 0.422 mmol) and purified via silica gel chromatography (Gradient: 0% to 100% dichloromethane in heptane) to afford the product as a yellow solid. Combined yield: 860 mg, 2.60 mmol, 68%. LCMS m/z 331.1, 333.1 [M+H]$^+$. $^1$H NMR (400 MHz, DMSO-$d_6$) δ 9.19 (dd, J=7.1, 1.7 Hz, 1H), 8.76 (br d, J=4

Hz, 1H), 8.74 (dd, J=4.0, 1.7 Hz, 1H), 7.86 (dd, J=11.4, 1.8 Hz, 1H), 7.70 (dd, half of ABX pattern, J=8.4, 1.8 Hz, 1H), 7.65 (dd, half of ABX pattern, J=8.5, 7.6 Hz, 1H), 7.28 (dd, J=7.0, 4.0 Hz, 1H), 2.86-2.94 (m, 1H), 0.68-0.75 (m, 2H), 0.57-0.63 (m, 2H).

Example 6

3-(4-Chloro-2-methylphenyl)-N-cyclopropylpyrazolo[1,5-a]pyrimidine-2-carboxamide (6)

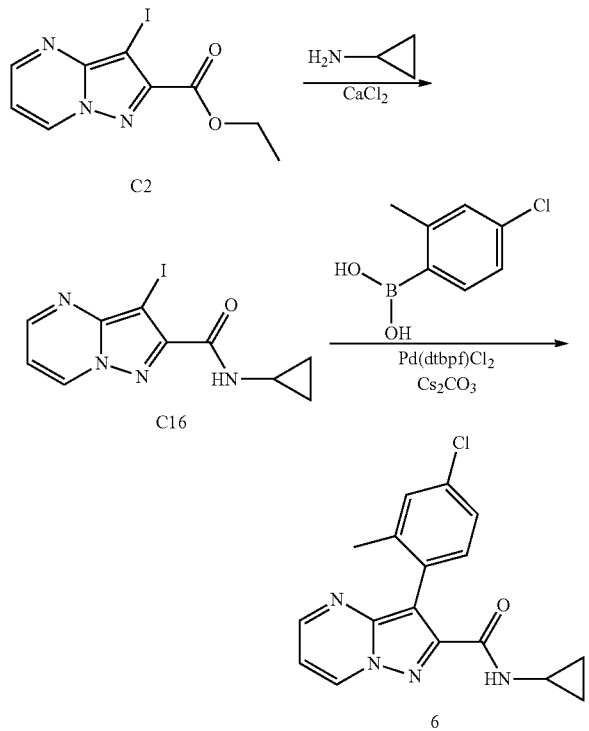

Step 1. Synthesis of N-cyclopropyl-3-iodopyrazolo [1,5-a]pyrimidine-2-carboxamide (C16)

A mixture of C2 (7.50 g, 23.6 mmol), cyclopropylamine (98%, 13.8 g, 237 mmol), and calcium chloride (2.63 g, 23.7 mmol) in methanol (160 mL) was heated for 3 hours at 50° C., then allowed to stir at room temperature overnight. The reaction mixture was concentrated in vacuo, and the residue was partitioned between water and dichloromethane. The aqueous layer was extracted twice with dichloromethane, and the combined organic layers were dried over magnesium sulfate, filtered, and concentrated under reduced pressure. The resulting solid was triturated with dichloromethane to afford the product as a tan solid. Yield: 3.29 g, 10.0 mmol, 42%. LCMS m/z 329.1 [M+H]$^+$. $^1$H NMR (400 MHz, CDCl$_3$) δ 8.63 (dd, J=4.0, 1.7 Hz, 1H), 8.59 (dd, J=7.0, 1.7 Hz, 1H), 7.18 (br s, 1H), 7.00 (dd, J=7.0, 4.0 Hz, 1H), 2.91-2.98 (m, 1H), 0.87-0.93 (m, 2H), 0.67-0.72 (m, 2H).

Step 2. Synthesis of 3-(4-chloro-2-methylphenyl)-N-cyclopropylpyrazolo[1,5-a]pyrimidine-2-carboxamide (6)

A mixture of C16 (3.02 g, 9.20 mmol), (4-chloro-2-methylphenyl)boronic acid (2.36 g, 13.8 mmol), and cesium carbonate (6.01 g, 18.4 mmol) in 1,4-dioxane (60 mL) and water (6 mL) was treated with [1,1'-bis(di-tert-butylphosphino)ferrocene]dichloropalladium(II) (97%, 310 mg, 0.461 mmol); the reaction flask was evacuated and filled with nitrogen three times, and then heated at 100° C. for 3 hours. The reaction mixture was stirred at room temperature overnight, combined with a second similar reaction mixture derived from C16 (1.02 g, 3.11 mmol), and partitioned between ethyl acetate and water. The aqueous layer was extracted twice with ethyl acetate, and the combined organic layers were dried over magnesium sulfate, filtered, and concentrated in vacuo. Chromatography on silica gel (Gradient: 20% to 80% ethyl acetate in heptane) afforded a tan foam, which was recrystallized from ethyl acetate/heptane to afford the product as a slightly off-white solid. Yield: 2.38 g, 7.28 mmol, 59%. This material was found to be crystalline via powder X-ray diffraction. LCMS m/z 327.1, 329.2 [M+H]$^+$. $^1$H NMR (400 MHz, CDCl$_3$) δ 8.65 (dd, J=7.0, 1.8 Hz, 1H), 8.53 (dd, J=4.0, 1.8 Hz, 1H), 7.31-7.33 (m, 1H), 7.23-7.29 (m, 2H), 7.02-7.08 (br s, 1H), 6.98 (dd, J=7.1, 4.0 Hz, 1H), 2.83-2.90 (m, 1H), 2.15 (s, 3H), 0.80-0.86 (m, 2H), 0.58-0.63 (m, 2H).

Example 7

3-(4-Chlorophenyl)-N-cyclopropyl-6-fluoropyrazolo [1,5-a]pyrimidine-2-carboxamide (7)

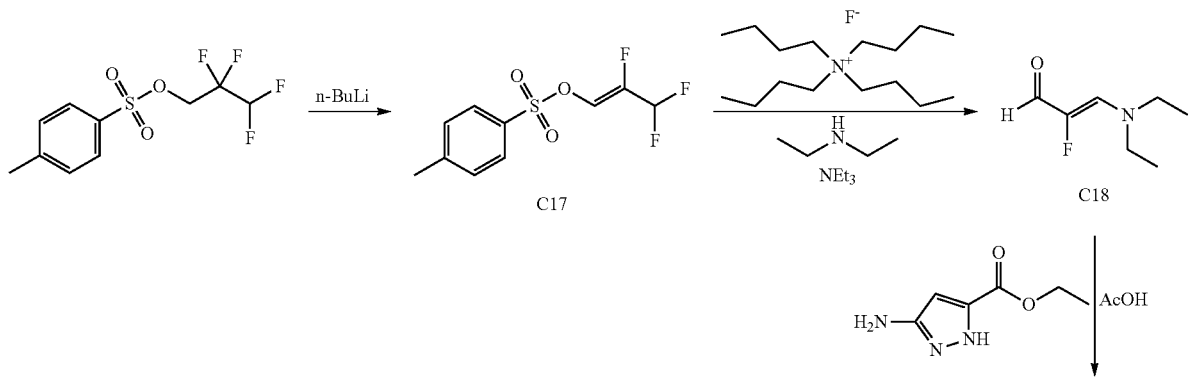

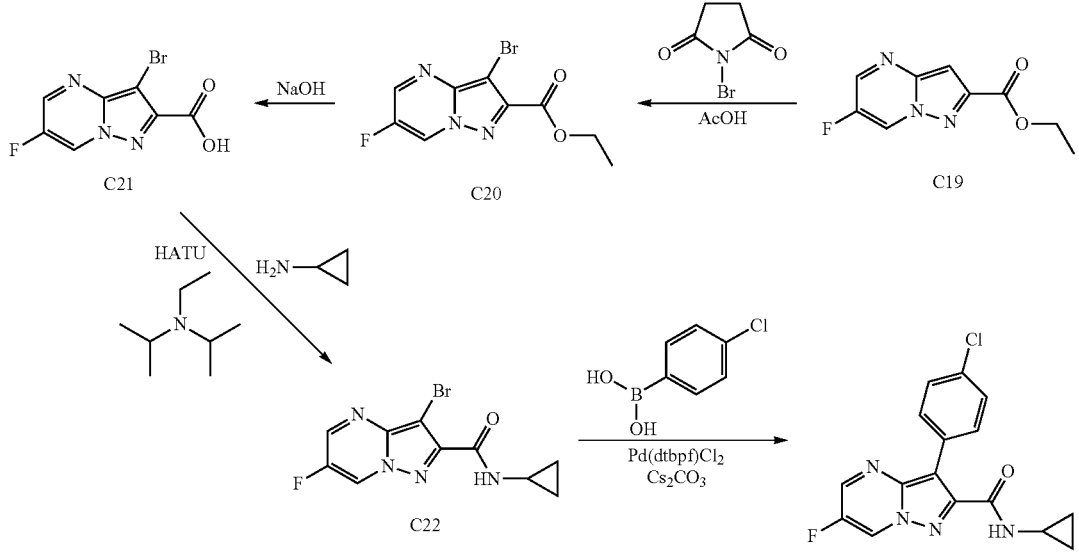

Step 1. Synthesis of (1Z)-2,3,3-trifluoroprop-1-en-1-yl 4-methylbenzenesulfonate (C17)

n-Butyllithium (2.5 M solution, 280 mL, 700 mmol) was added drop-wise over 1.5 hours to a solution of 2,2,3,3-tetrafluoropropyl 4-methylbenzenesulfonate (80 g, 280 mmol) in tetrahydrofuran (2 L), while the reaction temperature was maintained at or below −60° C. After completion of the addition, the reaction mixture was stirred at −70° C. for 10 minutes, whereupon it was quenched via addition of aqueous hydrochloric acid (3 M, 240 mL, 720 mmol) and allowed to warm to room temperature. The mixture was extracted with ethyl acetate (2×1 L) and the combined organic layers were washed with saturated aqueous sodium chloride solution, dried over sodium sulfate, filtered, and concentrated in vacuo to afford the product (80 g) as a brown oil, which was used in the next step without further purification.

Step 2. Synthesis of (2Z)-3-(diethylamino)-2-fluoroprop-2-enal (C18)

To a solution of C17 (from the previous step, 80 g, 280 mmol) in acetonitrile (800 mL) was added a solution of diethylamine (26.5 g, 362 mmol), tetrabutylammonium fluoride (6.9 g, 26 mmol), and triethylamine (34 g, 340 mmol) in acetonitrile (1.5 L). The reaction mixture was stirred at room temperature for 18 hours, whereupon it was concentrated in vacuo. The residue was dissolved in dichloromethane (2 L), washed with saturated aqueous sodium chloride solution, dried over sodium sulfate, filtered, and concentrated in vacuo. Purification via chromatography on silica gel (Eluents: dichloromethane in petroleum ether, followed by ethyl acetate in dichloromethane) provided the product as a brown oil. Yield: 18.0 g, 124 mmol, 44% over two steps.

Step 3. Synthesis of ethyl 6-fluoropyrazolo[1,5-a]pyrimidine-2-carboxylate (C19)

A solution of C18 (18.0 g, 124 mmol) and ethyl 3-amino-1H-pyrazole-5-carboxylate (18 g, 120 mmol) in acetic acid (300 mL) was stirred at reflux for 3 hours, whereupon it was concentrated in vacuo. The residue was dissolved in dichloromethane (500 mL), sequentially washed with water and with saturated aqueous sodium chloride solution, dried over sodium sulfate, filtered, and concentrated under reduced pressure. Purification via chromatography on silica gel (Eluents: dichloromethane in petroleum ether, followed by ethyl acetate in dichloromethane) provided a solid, which was washed with a 5:1 mixture of petroleum ether and ethyl acetate to afford the product as a yellow solid. Yield: 13 g, 62 mmol, 52%.

Step 4. Synthesis of ethyl 3-bromo-6-fluoropyrazolo[1,5-a]pyrimidine-2-carboxylate (C20)

A solution of C19 (23 g, 0.11 mol) in dichloromethane (500 mL) was cooled to 10° C. and treated in a portion-wise manner with N-bromosuccinimide (39 g, 0.22 mol) and acetic acid (3 mL). The reaction mixture was stirred at room temperature for 18 hours, whereupon it was washed sequentially with water, with aqueous sodium bicarbonate solution, and with saturated aqueous sodium chloride solution, dried over sodium sulfate, filtered, and concentrated in vacuo. The residue was washed with ethanol to provide the product as a yellow solid. Yield: 13 g, 45 mmol, 41%. LCMS m/z 289.8 [M+H]$^+$. $^1$H NMR (400 MHz, CDCl$_3$) δ 8.67-8.71 (m, 2H), 4.54 (q, J=7.1 Hz, 2H), 1.49 (t, J=7.2 Hz, 3H).

Step 5. Synthesis of 3-bromo-6-fluoropyrazolo[1,5-a]pyrimidine-2-carboxylic acid (C21)

An aqueous solution of sodium hydroxide (1 M, 25.5 mL, 25.5 mmol) was added to a solution of C20 (7.00 g, 24.3 mmol) in methanol (50 mL) and tetrahydrofuran (50 mL), and the reaction mixture was heated overnight at 50° C. After cooling to room temperature, the reaction mixture was concentrated to dryness in vacuo, treated with aqueous hydrochloric acid (1 M, 26 mL, 26 mmol), stirred, and filtered. The collected precipitate was washed with water and with diethyl ether to afford the product as a light yellow solid. Yield: 6.17 g, 23.7 mmol, 98%. LCMS m/z 214.1, 216.1 [M−H−CO$_2$]$^−$. $^1$H NMR (400 MHz, DMSO-d$_6$) δ 13.64 (br s, 1H), 9.67 (dd, J=4.6, 2.5 Hz, 1H), 8.96 (d, J=2.5 Hz, 1H).

Step 6. Synthesis of 3-bromo-N-cyclopropyl-6-fluoropyrazolo[1,5-a]pyrimidine-2-carboxamide (C22)

O-(7-Azabenzotriazol-1-yl)-N,N,N',N'-tetramethyluronium hexafluorophosphate (98%, 11.0 g, 28.4 mmol) was added to a 0° C. solution of C21 (6.17 g, 23.7 mmol), cyclopropylamine (1.76 g, 30.8 mmol), and N,N-diisopropylethylamine (98%, 6.33 mL, 35.6 mmol) in dichloromethane (100 mL). After stirring overnight at room temperature, the reaction mixture was concentrated in vacuo to approximately 30% of its original volume, and then diluted with water and tert-butyl methyl ether. The mixture was vigorously stirred, and subsequently filtered; the collected precipitate was washed with water and with tert-butyl methyl ether to afford the product as a yellow solid. Yield: 5.08 g, 17.0 mmol, 72%. LCMS m/z 299.1, 301.1 [M+H]$^+$. $^1$H NMR (400 MHz, DMSO-d$_6$) δ 9.54 (dd, J=4.5, 2.5 Hz, 1H), 8.94 (d, J=2.5 Hz, 1H), 8.63 (br d, J=4 Hz, 1H), 2.84-2.92 (m, 1H), 0.67-0.73 (m, 2H), 0.59-0.65 (m, 2H).

Step 7. Synthesis of 3-(4-chlorophenyl)-N-cyclopropyl-6-fluoropyrazolo[1,5-a]pyrimidine-2-carboxamide (7)

Compound C22 (3.00 g, 10.0 mmol), (4-chlorophenyl)boronic acid (2.04 g, 13.0 mmol), cesium carbonate (6.54 g, 20.1 mmol), and [1,1'-bis(di-tert-butylphosphino)ferrocene]dichloropalladium(II) (97%, 337 mg, 0.502 mmol) were combined in a degassed mixture of 1,4-dioxane (220 mL) and water (22 mL). The reaction flask was evacuated and filled with nitrogen three times, then placed in an 80° C. oil bath for 1 hour. The reaction mixture was cooled to room temperature, diluted with ethyl acetate and washed with water; a precipitate was collected via filtration and washed with ethyl acetate. The combined organic filtrates were washed with water, dried over magnesium sulfate, filtered, and concentrated in vacuo. The resulting solid was combined with the isolated precipitate and triturated with tert-butyl methyl ether to afford the product as a yellow solid. Yield: 3.05 g, 9.22 mmol, 92%. A portion of this material was mixed with a 1:1 mixture of ethanol and ethyl acetate and heated at 90° C., then allowed to gradually cool to room temperature. The resulting precipitate was collected via filtration and washed with diethyl ether to afford the product as a yellow solid. LCMS m/z 331.2, 333.2 [M+H]$^+$. $^1$H NMR (400 MHz, DMSO-d$_6$) δ 9.57 (dd, J=4.4, 2.4 Hz, 1H), 8.92 (d, J=2.5 Hz, 1H), 8.70 (br d, J=4 Hz, 1H), 7.77 (br d, J=8.6 Hz, 2H), 7.50 (br d, J=8.6 Hz, 2H), 2.84-2.92 (m, 1H), 0.67-0.74 (m, 2H), 0.55-0.62 (m, 2H).

Example 8

3-(4-Chlorophenyl)-N-(pyrimidin-2-yl)pyrazolo[1,5-a]pyrimidine-2-carboxamide (8)

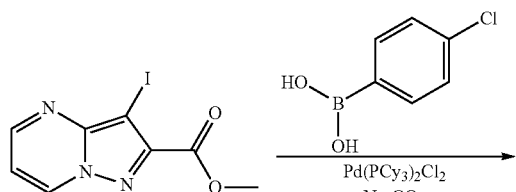

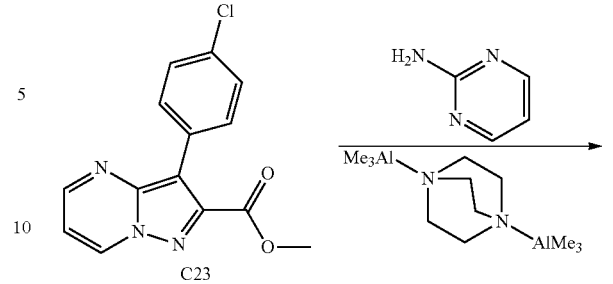

Step 1. Synthesis of methyl 3-(4-chlorophenyl)pyrazolo[1,5-a]pyrimidine-2-carboxylate (C23)

A mixture of C6 (300 mg, 0.99 mmol), (4-chlorophenyl)boronic acid (250 mg, 1.6 mmol), dichlorobis(tricyclohexylphosphine)palladium(II) (74 mg, 0.10 mmol) and sodium carbonate (315 mg, 2.97 mmol) in 1,4-dioxane (15 mL) and water (1.5 mL) was purged with nitrogen for 2 minutes. The reaction mixture was then stirred at 100° C. for 18 hours, whereupon it was partitioned between ethyl acetate (50 mL) and water (50 mL). The aqueous layer was extracted with ethyl acetate (3×50 mL), and the combined organic layers were washed with saturated aqueous sodium chloride solution, dried over sodium sulfate, filtered, and concentrated under reduced pressure. Silica gel chromatography (Gradient: 1% to 70% ethyl acetate in petroleum ether) afforded the product as a yellow solid. Yield: 150 mg, 0.52 mmol, 52%. $^1$H NMR (400 MHz, CDCl$_3$) δ 8.77 (dd, J=7.0, 1.8 Hz, 1H), 8.61 (dd, J=3.9, 1.8 Hz, 1H), 7.63 (br d, J=8.7 Hz, 2H), 7.46 (br d, J=8.5 Hz, 2H), 7.04 (dd, J=7.1, 4.0 Hz, 1H), 3.98 (s, 3H).

Step 2. Synthesis of 3-(4-chlorophenyl)-N-(pyrimidin-2-yl)pyrazolo[1,5-a]pyrimidine-2-carboxamide (8)

To a solution of pyrimidin-2-amine (40 mg, 0.42 mmol) in tetrahydrofuran (2 mL) was added bis(trimethylaluminum)-1,4-diazabicyclo[2.2.2]octane adduct (108 mg, 0.421 mmol) in three portions over 2 minutes. This mixture was stirred for 15 minutes at room temperature, whereupon a suspension of C23 (30 mg, 0.10 mmol) in tetrahydrofuran (1 mL) was added. The reaction mixture was heated at 70° C. for 18 hours, and the solvent was then removed in vacuo. Purification via reversed phase HPLC (Column: Phenomenex Gemini C18, 8 μm: Mobile phase A: aqueous ammonia, pH 10; Mobile phase B: acetonitrile; Gradient: 37% to 57% B) afforded the product as a yellow solid. Yield: 10 mg, 28 μmol, 28%. LCMS m/z 351.0 [M+H]$^+$. $^1$H NMR (400

MHz, CDCl$_3$) δ 9.85 (br s, 1H), 8.67-8.73 (m, 3H), 8.62 (dd, J=4.0, 1.6 Hz, 1H), 7.83 (br d, J=8.5 Hz, 2H), 7.43 (br d, J=8.5 Hz, 2H), 7.08 (t, J=4.9 Hz, 1H), 7.06 (dd, J=7.2, 4.0 Hz, 1H).

Example 9

Azetidin-1-yl[3-(4-chlorophenyl)-6-fluoropyrazolo[1,5-a]pyrimidin-2-yl]methanone, Formate Salt (9)

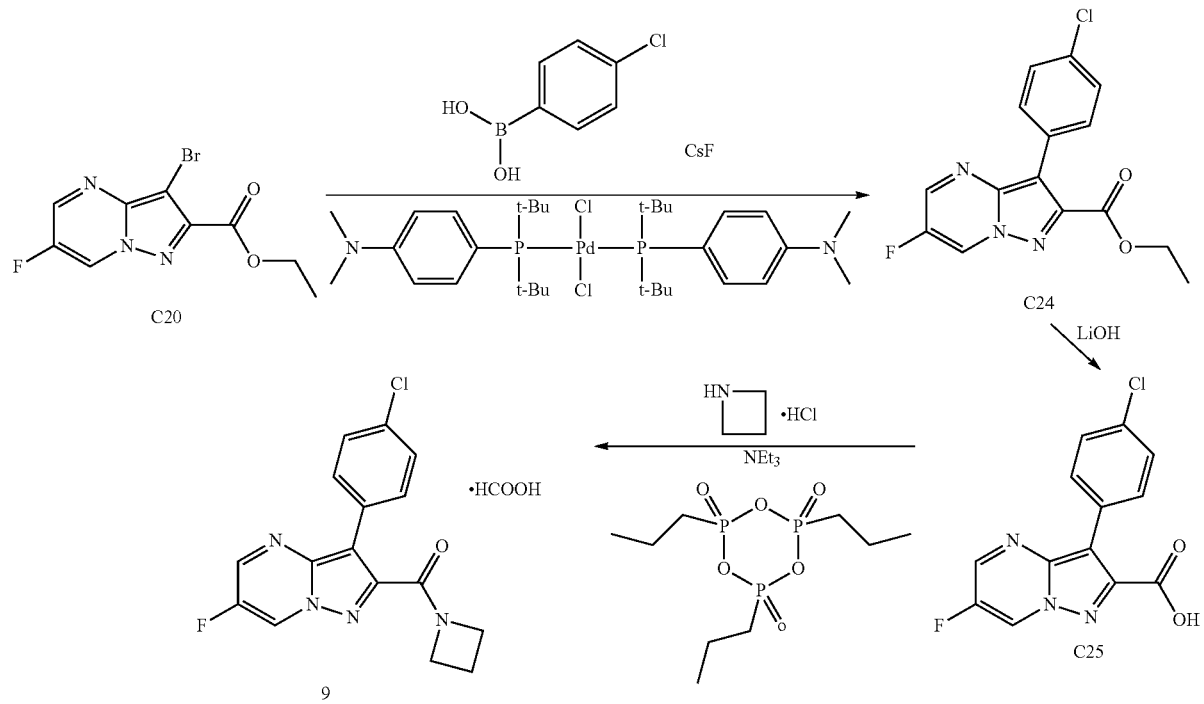

Step 1. Synthesis of ethyl 3-(4-chlorophenyl)-6-fluoropyrazolo[1,5-a]pyrimidine-2-carboxylate (C24)

Bis[di-tert-butyl(4-dimethylaminophenyl)phosphine]dichloropalladium(II) (64 mg, 90 μmol) was added to a solution of C20 (500 mg, 1.74 mmol), (4-chlorophenyl)boronic acid (407 mg, 2.60 mmol), and cesium fluoride (793 mg, 5.22 mmol) in a mixture of 1,4-dioxane and water (10:1, 20 mL), and the reaction mixture was stirred at 100° C. for 16 hours. Water (20 mL) was added, and the resulting mixture was extracted with ethyl acetate (3×30 mL). The combined organic layers were washed with saturated aqueous sodium chloride solution (20 mL), dried over sodium sulfate, filtered, and concentrated in vacuo; silica gel chromatography (Gradient: 0% to 20% ethyl acetate in petroleum ether) provided the product as a yellow solid. Yield: 200 mg, 0.63 mmol, 36%. $^1$H NMR (400 MHz, CDCl$_3$) δ 8.71 (dd, J=3.3, 2.8 Hz, 1H), 8.62 (d, J=2.6 Hz, 1H), 7.60 (br d, J=8.3 Hz, 2H), 7.46 (br d, J=8.4 Hz, 2H), 4.45 (q, J=7.1 Hz, 2H), 1.38 (t, J=7.1 Hz, 3H).

Step 2. Synthesis of 3-(4-chlorophenyl)-6-fluoropyrazolo[1,5-a]pyrimidine-2-carboxylic acid (C25)

To a solution of C24 (200 mg, 0.63 mmol) in tetrahydrofuran/ethanol/water (2:2:1, 10 mL) was added lithium hydroxide monohydrate (79 mg, 1.9 mmol), and the reaction mixture was stirred at room temperature for 2 hours. Solvents were removed in vacuo, the residue was diluted with water (10 mL), and the mixture was acidified to a pH of 3 with 1 M hydrochloric acid. The aqueous layer was extracted with ethyl acetate (3×30 mL), and the combined organic layers were washed with saturated aqueous sodium chloride solution (20 mL), dried over sodium sulfate, filtered, and concentrated under reduced pressure to provide the product as a white solid. Yield: 160 mg, 0.55 mmol, 87%. This material was used in the next step without additional purification. $^1$H NMR (400 MHz, DMSO-d$_6$) δ 13.4 (v br s, 1H), 9.66 (dd, J=4.6, 2.6 Hz, 1H), 8.91 (d, J=2.6 Hz, 1H), 7.64 (br d, J=8.7 Hz, 2H), 7.51 (br d, J=8.7 Hz, 2H).

Step 3. Synthesis of azetidin-1-yl[3-(4-chlorophenyl)-6-fluoropyrazolo[1,5-a]pyrimidin-2-yl]methanone, Formate Salt (9)

A solution of C25 (80 mg, 0.27 mmol), azetidine hydrochloride (38 mg, 0.41 mmol), triethylamine (131 mg, 1.29 mmol), and 2,4,6-tripropyl-1,3,5,2,4,6-trioxatriphosphinane 2,4,6-trioxide (T3P, as a 50% solution in ethyl acetate; 131 mg, 0.412 mmol) in N,N-dimethylformamide (3 mL) was stirred at room temperature for 16 hours. The reaction mixture was then diluted with water (20 mL) and extracted with ethyl acetate (3×20 mL). The combined organic layers were concentrated in vacuo and purified by reversed phase HPLC (Boston Symmetrix ODS-H, 5 μm; Mobile phase A: 0.225% formic acid in water; Mobile phase B: acetonitrile; Gradient: 43% to 63% B) to afford the product as a yellow solid. Yield: 42 mg, 0.13 mmol, 48%. LCMS m/z 331.1 [M+H]$^+$. $^1$H NMR (400 MHz, CDCl$_3$) δ 8.60-8.64 (m, 2H), 7.74 (br d, J=8.5 Hz, 2H), 7.43 (br d, J=8.7 Hz, 2H), 4.20-4.27 (m, 2H), 4.13-4.19 (m, 2H), 2.25-2.34 (m, 2H).

Using the methodology described above for Examples 1-9, Examples 10-21 were synthesized. See Table 1 for specific methods employed, as well as characterization data for these Examples.

TABLE 1

*Method of preparation, structure, and physicochemical data for Examples 10-21.*

| Example Number | Method of Synthesis: Example Number; Source of Non-commercial Starting Materials | Structure | $^1$H NMR (400 MHz, CDCl$_3$) δ (ppm); Mass spectrum, observed ion m/z [M + H]$^+$ or HPLC retention time; Mass spectrum m/z [M + H]$^+$ (unless otherwise indicated) |
|---|---|---|---|
| 10 | Example 1[1]; C6 | 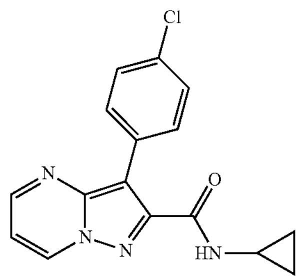 [SMILES: O=C(NC1CC1)c1nn2cccnc2c1-c1ccc(Cl)cc1] | 8.62 (br d, J = 7.0 Hz, 1H), 8.56 (dd, J = 3.9, 1.6 Hz, 1H), 7.75 (br d, J = 8.5 Hz, 2H), 7.42 (br d, J = 8.5 Hz, 2H), 7.17 (br s, 1H), 6.98 (dd, J = 7.0, 4.0 Hz, 1H), 2.87-2.95 (m, 1H), 0.84-0.91 (m, 2H), 0.63-0.69 (m, 2H); 312.9 |
| 11 | Example 1; C4 | 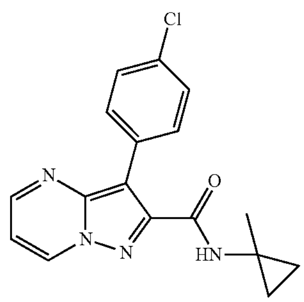 [SMILES: CC1(NC(=O)c2nn3cccnc3c2-c2ccc(Cl)cc2)CC1] | 8.63 (dd, J = 7.0, 1.8 Hz, 1H), 8.57 (dd, J = 3.9, 1.8 Hz, 1H), 7.75 (br d, J = 8.7 Hz, 2H), 7.43 (br d, J = 8.7 Hz, 2H), 7.35 (brs, 1H), 6.98 (dd, J = 7.1, 4.0 Hz, 1H), 1.50 (s, 3H), 0.87-0.92 (m, 2H), 0.72-0.76 (m, 2H); 326.9 |
| 12 | Example 2; C2 | 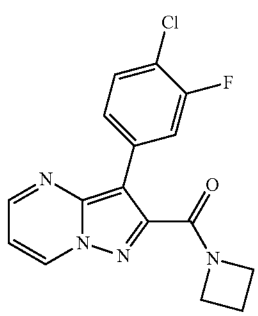 [SMILES: O=C(c1nn2cccnc2c1-c1ccc(Cl)c(F)c1)N1CCC1] | 8.66-8.71 (m, 1H), 8.59-8.63 (m, 1H), 7.75 (dd, J = 10.7, 1.8 Hz, 1H), 7.57-7.63 (m, 1H), 7.46 (dd, J = 8.0, 8.0 Hz, 1H), 7.00 (dd, J = 7, 4 Hz, 1H), 4.18-4.29 (m, 4H), 2.27-2.37 (m, 2H); 330.9 |
| 13 | Example 2; C16 | 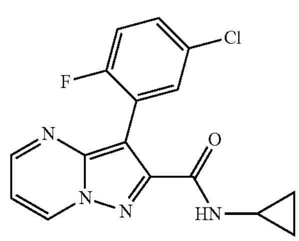 [SMILES: O=C(NC1CC1)c1nn2cccnc2c1-c1cc(Cl)ccc1F] | 8.65 (dd, J = 7.0, 1.8 Hz, 1H), 8.60 (dd, J = 3.9, 1.8 Hz, 1H), 7.58 (dd, J = 6.2, 2.8 Hz, 1H), 7.30-7.36 (m, 1H), 7.09-7.16 (m, 2H), 7.02 (dd, J = 7.1, 4.0 Hz, 1H), 2.86-2.95 (m, 1H), 0.83-0.91 (m, 2H), 0.64-0.70 (m, 2H); 330.9 |
| 14 | Example 2[2]; C1 | 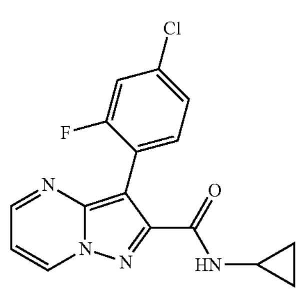 [SMILES: O=C(NC1CC1)c1nn2cccnc2c1-c1ccc(Cl)cc1F] | $^1$H NMR (400 MHz, CD$_3$OD) δ 8.99 (dd, J = 7.0, 1.6 Hz, 1H), 8.60 (dd, J = 4.1, 1.7 Hz, 1H), 7.60 (dd, J = 8.7, 7.9 Hz, 1H), 7.25-7.31 (m, 2H), 7.17 (dd, J = 7.1, 4.1 Hz, 1H), 2.78-2.85 (m, 1H), 0.78-0.84 (m, 2H), 0.63-0.68 (m, 2H); 330.8 |

TABLE 1-continued

Method of preparation, structure, and physicochemical data for Examples 10-21.

| Example Number | Method of Synthesis: Example Number; Source of Non-commercial Starting Materials | Structure | $^1$H NMR (400 MHz, CDCl$_3$) δ (ppm); Mass spectrum, observed ion m/z [M + H]$^+$ or HPLC retention time; Mass spectrum m/z [M + H]$^+$ (unless otherwise indicated) |
|---|---|---|---|
| 15 | Example 1[1]; C2 | 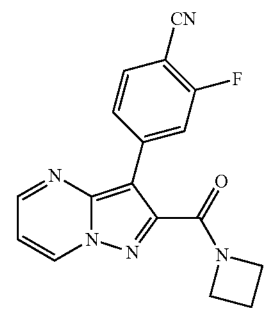 [SMILES: N#Cc1ccc(-c2c(C(=O)N3CCC3)nn3cccnc23)cc1F] | 8.71 (br d, J = 7 Hz, 1H), 8.66 (br d, J = 4 Hz, 1H), 7.92 (br d, J = 10.7 Hz, 1H), 7.85 (br d, J = 8.0 Hz, 1H), 7.67 (dd, J = 8.0, 7.3 Hz, 1H), 7.05 (dd, J = 7.0, 4.1 Hz, 1H), 4.23-4.40 (br m, 4H), 2.31-2.42 (m, 2H); 322.2 |
| 16 | Example 2[3]; C2 | 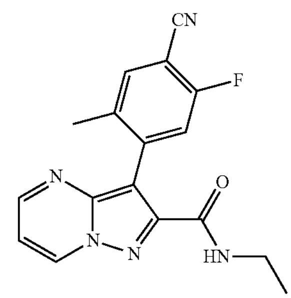 [SMILES: CCNC(=O)c1nn2cccnc2c1-c1cc(F)c(C#N)cc1C] | $^1$H NMR (400 MHz, CD$_3$OD) δ 9.03 (dd, J = 7.2, 1.6 Hz, 1H), 8.60 (dd, J = 4.1, 1.7 Hz, 1H), 7.66 (d, J = 6.6 Hz, 1H), 7.28 (d, J = 9.9 Hz, 1H), 7.19 (dd, J = 7.1, 4.1 Hz, 1H), 3.38 (q, J = 7.2 Hz, 2H), 2.15 (s, 3H), 1.21 (t, J = 7.2 Hz, 3H); 323.9 |
| 17 | Example 2[3] | 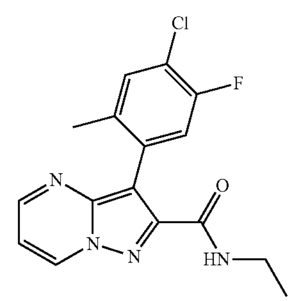 [SMILES: CCNC(=O)c1nn2cccnc2c1-c1cc(F)c(Cl)cc1C] | $^1$H NMR (400 MHz, CD$_3$OD) δ 9.01 (dd, J = 7.1, 1.7 Hz, 1H), 8.57 (dd, J = 4.0, 1.6 Hz, 1H), 7.39 (br d, J = 7.6 Hz, 1H), 7.17 (dd, J = 7.2, 4.0 Hz, 1H), 7.15 (d, J = 10 Hz, 1H), 3.38 (q, J = 7.2 Hz, 2H), 2.09 (s, 3H), 1.20 (t, J = 7.2 Hz, 3H); 332.9 |
| 18 | Example 6 | 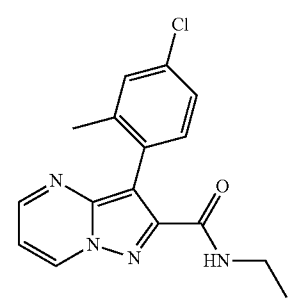 [SMILES: CCNC(=O)c1nn2cccnc2c1-c1ccc(Cl)cc1C] | 2.89 minutes[4]; 315 |

TABLE 1-continued

Method of preparation, structure, and physicochemical data for Examples 10-21.

| Example Number | Method of Synthesis: Example Number; Source of Non-commercial Starting Materials | Structure | $^1$H NMR (400 MHz, CDCl$_3$) δ (ppm); Mass spectrum, observed ion m/z [M + H]$^+$ or HPLC retention time; Mass spectrum m/z [M + H]$^+$ (unless otherwise indicated) |
|---|---|---|---|
| 19 | Example 6 | 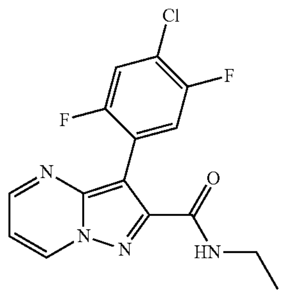 [SMILES: CCNC(=O)c1nn2cccnc2c1-c1cc(F)c(Cl)cc1F] | 2.88 minutes[4]; 337 |
| 20 | Example 2; C2 | 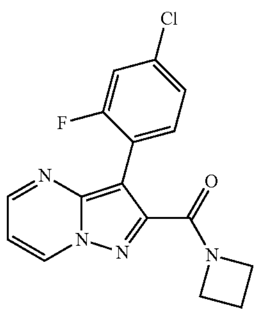 [SMILES: O=C(c1nn2cccnc2c1-c1ccc(Cl)cc1F)N1CCC1] | $^1$H NMR (400 MHz, CD$_3$OD) δ 9.00 (dd, J = 7.1, 1.7 Hz, 1H), 8.61 (dd, J = 4.0, 1.6 Hz, 1H), 7.64 (dd, J = 8.7, 7.9 Hz, 1H), 7.26-7.32 (m, 2H), 7.17 (dd, J = 7.2, 4.0 Hz, 1H), 4.50-4.56 (m, 2H), 4.17-4.23 (m, 2H), 2.35-2.45 (m, 2H); 330.9 |
| 21 | Example 2; C2 | 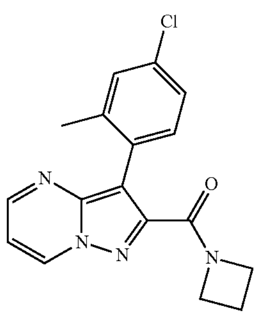 [SMILES: Cc1cc(Cl)ccc1-c1c(C(=O)N2CCC2)nn2cccnc12] | $^1$H NMR (400 MHz, CD$_3$OD) δ 8.99 (dd, J = 7.2, 1.6 Hz. 1H), 8.55 (dd, J = 4.1, 1.7 Hz, 1H), 7.32-7.34 (m, 1H), 7.22-7.24 (m, 2H), 7.14 (dd, J = 7.2, 4.0 Hz, 1H), 4.45-4.52 (m, 2H), 4.11-4.17 (m, 2H), 2.30-2.40 (m, 2H), 2.16 (d, J = 0.5 Hz, 3H); 326.8 |

1. In this case, the catalyst used for the Suzuki reaction was dichlorobis(tricyclohexylphosphine)palladium(II).

2. Compound C1 was converted to 3-bromo-N-cyclopropylpyrazolo[1,5-a]pyrimidine-2-carboxamide using the method described for transformation of C19 to C22 in Example 7.

3. The requisite aryl boronate derivative was prepared from the corresponding aryl bromide via reaction with 4,4,4',4',5,5,5',5'-octamethyl-2,2'-bi-1,3,2-dioxaborolane in the presence of [1,1'-bis(diphenylphosphino)ferrocene]dichloropalladium(II) and potassium acetate.

4. Conditions for analytical HPLC.

Column: Waters XBridge C18, 2.1 × 50 mm, 5 μm;

Mobile phase A: 0.0375% trifluoroacetic acid in water;

Mobile phase B: 0.01875% trifluoroacetic acid in acetonitrile;

Gradient: 1% to 5% B over 0.6 minutes;

5% to 100% B over 3.4 minutes;

Flow rate: 0.8 mL/minute.

TABLE 2

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
| --- | --- | --- |
| 22 | 4-cyano-5-fluoro-2-methylphenyl pyrazolo[1,5-a]pyrimidine-3-yl, N-cyclobutyl carboxamide | 350.2 |
| 23 | 4-cyano-5-fluoro-2-methylphenyl pyrazolo[1,5-a]pyrimidine-3-yl, N-cyclopropyl carboxamide | 336.2 |
| 24 | 4-chloro-5-fluoro-2-methylphenyl pyrazolo[1,5-a]pyrimidine-3-yl, N-cyclobutyl carboxamide | 359.1, 361.1 |
| 25 | 4-chloro-5-fluoro-2-methylphenyl pyrazolo[1,5-a]pyrimidine-3-yl, N-cyclopropyl carboxamide | 345.1, 347.1 |
| 26 | 4-chlorophenyl pyrazolo[1,5-a]pyrimidine-3-yl, N-isopropyl carboxamide | 315.2, 317.2 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
| --- | --- | --- |
| 27 | 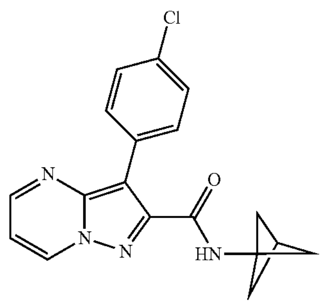 [SMILES: O=C(NC12CC(C1)C2)c1nn2cccnc2c1-c1ccc(Cl)cc1] | 339.1 |
| 28 | 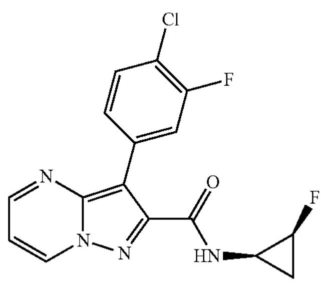 [SMILES: O=C(N[C@@H]1C[C@@H]1F)c1nn2cccnc2c1-c1ccc(Cl)c(F)c1] | 348.9 |
| 29 | 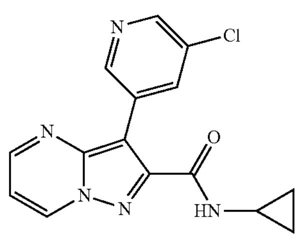 [SMILES: O=C(NC1CC1)c1nn2cccnc2c1-c1cncc(Cl)c1] | 313.9 |
| 30 | 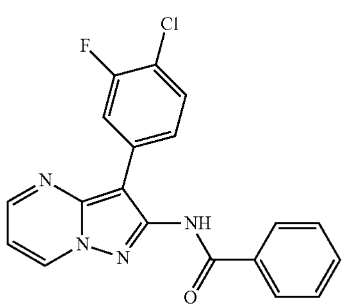 [SMILES: O=C(Nc1nn2cccnc2c1-c1ccc(Cl)c(F)c1)c1ccccc1] | 367.0 |
| 31 | 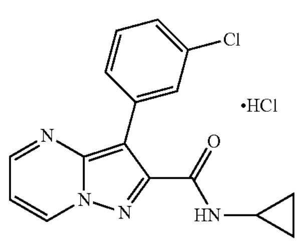 [SMILES: O=C(NC1CC1)c1nn2cccnc2c1-c1cccc(Cl)c1 ; Cl] | 313.0 |

TABLE 2-continued
Examples 22-76 were prepared using methods analogous to those employed for Examples 1-21, or via methodology known to those skilled in the art.
Structure and mass spectrometry data for Examples 22-76.
| Example Number | Structure | Mass spectrum, observed ion m/z [M + H]+ |
|---|---|---|
| 32 | 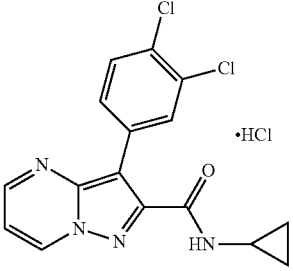 [SMILES: O=C(NC1CC1)c1nn2cccnc2c1-c1ccc(Cl)c(Cl)c1 ; Cl] | 346.9 |
| 33 | 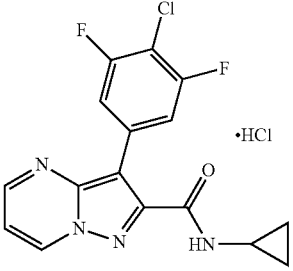 [SMILES: O=C(NC1CC1)c1nn2cccnc2c1-c1cc(F)c(Cl)c(F)c1 ; Cl] | 348.9 |
| 34 | 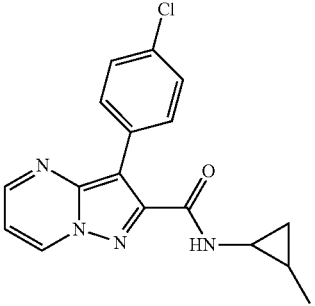 [SMILES: CC1CC1NC(=O)c1nn2cccnc2c1-c1ccc(Cl)cc1] | 326.9 |
| 35 | 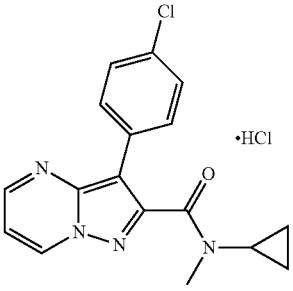 [SMILES: CN(C(=O)c1nn2cccnc2c1-c1ccc(Cl)cc1)C1CC1 ; Cl] | 326.9 |
| 36 | 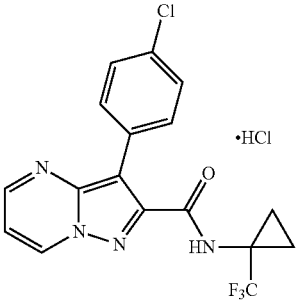 [SMILES: O=C(NC1(C(F)(F)F)CC1)c1nn2cccnc2c1-c1ccc(Cl)cc1 ; Cl] | 380.9 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
|---|---|---|
| 37 | 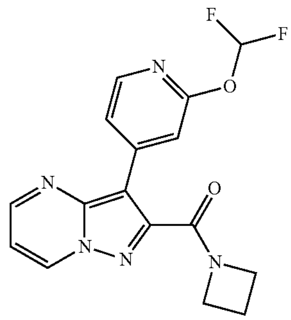 [SMILES: O=C(c1nn2cccnc2c1-c1ccnc(OC(F)F)c1)N1CCC1] | 345.9 |
| 38 | ·HCOOH | 346.0 |
| 39 | 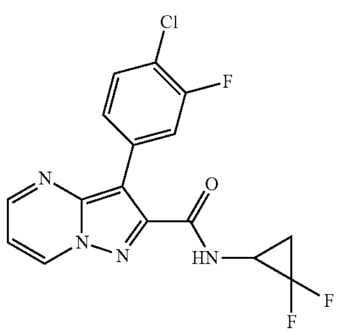 [SMILES: O=C(NC1CC1(F)F)c1nn2cccnc2c1-c1ccc(Cl)c(F)c1] | 366.9 |
| 40 | 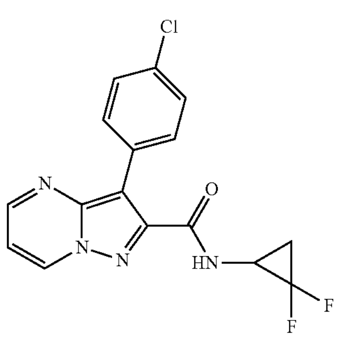 [SMILES: O=C(NC1CC1(F)F)c1nn2cccnc2c1-c1ccc(Cl)cc1] | 348.9 |

TABLE 2-continued
Examples 22-76 were prepared using methods analogous to those employed for Examples 1-21, or via methodology known to those skilled in the art.
Structure and mass spectrometry data for Examples 22-76.
| Example Number | Structure | Mass spectrum, observed ion m/z [M + H]+ |
|---|---|---|
| 41 | 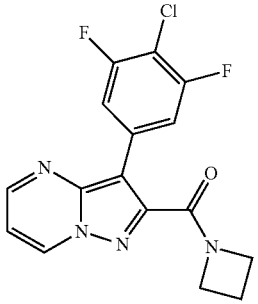 [SMILES: O=C(c1nn2cccnc2c1-c1cc(F)c(Cl)c(F)c1)N1CCC1] | 348.9 |
| 42 | 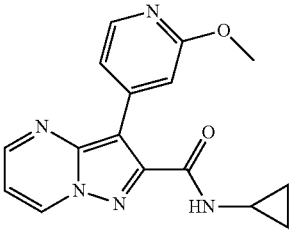 [SMILES: COc1cc(-c2c(C(=O)NC3CC3)nn3cccnc23)ccn1] | 310.0 |
| 43 | 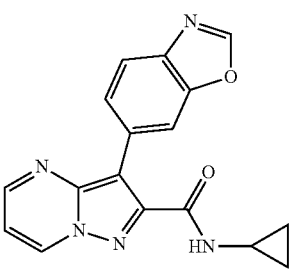 [SMILES: O=C(NC1CC1)c1nn2cccnc2c1-c1ccc2ncoc2c1] | 320.1 |
| 44 | 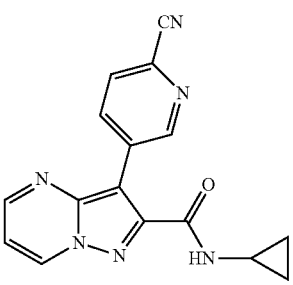 [SMILES: N#Cc1ccc(-c2c(C(=O)NC3CC3)nn3cccnc23)cn1] | 305.2 |
| 45 | 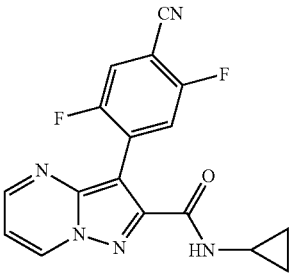 | 340.1 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
| --- | --- | --- |
| 46 | 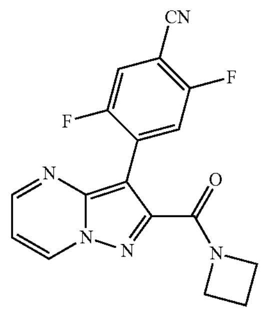 [SMILES: N#Cc1cc(F)c(-c2c(C(=O)N3CCC3)nn3cccnc23)cc1F] | 340.1 |
| 47 | 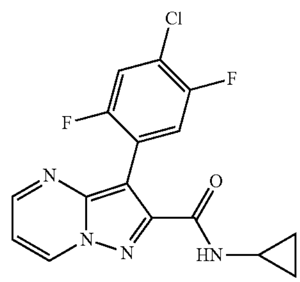 [SMILES: O=C(NC1CC1)c1nn2cccnc2c1-c1cc(F)c(Cl)cc1F] | 348.9 |
| 48 | 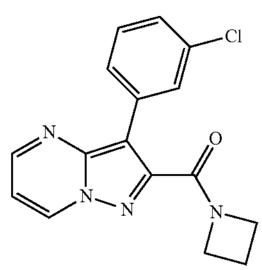 [SMILES: O=C(c1nn2cccnc2c1-c1cccc(Cl)c1)N1CCC1] | 312.9 |
| 49 | 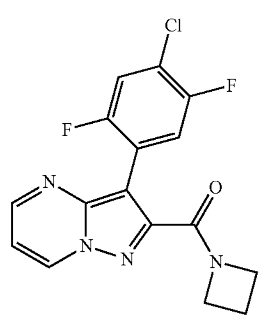 | 348.9 |
| 50 | 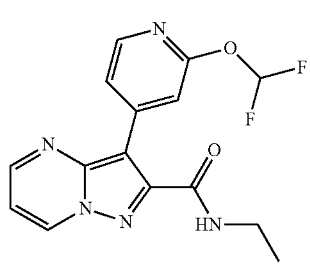 [SMILES: CCNC(=O)c1nn2cccnc2c1-c1ccnc(OC(F)F)c1] | 334 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
|---|---|---|
| 51 | 3-(4-chloro-2-methylphenyl)-N-isopropylpyrazolo[1,5-a]pyrimidine-2-carboxamide | 329 |
| 52 | 3-(4-chlorophenyl)-N-ethylpyrazolo[1,5-a]pyrimidine-2-carboxamide | 301 |
| 53 | 3-(4-chloro-3-fluorophenyl)-N-ethylpyrazolo[1,5-a]pyrimidine-2-carboxamide | 319 |
| 54 | 3-(4-chloro-5-fluoro-2-methylphenyl)-N-isopropylpyrazolo[1,5-a]pyrimidine-2-carboxamide | 347 |
| 55 | 3-(4-chloro-2-methylphenyl)-N-cyclopropyl-6-fluoropyrazolo[1,5-a]pyrimidine-2-carboxamide | 345.0 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
| --- | --- | --- |
| 56 | 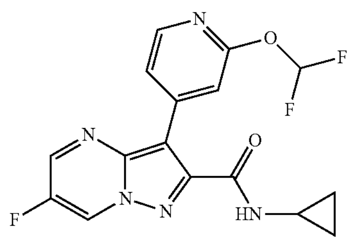 [SMILES: O=C(NC1CC1)c1nn2cc(F)cnc2c1-c1ccnc(OC(F)F)c1] | 363.9 |
| 57 | 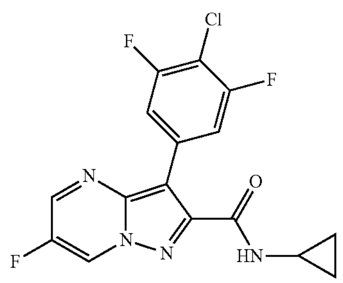 [SMILES: O=C(NC1CC1)c1nn2cc(F)cnc2c1-c1cc(F)c(Cl)c(F)c1] | 366.9 |
| 58 | 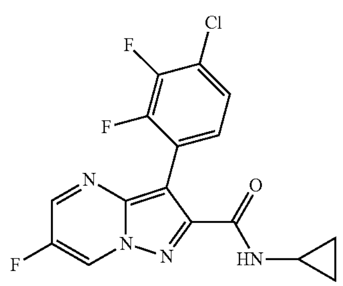 [SMILES: O=C(NC1CC1)c1nn2cc(F)cnc2c1-c1ccc(Cl)c(F)c1F] | 366.9 |
| 59 | 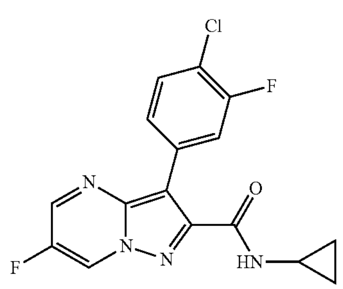 [SMILES: O=C(NC1CC1)c1nn2cc(F)cnc2c1-c1ccc(Cl)c(F)c1] | 348.8 |
| 60 | 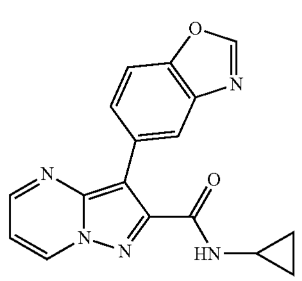 [SMILES: O=C(NC1CC1)c1nn2cccnc2c1-c1ccc2ocnc2c1] | 320.1 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
| --- | --- | --- |
| 61 | 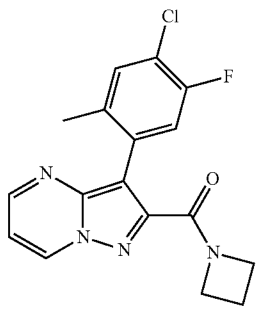 [SMILES: Cc1cc(Cl)c(F)cc1-c1c(C(=O)N2CCC2)nn2cccnc12] | 344.8 |
| 62 | 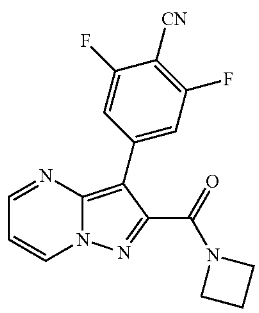 [SMILES: N#Cc1c(F)cc(-c2c(C(=O)N3CCC3)nn3cccnc23)cc1F] | 339.8 |
| 63 | 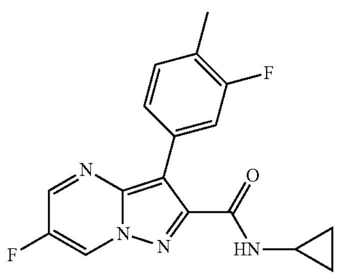 [SMILES: Cc1ccc(-c2c(C(=O)NC3CC3)nn3cc(F)cnc23)cc1F] | 329.1 |
| 64 | 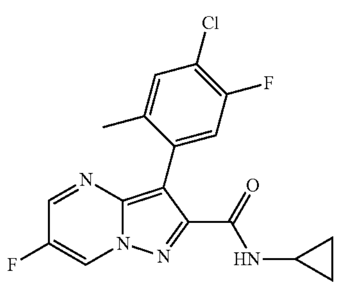 [SMILES: Cc1cc(Cl)c(F)cc1-c1c(C(=O)NC2CC2)nn2cc(F)cnc12] | 362.9 |
| 65 | 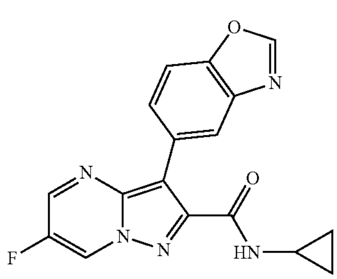 [SMILES: O=C(NC1CC1)c1nn2cc(F)cnc2c1-c1ccc2ocnc2c1] | 337.9 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
|---|---|---|
| 66 | 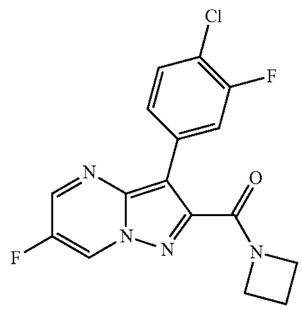 [SMILES: O=C(c1nn2cc(F)cnc2c1-c1ccc(Cl)c(F)c1)N1CCC1] | 348.9 |
| 67 | 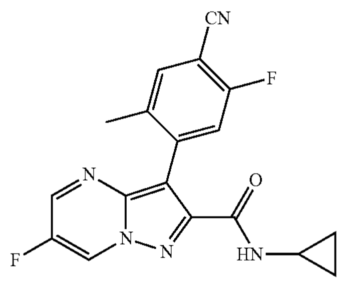 [SMILES: Cc1cc(C#N)c(F)cc1-c1c(C(=O)NC2CC2)nn2cc(F)cnc12] | 353.9 |
| 68 | 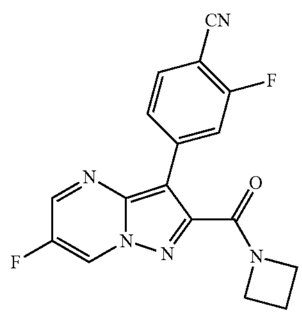 | 339.9 |
| 69 | 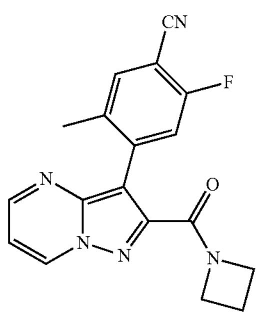 [SMILES: Cc1cc(C#N)c(F)cc1-c1c(C(=O)N2CCC2)nn2cccnc12] | 335.9 |
| 70 | 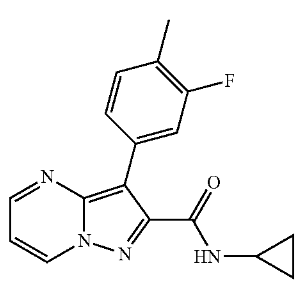 [SMILES: Cc1ccc(-c2c(C(=O)NC3CC3)nn3cccnc23)cc1F] | 311.1 |

TABLE 2-continued
Examples 22-76 were prepared using methods analogous to those employed for Examples 1-21, or via methodology known to those skilled in the art.
Structure and mass spectrometry data for Examples 22-76.
| Example Number | Structure | Mass spectrum, observed ion m/z [M + H]+ |
|---|---|---|
| 71 | 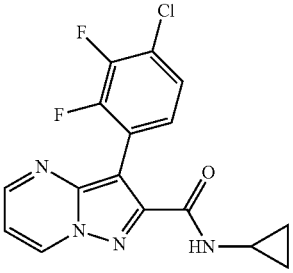 [SMILES: O=C(NC1CC1)c1nn2cccnc2c1-c1ccc(Cl)c(F)c1F] | 348.9 |
| 72 | 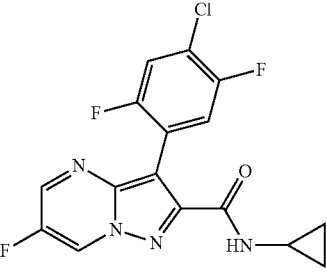 | 366.8 |
| 73 | 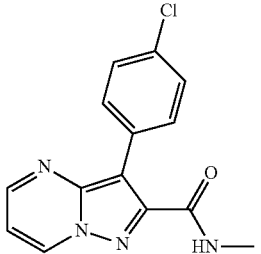 [SMILES: CNC(=O)c1nn2cccnc2c1-c1ccc(Cl)cc1] | 287.1, 289.1 |
| 74 | 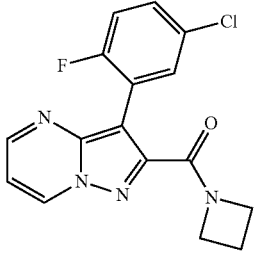 [SMILES: O=C(c1nn2cccnc2c1-c1cc(Cl)ccc1F)N1CCC1] | 331.0, 333.1 |
| 75 | 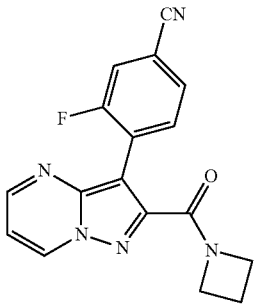 [SMILES: N#Cc1ccc(-c2c(C(=O)N3CCC3)nn3cccnc23)c(F)c1] | 322.1 |

TABLE 2-continued

Examples 22-76 were prepared using methods analogous to those employed for Examples 1-21, or via methodology known to those skilled in the art.
Structure and mass spectrometry data for Examples 22-76.

| Example Number | Structure | Mass spectrum, observed ion m/z [M + H]+ |
| --- | --- | --- |
| 76 | (structure) | 322.1 |

The PDE4A, PDE4B, PDE4C and PDE4D binding affinity for the compounds of the present invention was determined utilizing the following biological assay(s):

BIOLOGICAL ASSAYS

Human PDE4A3 coding sequence (amino acids 2 to 825 from the sequence with accession number NP_001104779) was cloned into the baculovirus expression vector pFastBac (Invitrogen) engineered to include an N-terminal His6 affinity tag and a c-terminal FLAG affinity tag to aid in purification. The recombinant Bacmid was isolated and used to transfect insect cells to generate a viral stock. To generate cell paste for purification, insect cells were infected with the virus stock and cells were harvested 72 hours after infection. Insect cell paste was lysed and after centrifugation, the supernatant was batch bound to Ni-NTA agarose (GE Healthcare) and eluted with 250 mM imidazole. This eluate was diluted with FLAG buffer (50 mM Tris HCL pH 7.5, 100 mM NaCl, 5% Glycerol, 1 mM TCEP with protease inhibitors) and batch bound to ant-FLAG M2 agarose (Sigma) overnight at 4° C. The agarose was packed into a column, washed with buffer and eluted with buffer containing elute using 250 ug/ml Flag-peptide. Fractions were analyzed using SDS-PAGE Coomassie blue staining and pooled based on purity. Pooled fractions were chromatographed on a S200 120 ml column (GE Healthcare) in 50 mM Tris HCL pH 7.5, 150 mM NaCl, 10% Glycerol, 2 mM TCEP with protease inhibitors. PDE4A3 fractions were analyzed by SDS-PAGE Coomassie blue staining, pooled based on purity, dialyzed against 50 mM Tris HCL pH 7.5, 100 mM NaCl, 20% Glycerol, 2 mM TCEP, frozen and stored at −80° C.

Human PDE4B1 coding sequence (amino acids 122 to 736 from the sequence with accession number Q07343) with the mutations resulting in the amino acid substitutions S134E, S654A, S659A, and S661A was cloned into the baculovirus expression vector pFastBac (Invitrogen) engineered to include a N-terminal His6 affinity tag to aid in purification followed by a thrombin cleavage site. The recombinant Bacmid was isolated and used to transfect insect cells to generate a viral stock. To generate cell paste for purification, insect cells were infected with the virus stock and cells were harvested 72 hours after infection as described in Seeger, T. F. et al., Brain Research 985 (2003) 113-126. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q buffer A (20 mM Tris HCl pH 8, 5% glycerol, 1 mM TCEP) to reduce NaCl to ~100 mM and loaded on a Source 15Q (GE Healthcare) column. After washing with Q buffer A/10% buffer B to baseline, PDE4D was eluted with a gradient from 10% to 60% of Buffer B (20 mM Tris HCl pH 8, 1 M NaCl, 5% glycerol, 1 mM TCEP). PDE4D fractions were analyzed by SDS-PAGE Coomassie blue staining, pooled based on purity, frozen and stored at −80° C.

Human PDE4C1 coding sequence (amino acids 2 to 712 from the sequence with accession number NP_000914.2) was cloned into the baculovirus expression vector pFastBac (Invitrogen) engineered to include an N-terminal His6 affinity tag and a c-terminal FLAG affinity tag to aid in purification. The recombinant Bacmid was isolated and used to transfect insect cells to generate a viral stock. To generate cell paste for purification, insect cells were infected with the virus stock and cells were harvested 72 hours after infection. Insect cell paste was lysed and after centrifugation, the supernatant was batch bound to Ni-NTA agarose (GE Healthcare) and eluted with 250 mM imidazole. This eluate was diluted with FLAG buffer (50 mM Tris HCL pH 7.5, 100 mM NaCl, 5% Glycerol, 1 mM TCEP with protease inhibitors) and batch bound to ant-FLAG M2 agarose (Sigma) overnight at 4° C. The agarose was packed into a column, washed with buffer and eluted with buffer containing elute using 250 ug/ml Flag-peptide. Fractions were analyzed using SDS-PAGE Coomassie blue staining and pooled based on purity. Pooled fractions were chromatographed on a S200 120 ml column (GE Healthcare) in 50 mM Tris HCL pH 7.5, 150 mM NaCl, 10% Glycerol, 2 mM TCEP with protease inhibitors. PDE4C1 fractions were analyzed by SDS-PAGE Coomassie blue staining, pooled based on purity, dialyzed against 50 mM Tris HCL pH 7.5, 100 mM NaCl, 20% Glycerol, 2 mM TCEP, frozen and stored at −80° C.

A portion of the human PDE4D3 coding sequence (amino acids 50 to 672 from the sequence with accession number Q08499-2) was cloned into the baculovirus expression vector pFastBac (Invitrogen) engineered to include a C-terminal His6 affinity tag to aid in purification as described in Seeger, T. F. et al., Brain Research 985 (2003) 113-126. The recombinant Bacmid was isolated and used to transfect insect cells to generate a viral stock. To generate cell paste for purification, insect cells were infected and cells were harvested 72 hours after infection. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q Buffer A (50 mM Tris HCl pH 8, 4% glycerol, 100 mM NaCl, 1 mM TCEP, Protease inhibitors EDTA-free (Roche)) to reduce NaCl to ~200 mM, and loaded on a Q Sepharose (GE Healthcare) column. After washing with Q buffer A to baseline, PDE4D was eluted with a gradient from 10% to 60% of Buffer B (50 mM Tris HCl pH 8, 1 M NaCl, 4% glycerol, 1 mM TCEP). PDE4D fractions were analyzed by SDS-PAGE Coomassie blue staining, pooled based on purity, frozen and stored at −80° C.

The PDE4A3, PDE4B1, PDE4C1 and PDE4D3 assays use the Scintillation Proximity Assay (SPA) technology to measure the inhibition of human recombinant PDE4A1, PDE4B3, PDE4C1, and PDE4D3 enzyme activity by compounds in vitro. The PDE4A1, PDE4B3, PDE4C1, and PDE4D3 assays are run in parallel using identical parameters, except for the concentration of enzyme (80 pM PDE4A3, 40 pM PDE4B3, 40 pM PDE4C1 and 10 pM PDE4D). The assays are performed in a 384-well format with 50 uL assay buffer (50 mM TRIS pH7.5; 1.3 mM MgCl2; 0.01% Brij) containing enough PDE4A3, PDE4B1, PDE4C1, and PDE4D to convert ~20% of substrate (1 µM cAMP consisting of 20 nM 3H-cAMP+980 uM cold cAMP) and a range of inhibitors. Reactions are incubated for 30 min at 25° C. The addition of 20 uL of 8 mg/ml yitrium silicate SPA beads (Perkin Elmer) stops the reaction. The plates are sealed (TopSeal, Perkin Elmer) and the beads are allowed to settle for 8 hrs, after which they are read on the Trilux Microbeta overnight.

TABLE 3

Table 3. Biological data for Examples 1-76.

| Example Number | Human PDE4A FL; $IC_{50}$ (nM)[a] | Human PDE4B FL; $IC_{50}$ (nM)[a] | Human PDE4C FL; $IC_{50}$ (nM)[a] | Human PDE4D FL; $IC_{50}$ (nM)[a] | IUPAC Name |
|---|---|---|---|---|---|
| 1 | 17.9 | 52.7[b] | 84.2 | >9300[b] | azetidin-1-yl[3-(4-chlorophenyl)pyrazolo[1,5-a]pyrimidin-2-yl]methanone |
| 2 | 61.4 | 34.6 | 60.6 | 4150 | 3-(4-chlorophenyl)-N-propylpyrazolo[1,5-a]pyrimidine-2-carboxamide |
| 3' | Not applicable | Not applicable | Not applicable | Not applicable | Not applicable |
| 4 | 553 | 894 | 1540 | >30000 | N-[3-(4-chloro-3-fluorophenyl)pyrazolo[1,5-a]pyrimidin-2-yl]butanamide |
| 5 | 3.29[b] | 5.87[b] | 18.0[b] | 662[b] | 3-(4-chloro-3-fluorophenyl)-N-cyclopropylpyrazolo[1,5-a]pyrimidine-2-carboxamide |
| 6 | 28.7[b] | 55.2[b] | 66.0[b] | >10400[b] | 3-(4-chloro-2-methylphenyl)-N-cyclopropylpyrazolo[1,5-a]pyrimidine-2-carboxamide |
| 7 | 8.77[b] | 16.1[b] | 23.4[b] | 1080[b] | 3-(4-chlorophenyl)-N-cyclopropyl-6-fluoropyrazolo[1,5-a]pyrimidine-2-carboxamide |
| 8 | 190 | 1090 | 965 | >25200 | 3-(4-chlorophenyl)-N-(pyrimidin-2-yl)pyrazolo[1,5-a]pyrimidine-2-carboxamide |
| 9 | 16.7[b] | 34.4[b] | 55.3[b] | 3710[b] | azetidin-1-yl[3-(4-chlorophenyl)-6-fluoropyrazolo[1,5-a]pyrimidin-2-yl]methanone, formate salt |
| 10 | 25.3 | 96.9[b] | 42.9 | 5840[b] | 3-(4-chlorophenyl)-N-cyclopropylpyrazolo[1,5-a]pyrimidine-2-carboxamide |
| 11 | 80.8 | 62.4[b] | 276 | >10700[b] | 3-(4-chlorophenyl)-N-(1-methylcyclopropyl)pyrazolo[1,5-a]pyrimidine-2-carboxamide |
| 12 | 22.0[c] | 6.06[b] | 48.0[c] | 993[b] | azetidin-1-yl[3-(4-chloro-3-fluorophenyl)pyrazolo[1,5-a]pyrimidin-2-yl]methanone |
| 13 | 27.2 | 57.9[b] | 57.9 | 2460[b] | 3-(5-chloro-2-fluorophenyl)-N-cyclopropylpyrazolo[1,5-a]pyrimidine-2-carboxamide |
| 14 | 51.8[b] | 179[b] | 83.3[b] | >16700[b] | 3-(4-chloro-2-fluorophenyl)-N-cyclopropylpyrazolo[1,5-a]pyrimidine-2-carboxamide |
| 15 | 109 | 51.7 | 52.7 | 6630 | 4-[2-(azetidin-1-ylcarbonyl)pyrazolo[1,5-a]pyrimidin-3-yl]-2-fluorobenzonitrile |
| 16 | 15.9 | 54.3 | 79.8 | 2510 | 3-(4-cyano-5-fluoro-2-methylphenyl)-N-ethylpyrazolo[1,5-a]pyrimidine-2-carboxamide |

TABLE 3-continued

Table 3. Biological data for Examples 1-76.

| Example Number | Human PDE4A FL; IC$_{50}$ (nM)[a] | Human PDE4B FL; IC$_{50}$ (nM)[a] | Human PDE4C FL; IC$_{50}$ (nM)[a] | Human PDE4D FL; IC$_{50}$ (nM)[a] | IUPAC Name |
|---|---|---|---|---|---|
| 17 | 8.46 | 21.0 | 79.8 | 967 | 3-(4-chloro-5-fluoro-2-methylphenyl)-N-ethylpyrazolo[1,5-a]pyrimidine-2-carboxamide |
| 18 | 39.9 | 150 | 97.3 | 6880 | 3-(4-chloro-2-methylphenyl)-N-ethylpyrazolo[1,5-a]pyrimidine-2-carboxamide |
| 19 | 11.3 | 41.4 | 36.4 | 2110 | 3-(4-chloro-2,5-difluorophenyl)-N-ethylpyrazolo[1,5-a]pyrimidine-2-carboxamide |
| 20 | 64.5 | 67.4[b] | 111 | 10900[b] | azetidin-1-yl[3-(4-chloro-2-fluorophenyl)pyrazolo[1,5-a]pyrimidin-2-yl]methanone |
| 21 | 16.6[b] | 44.6[b] | 56.5[b] | 4830[b] | azetidin-1-yl[3-(4-chloro-2-methylphenyl)pyrazolo[1,5-a]pyrimidin-2-yl]methanone |
| 22 | 167[c] | 273[c] | 124[c] | 8810[c] | 3-(4-cyano-5-fluoro-2-methylphenyl)-N-cyclobutylpyrazolo[1,5-a]pyrimidine-2-carboxamide |
| 23 | 8.42[b] | 25.9[b] | 39.4[b] | 442[b] | 3-(4-cyano-5-fluoro-2-methylphenyl)-N-cyclopropylpyrazolo[1,5-a]pyrimidine-2-carboxamide |
| 24 | 8.53 | 35.4 | 44.0 | 606 | 3-(4-chloro-5-fluoro-2-methylphenyl)-N-cyclobutylpyrazolo[1,5-a]pyrimidine-2-carboxamide |
| 25 | 5.35[b] | 9.61[b] | 17.4[b] | 283[b] | 3-(4-chloro-5-fluoro-2-methylphenyl)-N-cyclopropylpyrazolo[1,5-a]pyrimidine-2-carboxamide |
| 26 | 411 | 488 | 626 | 4910[b] | 3-(4-chlorophenyl)-N-(propan-2-yl)pyrazolo[1,5-a]pyrimidine-2-carboxamide |
| 27 | 55.8 | 124[b] | 217 | 6200[b] | N-(bicyclo[1.1.1]pent-1-yl)-3-(4-chlorophenyl)pyrazolo[1,5-a]pyrimidine-2-carboxamide |
| 28 | 14.4 | 3.70[b] | 19.9 | 140[b] | 3-(4-chloro-3-fluorophenyl)-N-[(1R,2S)-2-fluorocyclopropyl]pyrazolo[1,5-a]pyrimidine-2-carboxamide |
| 29 | ND | 132 | ND | 3010 | 3-(5-chloropyridin-3-yl)-N-cyclopropylpyrazolo[1,5-a]pyrimidine-2-carboxamide |
| 30 | ND | 2180 | ND | 27000 | N-[3-(4-chloro-3-fluorophenyl)pyrazolo[1,5-a]pyrimidin-2-yl]benzamide |
| 31 | 36.2 | 51.0[b] | 106 | 2120[b] | 3-(3-chlorophenyl)-N-cyclopropylpyrazolo[1,5-a]pyrimidine-2-carboxamide, hydrochloride salt |
| 32 | ND | 9.98 | ND | 720 | N-cyclopropyl-3-(3,4-dichlorophenyl)pyrazolo[1,5-a]pyrimidine-2-carboxamide, hydrochloride salt |
| 33 | 92.6 | 3.30 | 170 | 408[b] | 3-(4-chloro-3,5-difluorophenyl)-N-cyclopropylpyrazolo[1,5-a]pyrimidine-2-carboxamide, hydrochloride salt |
| 34 | 120 | 138[b] | 449 | >12300[b] | 3-(4-chlorophenyl)-N-(2-methylcyclopropyl)pyrazolo[1,5-a]pyrimidine-2-carboxamide |
| 35 | 1110 | 1860[b] | 710 | >30000[b] | 3-(4-chlorophenyl)-N-cyclopropyl-N-methylpyrazolo[1,5-a]pyrimidine-2-carboxamide, hydrochloride salt |
| 36 | 67.2 | 452 | 452 | >25200[b] | 3-(4-chlorophenyl)-N-[1-(trifluoromethyl)cyclopropyl]pyrazolo[1,5-a]pyrimidine-2-carboxamide, hydrochloride salt |

TABLE 3-continued

Table 3. Biological data for Examples 1-76.

| Example Number | Human PDE4A FL; IC$_{50}$ (nM)[a] | Human PDE4B FL; IC$_{50}$ (nM)[a] | Human PDE4C FL; IC$_{50}$ (nM)[a] | Human PDE4D FL; IC$_{50}$ (nM)[a] | IUPAC Name |
|---|---|---|---|---|---|
| 37 | ND | 31.5 | ND | 691[b] | azetidin-1-yl{3-[2-(difluoromethoxy)pyridin-4-yl]pyrazolo[1,5-a]pyrimidin-2-yl}methanone |
| 38 | ND | 51.1 | ND | 706[b] | N-cyclopropyl-3-[2-(difluoromethoxy)pyridin-4-yl]pyrazolo[1,5-a]pyrimidine-2-carboxamide, formate salt |
| 39 | 23.2 | 12.9[b] | 66.3 | 300[b] | 3-(4-chloro-3-fluorophenyl)-N-(2,2-difluorocyclopropyl)pyrazolo[1,5-a]pyrimidine-2-carboxamide |
| 40 | ND | 68.0 | ND | 2360 | 3-(4-chlorophenyl)-N-(2,2-difluorocyclopropyl)pyrazolo[1,5-a]pyrimidine-2-carboxamide |
| 41 | ND | 5.32 | ND | 350 | azetidin-1-yl[3-(4-chloro-3,5-difluorophenyl)pyrazolo[1,5-a]pyrimidin-2-yl]methanone |
| 42 | 212 | 474 | 1190 | >18400 | N-cyclopropyl-3-(2-methoxypyridin-4-yl)pyrazolo[1,5-a]pyrimidine-2-carboxamide |
| 43 | 146 | 221[b] | 178 | >14400[b] | 3-(1,3-benzoxazol-6-yl)-N-cyclopropylpyrazolo[1,5-a]pyrimidine-2-carboxamide |
| 44 | 192 | 358 | 898 | >11900[b] | 3-(6-cyanopyridin-3-yl)-N-cyclopropylpyrazolo[1,5-a]pyrimidine-2-carboxamide |
| 45 | 22.0 | 51.0[b] | 42.1 | 1320[b] | 3-(4-cyano-2,5-difluorophenyl)-N-cyclopropylpyrazolo[1,5-a]pyrimidine-2-carboxamide |
| 46 | 14.7 | 54.5 | 44.0 | 979 | 4-[2-(azetidin-1-ylcarbonyl)pyrazolo[1,5-a]pyrimidin-3-yl]-2,5-difluorobenzonitrile |
| 47 | 4.69[b] | 24.4[b] | 13.9[b] | 819[b] | 3-(4-chloro-2,5-difluorophenyl)-N-cyclopropylpyrazolo[1,5-a]pyrimidine-2-carboxamide |
| 48 | 167 | 236 | 76.4 | >16000 | azetidin-1-yl[3-(3-chlorophenyl)pyrazolo[1,5-a]pyrimidin-2-yl]methanone |
| 49 | 7.28[b] | 63.5[b] | 29.6[b] | 1290[b] | azetidin-1-yl[3-(4-chloro-2,5-difluorophenyl)pyrazolo[1,5-a]pyrimidin-2-yl]methanone |
| 50 | 17.7 | 48.3 | 70.8 | >4870 | 3-[2-(difluoromethoxy)pyridin-4-yl]-N-ethylpyrazolo[1,5-a]pyrimidine-2-carboxamide |
| 51 | 144 | 488 | 314 | >16500 | 3-(4-chloro-2-methylphenyl)-N-(propan-2-yl)pyrazolo[1,5-a]pyrimidine-2-carboxamide |
| 52 | 142 | 234 | 115 | 5930 | 3-(4-chlorophenyl)-N-ethylpyrazolo[1,5-a]pyrimidine-2-carboxamide |
| 53 | 7.66 | 32.0 | 21.8 | 830 | 3-(4-chloro-3-fluorophenyl)-N-ethylpyrazolo[1,5-a]pyrimidine-2-carboxamide |
| 54 | 12.9 | 24.5 | 59.0 | 469 | 3-(4-chloro-5-fluoro-2-methylphenyl)-N-(propan-2-yl)pyrazolo[1,5-a]pyrimidine-2-carboxamide |
| 55 | 8.75[b] | 30.5[b] | 28.5[b] | 1060[b] | 3-(4-chloro-2-methylphenyl)-N-cyclopropyl-6-fluoropyrazolo[1,5-a]pyrimidine-2-carboxamide |
| 56 | 3.92 | 22.3 | 19.4 | 78.4 | N-cyclopropyl-3-[2-(difluoromethoxy)pyridin-4-yl]-6-fluoropyrazolo[1,5-a]pyrimidine-2-carboxamide |
| 57 | 0.461 | 2.71 | 2.83 | 92.1 | 3-(4-chloro-3,5-difluorophenyl)-N-cyclopropyl-6-fluoropyrazolo[1,5-a]pyrimidine-2-carboxamide |

TABLE 3-continued

Table 3. Biological data for Examples 1-76.

| Example Number | Human PDE4A FL; $IC_{50}$ (nM)[a] | Human PDE4B FL; $IC_{50}$ (nM)[a] | Human PDE4C FL; $IC_{50}$ (nM)[a] | Human PDE4D FL; $IC_{50}$ (nM)[a] | IUPAC Name |
|---|---|---|---|---|---|
| 58 | 4.04 | 20.1 | 9.00 | 430 | 3-(4-chloro-2,3-difluorophenyl)-N-cyclopropyl-6-fluoropyrazolo[1,5-a]pyrimidine-2-carboxamide |
| 59 | 1.19 | 4.93 | 7.72 | 159 | 3-(4-chloro-3-fluorophenyl)-N-cyclopropyl-6-fluoropyrazolo[1,5-a]pyrimidine-2-carboxamide |
| 60 | 47.1 | 226 | 650 | >15500 | 3-(1,3-benzoxazol-5-yl)-N-cyclopropylpyrazolo[1,5-a]pyrimidine-2-carboxamide |
| 61 | 2.00[c] | 8.00[c] | 20.0[c] | 98.0[c] | azetidin-1-yl[3-(4-chloro-5-fluoro-2-methylphenyl)pyrazolo[1,5-a]pyrimidin-2-yl]methanone |
| 62 | 4.33 | 17.3 | 37.8 | 242 | 4-[2-(azetidin-1-ylcarbonyl)pyrazolo[1,5-a]pyrimidin-3-yl]-2,6-difluorobenzonitrile |
| 63 | 4.02 | 13.2 | 9.50 | 459 | N-cyclopropyl-6-fluoro-3-(3-fluoro-4-methylphenyl)pyrazolo[1,5-a]pyrimidine-2-carboxamide |
| 64 | 1.00 | 2.00 | 4.47 | 52.6 | 3-(4-chloro-5-fluoro-2-methylphenyl)-N-cyclopropyl-6-fluoropyrazolo[1,5-a]pyrimidine-2-carboxamide |
| 65 | 57.0[c] | 59.0[c] | 128[c] | 1160[c] | 3-(1,3-benzoxazol-5-yl)-N-cyclopropyl-6-fluoropyrazolo[1,5-a]pyrimidine-2-carboxamide |
| 66 | 2.00[c] | 7.00[c] | 9.00[c] | 79.0[c] | azetidin-1-yl[3-(4-chloro-3-fluorophenyl)-6-fluoropyrazolo[1,5-a]pyrimidin-2-yl]methanone |
| 67 | 3.46 | 16.4 | 26.8 | 111 | 3-(4-cyano-5-fluoro-2-methylphenyl)-N-cyclopropyl-6-fluoropyrazolo[1,5-a]pyrimidine-2-carboxamide |
| 68 | 3.31 | 16.8 | 32.9 | 261 | 4-[2-(azetidin-1-ylcarbonyl)-6-fluoropyrazolo[1,5-a]pyrimidin-3-yl]-2-fluorobenzonitrile |
| 69 | 3.37 | 17.3 | 36.1 | 92.9 | 4-[2-(azetidin-1-ylcarbonyl)pyrazolo[1,5-a]pyrimidin-3-yl]-2-fluoro-5-methylbenzonitrile |
| 70 | 8.09 | 23.6 | 17.0 | 680 | N-cyclopropyl-3-(3-fluoro-4-methylphenyl)pyrazolo[1,5-a]pyrimidine-2-carboxamide |
| 71 | 10.2 | 25.5 | 11.1 | 797 | 3-(4-chloro-2,3-difluorophenyl)-N-cyclopropylpyrazolo[1,5-a]pyrimidine-2-carboxamide |
| 72 | 0.770 | 3.02 | 5.18 | 43.0 | 3-(4-chloro-2,5-difluorophenyl)-N-cyclopropyl-6-fluoropyrazolo[1,5-a]pyrimidine-2-carboxamide |
| 73 | 663 | 2070 | 435 | >28500 | 3-(4-chlorophenyl)-N-methylpyrazolo[1,5-a]pyrimidine-2-carboxamide |
| 74 | ND | 45.8 | ND | 5990 | azetidin-1-yl[3-(5-chloro-2-fluorophenyl)pyrazolo[1,5-a]pyrimidin-2-yl]methanone |
| 75 | 745 | 377[b] | 292 | >28000[b] | 4-[2-(azetidin-1-ylcarbonyl)pyrazolo[1,5-a]pyrimidin-3-yl]-3-fluorobenzonitrile |
| 76 | ND | 443 | ND | >30000 | 3-(4-cyano-2-fluorophenyl)-N-cyclopropylpyrazolo[1,5-a]pyrimidine-2-carboxamide |

[a]Values represent the geometric mean of 2-7 determinations, unless otherwise indicated.
[b]Value represents the geometric mean of ≥8 determinations.
[c]Value represents a single determination.
ND. Value not determined.

What is claimed:
1. A compound selected from the group consisting of:
Azetidin-1-yl[3-(4-chlorophenyl)pyrazolo[1,5-a]pyrimidin-2-yl]methanone;
3-(4-Chlorophenyl)-N-propylpyrazolo[1,5-a]pyrimidine-2-carboxamide;
3-(4-chloro-3-fluorophenyl)pyrazolo[1,5-a]pyrimidin-2-amine;
N-[3-(4-Chloro-3-fluorophenyl)pyrazolo[1,5-a]pyrimidin-2-yl]butanamide;
3-(4-Chloro-3-fluorophenyl)-N-cyclopropylpyrazolo[1,5-a]pyrimidine-2-carboxamide;
3-(4-Chloro-2-methylphenyl)-N-cyclopropylpyrazolo[1,5-a]pyrimidine-2-carboxamide;
3-(4-Chlorophenyl)-N-cyclopropyl-6-fluoropyrazolo[1,5-a]pyrimidine-2-carboxamide;
3-(4-Chlorophenyl)-N-(pyrimidin-2-yl)pyrazolo[1,5-a]pyrimidine-2-carboxamide;
Azetidin-1-yl[3-(4-chlorophenyl)-6-fluoropyrazolo[1,5-a]pyrimidin-2-yl]methanone;
3-(4-chlorophenyl)-N-cyclopropylpyrazolo[1,5-a]pyrimidine-2-carboxamide;
3-(4-chlorophenyl)-N-(1-methylcyclopropyl)pyrazolo[1,5-a]pyrimidine-2-carboxamide;
azetidin-1-yl[3-(4-chloro-3-fluorophenyl)pyrazolo[1,5-a]pyrimidin-2-yl]methanone;
3-(5-chloro-2-fluorophenyl)-N-cyclopropylpyrazolo[1,5-a]pyrimidine-2-carboxamide;
3-(4-chloro-2-fluorophenyl)-N-cyclopropylpyrazolo[1,5-a]pyrimidine-2-carboxamide;
4-[2-(azetidin-1-ylcarbonyl)pyrazolo[1,5-a]pyrimidin-3-yl]-2-fluorobenzonitrile;
3-(4-cyano-5-fluoro-2-methylphenyl)-N-ethylpyrazolo[1,5-a]pyrimidine-2-carboxamide;
3-(4-chloro-5-fluoro-2-methylphenyl)-N-ethylpyrazolo[1,5-a]pyrimidine-2-carboxamide;
3-(4-chloro-2-methylphenyl)-N-ethylpyrazolo[1,5-a]pyrimidine-2-carboxamide;
3-(4-chloro-2,5-difluorophenyl)-N-ethylpyrazolo[1,5-a]pyrimidine-2-carboxamide;
azetidin-1-yl[3-(4-chloro-2-fluorophenyl)pyrazolo[1,5-a]pyrimidin-2-yl]methanone;
azetidin-1-yl[3-(4-chloro-2-methylphenyl)pyrazolo[1,5-a]pyrimidin-2-yl]methanone;
3-(4-cyano-5-fluoro-2-methylphenyl)-N-cyclobutylpyrazolo[1,5-a]pyrimidine-2-carboxamide;
3-(4-cyano-5-fluoro-2-methylphenyl)-N-cyclopropylpyrazolo[1,5-a]pyrimidine-2-carboxamide;
3-(4-chloro-5-fluoro-2-methylphenyl)-N-cyclobutylpyrazolo[1,5-a]pyrimidine-2-carboxamide;
3-(4-chloro-5-fluoro-2-methylphenyl)-N-cyclopropylpyrazolo[1,5-a]pyrimidine-2-carboxamide;
3-(4-chlorophenyl)-N-(propan-2-yl)pyrazolo[1,5-a]pyrimidine-2-carboxamide;
N-(bicyclo[1.1.1]pent-1-yl)-3-(4-chlorophenyl)pyrazolo[1,5-a]pyrimidine-2-carboxamide;
3-(4-chloro-3-fluorophenyl)-N-[(1R,2S)-2-fluorocyclopropyl]pyrazolo[1,5-a]pyrimidine-2-carboxamide;
3-(5-chloropyridin-3-yl)-N-cyclopropylpyrazolo[1,5-a]pyrimidine-2-carboxamide;
N-[3-(4-chloro-3-fluorophenyl)pyrazolo[1,5-a]pyrimidin-2-yl]benzamide;
3-(3-chlorophenyl)-N-cyclopropylpyrazolo[1,5-a]pyrimidine-2-carboxamide;
N-cyclopropyl-3-(3,4-dichlorophenyl)pyrazolo[1,5-a]pyrimidine-2-carboxamide;
3-(4-chloro-3,5-difluorophenyl)-N-cyclopropylpyrazolo[1,5-a]pyrimidine-2-carboxamide;
3-(4-chlorophenyl)-N-(2-methylcyclopropyl)pyrazolo[1,5-a]pyrimidine-2-carboxamide;
3-(4-chlorophenyl)-N-cyclopropyl-N-methylpyrazolo[1,5-a]pyrimidine-2-carboxamide;
3-(4-chlorophenyl)-N-[1-(trifluoromethyl)cyclopropyl]pyrazolo[1,5-a]pyrimidine-2-carboxamide;
azetidin-1-yl{3-[2-(difluoromethoxy)pyridin-4-yl]pyrazolo[1,5-a]pyrimidin-2-yl}methanone;
N-cyclopropyl-3-[2-(difluoromethoxy)pyridin-4-yl]pyrazolo[1,5-a]pyrimidine-2-carboxamide;
3-(4-chloro-3-fluorophenyl)-N-(2,2-difluorocyclopropyl)pyrazolo[1,5-a]pyrimidine-2-carboxamide;
3-(4-chlorophenyl)-N-(2,2-difluorocyclopropyl)pyrazolo[1,5-a]pyrimidine-2-carboxamide;
azetidin-1-yl[3-(4-chloro-3,5-difluorophenyl)pyrazolo[1,5-a]pyrimidin-2-yl]methanone;
N-cyclopropyl-3-(2-methoxypyridin-4-yl)pyrazolo[1,5-a]pyrimidine-2-carboxamide;
3-(1,3-benzoxazol-6-yl)-N-cyclopropylpyrazolo[1,5-a]pyrimidine-2-carboxamide;
3-(6-cyanopyridin-3-yl)-N-cyclopropylpyrazolo[1,5-a]pyrimidine-2-carboxamide;
3-(4-cyano-2,5-difluorophenyl)-N-cyclopropylpyrazolo[1,5-a]pyrimidine-2-carboxamide;
4-[2-(azetidin-1-ylcarbonyl)pyrazolo[1,5-a]pyrimidin-3-yl]-2,5-difluorobenzonitrile;
3-(4-chloro-2,5-difluorophenyl)-N-cyclopropylpyrazolo[1,5-a]pyrimidine-2-carboxamide;
azetidin-1-yl[3-(3-chlorophenyl)pyrazolo[1,5-a]pyrimidin-2-yl]methanone;
azetidin-1-yl[3-(4-chloro-2,5-difluorophenyl)pyrazolo[1,5-a]pyrimidin-2-yl]methanone;
3-[2-(difluoromethoxy)pyridin-4-yl]-N-ethylpyrazolo[1,5-a]pyrimidine-2-carboxamide;
3-(4-chloro-2-methylphenyl)-N-(propan-2-yl)pyrazolo[1,5-a]pyrimidine-2-carboxamide;
3-(4-chlorophenyl)-N-ethylpyrazolo[1,5-a]pyrimidine-2-carboxamide;
3-(4-chloro-3-fluorophenyl)-N-ethylpyrazolo[1,5-a]pyrimidine-2-carboxamide;
3-(4-chloro-5-fluoro-2-methylphenyl)-N-(propan-2-yl)pyrazolo[1,5-a]pyrimidine-2-carboxamide;
3-(4-chloro-2-methylphenyl)-N-cyclopropyl-6-fluoropyrazolo[1,5-a]pyrimidine-2-carboxamide;
N-cyclopropyl-3-[2-(difluoromethoxy)pyridin-4-yl]-6-fluoropyrazolo[1,5-a]pyrimidine-2-carboxamide;
3-(4-chloro-3,5-difluorophenyl)-N-cyclopropyl-6-fluoropyrazolo[1,5-a]pyrimidine-2-carboxamide;
3-(4-chloro-2,3-difluorophenyl)-N-cyclopropyl-6-fluoropyrazolo[1,5-a]pyrimidine-2-carboxamide;
3-(4-chloro-3-fluorophenyl)-N-cyclopropyl-6-fluoropyrazolo[1,5-a]pyrimidine-2-carboxamide;
3-(1,3-benzoxazol-5-yl)-N-cyclopropylpyrazolo[1,5-a]pyrimidine-2-carboxamide;
azetidin-1-yl[3-(4-chloro-5-fluoro-2-methylphenyl)pyrazolo[1,5-a]pyrimidin-2-yl]methanone;
4-[2-(azetidin-1-ylcarbonyl)pyrazolo[1,5-a]pyrimidin-3-yl]-2,6-difluorobenzonitrile;
N-cyclopropyl-6-fluoro-3-(3-fluoro-4-methylphenyl)pyrazolo[1,5-a]pyrimidine-2-carboxamide;
3-(4-chloro-5-fluoro-2-methylphenyl)-N-cyclopropyl-6-fluoropyrazolo[1,5-a]pyrimidine-2-carboxamide;
3-(1,3-benzoxazol-5-yl)-N-cyclopropyl-6-fluoropyrazolo[1,5-a]pyrimidine-2-carboxamide;

azetidin-1-yl[3-(4-chloro-3-fluorophenyl)-6-fluoropyrazolo[1,5-a]pyrimidin-2-yl]methanone;
3-(4-cyano-5-fluoro-2-methylphenyl)-N-cyclopropyl-6-fluoropyrazolo[1,5-a]pyrimidine-2-carboxamide;
4-[2-(azetidin-1-ylcarbonyl)-6-fluoropyrazolo[1,5-a]pyrimidin-3-yl]-2-fluorobenzonitrile;
4-[2-(azetidin-1-ylcarbonyl)pyrazolo[1,5-a]pyrimidin-3-yl]-2-fluoro-5-methylbenzonitrile;
N-cyclopropyl-3-(3-fluoro-4-methylphenyl)pyrazolo[1,5-a]pyrimidine-2-carboxamide;
3-(4-chloro-2,3-difluorophenyl)-N-cyclopropylpyrazolo[1,5-a]pyrimidine-2-carboxamide;
3-(4-chloro-2,5-difluorophenyl)-N-cyclopropyl-6-fluoropyrazolo[1,5-a]pyrimidine-2-carboxamide;
3-(4-chlorophenyl)-N-methylpyrazolo[1,5-a]pyrimidine-2-carboxamide;
azetidin-1-yl[3-(5-chloro-2-fluorophenyl)pyrazolo[1,5-a]pyrimidin-2-yl]methanone;
4-[2-(azetidin-1-ylcarbonyl)pyrazolo[1,5-a]pyrimidin-3-yl]-3-fluorobenzonitrile;
3-(4-cyano-2-fluorophenyl)-N-cyclopropylpyrazolo[1,5-a]pyrimidine-2-carboxamide; or
a pharmaceutically acceptable salt thereof.

2. A compound selected from the group consisting of:
Azetidin-1-yl[3-(4-chlorophenyl)-6-fluoropyrazolo[1,5-a]pyrimidin-2-yl]methanone, formate salt;
3-(3-chlorophenyl)-N-cyclopropylpyrazolo[1,5-a]pyrimidine-2-carboxamide, hydrochloride salt;
N-cyclopropyl-3-(3,4-dichlorophenyl)pyrazolo[1,5-a]pyrimidine-2-carboxamide, hydrochloride salt;
3-(4-chloro-3,5-difluorophenyl)-N-cyclopropylpyrazolo[1,5-a]pyrimidine-2-carboxamide, hydrochloride salt;
3-(4-chlorophenyl)-N-cyclopropyl-N-methylpyrazolo[1,5-a]pyrimidine-2-carboxamide, hydrochloride salt;
3-(4-chlorophenyl)-N-[1-(trifluoromethyl)cyclopropyl]pyrazolo[1,5-a]pyrimidine-2-carboxamide, hydrochloride salt; and
N-cyclopropyl-3-[2-(difluoromethoxy)pyridin-4-yl]pyrazolo[1,5-a]pyrimidine-2-carboxamide, formate salt.

3. A pharmaceutical composition comprising a compound according to claim 1, or a pharmaceutically acceptable salt thereof, and a pharmaceutically acceptable excipient.

* * * * *